US008435576B2

(12) United States Patent
Troplin et al.

(10) Patent No.: US 8,435,576 B2
(45) Date of Patent: May 7, 2013

(54) USE OF COCOA POLYPHENOLS FOR TREATING A PROSTATE HYPERPLASIA, A SPECIFIC COCOA EXTRACT AND APPLICATIONS

(75) Inventors: Philippe Troplin, Louviers (FR); Herwig Bernaert, Merelbeke (BE)

(73) Assignee: Barry Callebaut AG, Zurich (CH)

( * ) Notice: Subject to any disclaimer, the term of this patent is extended or adjusted under 35 U.S.C. 154(b) by 802 days.

(21) Appl. No.: 11/883,265

(22) PCT Filed: Jan. 30, 2006

(86) PCT No.: PCT/FR2006/000204
§ 371 (c)(1),
(2), (4) Date: Apr. 30, 2008

(87) PCT Pub. No.: WO2006/079731
PCT Pub. Date: Aug. 3, 2006

(65) Prior Publication Data
US 2009/0023803 A1    Jan. 22, 2009

Related U.S. Application Data

(60) Provisional application No. 60/647,404, filed on Jan. 28, 2005, provisional application No. 60/739,930, filed on Nov. 28, 2005.

(51) Int. Cl.
*A61K 36/00* (2006.01)

(52) U.S. Cl.
USPC .......................................... 424/776; 424/725

(58) Field of Classification Search ........................ None
See application file for complete search history.

(56) References Cited

U.S. PATENT DOCUMENTS

| 4,237,117 | A | * | 12/1980 | Bruzzese et al. | 424/122 |
| 5,605,929 | A | * | 2/1997 | Liao et al. | 514/456 |
| 5,891,905 | A | | 4/1999 | Romanczyk, Jr. et al. | |
| 6,087,385 | A | * | 7/2000 | Pershadsingh et al. | 514/376 |
| 6,576,660 | B1 | * | 6/2003 | Liao et al. | 514/456 |
| 6,696,484 | B2 | * | 2/2004 | Liao et al. | 514/456 |
| 6,733,779 | B2 | * | 5/2004 | Parks | 424/451 |
| 2001/0053792 | A1 | | 12/2001 | Schmitz et al. | |
| 2002/0012710 | A1 | * | 1/2002 | Lansky | 424/725 |
| 2004/0096566 | A1 | * | 5/2004 | Lecoupeau et al. | 426/593 |
| 2005/0113426 | A1 | * | 5/2005 | Liao et al. | 514/357 |
| 2007/0042102 | A1 | * | 2/2007 | Furcich | 426/631 |

FOREIGN PATENT DOCUMENTS

| WO | WO0191590 | 12/2001 |
| WO | WO0214251 | 2/2002 |

OTHER PUBLICATIONS

Smit, Hendrik J, et al, "Methylxanthines ate the psycho-pharmacologically active constituents of chocolate", Psychopharmacology, vol. 176, No. 3-4, Nov. 2004, pp. 412-419.
Yamagishi, Megumi, et al., "Cacao liquor polyphenols reduce oxidative stress without maintaining α-tocopherol levels in rats fed a vitamin E-deficient diet", Lipids 2001 United States, vol. 36, No. 1, 2002, pp. 67-71.
Wang, Janice F., et al., "A dose-response effect from chocolate consumption on plasma epicatechin and oxidative damage" Journal of Nutrition, vol. 130, No. 8 suppl., 2000, pp. 2115S-2119S.
Record, Ian R., et al., "Chocolate consumption, fecal water antioxidant activity, and hydroxyl radical production", Nutrition and Cancer, vol. 47, No. 2, 2003, pp. 131-135.
Niu, K. C., et al., "Protective effects of α-tocopherol and mannitol in both circulatory shock and cerebral ischaemia injury in rat heatstroke", Clinical and Experimental Pharmacology and Physiology, vol. 30, No. 10, Oct. 2003, pp. 745-751.
Bassareo, Valentina, et al., "Differential expression of Motivational stimulus properties by dopamine in nucleus accumbens shell versus core and prefrontal cortex", Journal of Neuroscience, vol. 22, No. 11, Jun. 1, 2002, pp. 4709-4719.
Wang, Nien-Lu, et al., "Shengmai San, a Chinese herbal medicine protects against rat heat stroke by reducing inflammatory cytokines and nitric oxide formation", Journal of Pharmacological Sciences, vol. 98, No. 1, May 2005, pp. 1-7.

* cited by examiner

*Primary Examiner* — Christopher R. Tate
(74) *Attorney, Agent, or Firm* — Hoxie & Associates LLC

(57) ABSTRACT

The invention relates to the use of cacao polyphenols for preventing or curing a prostate hyperplasia, to a cacao polyphenol extract which also comprises, in particular lipids and/or xanthines, and to the applications of said extract in food and pharmaceutical products for treating a prostate cancer, cognitive disorders, oxidative stress and cholesterol.

6 Claims, 54 Drawing Sheets

Figure 12

Chromatogram of the Cameroon polyphenol extract

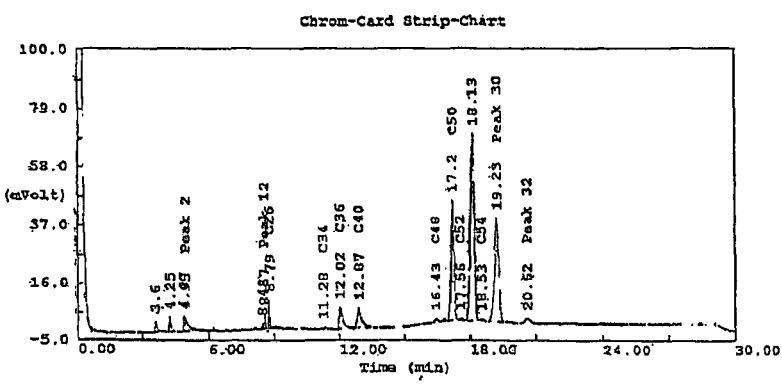

Chrom-Card Report

Method Name : TRIGLY

Company Name : BARRY-CALLEBAUT
Method File : HYDRO.MTH

Sample ID : polyextract
Analysis Type : UnkNown (Area)
Chromatogram : C:\WCC\DATA\CHROMAT2\EPB.DAT Channel : Reprocessing H2 / DBL6
Calc. Method : Area %

| Peak no. (#) | Retention time (min) | Area % (%) | Area (.1*uV*sec) | Type of peak |
|---|---|---|---|---|
| 1 | 3.60 | 1.030 | 229117 | Resolved |
| 2 | 4.25 | 1.088 | 240761 | Fused |
| 3 | 4.87 | 1.204 | 266847 | Fused |
| 4 | 4.95 | 1.687 | 373400 | Fused |
| 5 | 8.48 | *0.262 | 57953 | Fused |
| 6 | 8.57 | 0.830 | 184287 | Fused |
| 7 | 8.79 | 1.796 | 397355 | Fused |
| 8 | 11.28 | 0.237 | 52563 | Resolved |
| 9 | 12.02 | 3.469 | 768016 | Resolved |
| 10 | 12.87 | 4.371 | 967690 | Fused |
| 11 | 16.43 | 0.595 | 131780 | Resolved |
| 12 | 17.20 | 17.774 | 3934864 | Fused |
| 13 | 17.56 | 0.320 | 70740 | Fused |
| 14 | 18.13 | 38.652 | 8556976 | Fused |
| 15 | 18.53 | 0.315 | 69694 | Fused |
| 16 | 19.23 | 24.929 | 5518814 | Resolved |
| 17 | 20.62 | 1.422 | 314717 | Resolved |
| | | | 22138480 | |

\* The crossed out peaks are to be ignored

Chromatogram of the Ivory Coast polyphenol extract

* The crossed out peaks are to be ignored

Hematological analyses performed 28 days after CPE administration at doses of 50, 200 and 800 mg/kg

- Male rats:

A

| Group | Red cells (/mm³) | Hemoglobin (g%) | Hematocrite (%) | Mean globular volume (µ3) | White cells (/mm³) | Polynuclear Neutrophils (/mm³) | Polynuclear Eosinophils (/mm³) | Polynuclear Basophils (/mm³) | Lymphocytes (/mm³) | Monocytes (/mm³) | Platelets (/mm³) |
|---|---|---|---|---|---|---|---|---|---|---|---|
| Vehicle | 6,45.10⁶ ± 0,30.10⁶ | 12,23 ± 0,38 | 56,8 ± 1,6 | 88,3 ± 1,8 | 1713,3 ± 268,9 | 243,3 ± 83,6 | 0,0 ± 0,0 | 36,7 ± 11,8 | 1410,0 ± 185,7 | 23,7 ± 10,2 | 754667 ± 51778 |
| CPE FaD 50 mg/kg | 6,58.10⁶ ± 0,26.10⁶ | 12,47 ± 0,49 | 58,5 ± 2,4 | 89,0 ± 0,0 | 1212,7 ± 238,2 | 198,3 ± 44,9 | 0,0 ± 0,0 | 0,0 ± 0,0 | 996,7 ± 224,9 | 17,0 ± 9,3 | 713667 ± 14222 |
| CPE DI 200 mg/kg | 6,42.10⁶ ± 0,13.10⁶ | 12,37 ± 0,24 | 58,2 ± 1,1 | 90,3 ± 1,1 | 1876,7 ± 548,9 | 317,3 ± 148,4 | 0,0 ± 0,0 | 9,0 ± 12,0 | 1516,3 ± 375,1 | 34,0 ± 22,7 | 711667 ± 67778 |
| CPE FoD 800 mg/kg | 6,50.10⁶ ± 0,22.10⁶ | 12,40 ± 0,44 | 58,9 ± 2,2 | 90,6 ± 0,9 | 1171,2 ± 658,6 | 198,8 ± 56,2 | 1,4 ± 1,7 | 11,8 ± 6,2 | 935,4 ± 604,7 | 24,2 ± 15,4 | 750400 ± 50880 |
| Statistical Analysis | NS | NS | NS | NS | NS | NS | NS | NS (T) | NS | NS | NS |

Figure 16

Hematological analyses performed 28 days after CPE administration at doses of 50, 200 and 800 mg/kg

- Female rats:

| Group | Red cells (/mm³) | Hemoglobin (g%) | Hematocrite (%) | Mean globular volume (µ³) | White cells (/mm³) | Polynuclear ||| Lymphocytes (/mm³) | Monocytes (/mm³) | Platelets (/mm³) |
|---|---|---|---|---|---|---|---|---|---|---|---|
| | | | | | | Neutrophils (/mm³) | Eosinophils (/mm³) | Basophils (/mm³) | | | |
| Vehicle | 6,02.10⁶ ± 0,16.10⁶ | 11,50 ± 0,20 | 54,5 ± 0,8 | 90,3 ± 1,1 | 714,0 ± 230,7 | 169,3 ± 20,9 | 31,0 ± 20,7 | 22,0 ± 8,7 | 452,7 ± 249,6 | 39,3 ± 2,9 | 535533 ± 286222 |
| CPE FoD 50 mg/kg | 6,18.10⁶ ± 0,24.10⁶ | 11,87 ± 0,42 | 55,7 ± 2,2 | 90,0 ± 0,0 | 1084,3 ± 237,1 | 165,0 ± 110,7 | 0,0 ± 0,0 | 10,7 ± 2,2 | 879,3 ± 114,4 | 29,3 ± 9,1 | 719333 ± 58444 |
| CPE DI 200 mg/kg | 6,15.10⁶ ± 0,89.10⁶ | 11,67 ± 0,18 | 55,1 ± 0,8 | 89,3 ± 1,8 | 873,3 ± 127,6 | 146,0 ± 29,3 | 0,0 ± 0,0 | 19,7 ± 7,1 | 673,7 ± 185,1 | 33,7 ± 32,2 | 509333 ± 217556 |
| CPE FoD 800 mg/kg | 6,73.10⁶ ± 0,51.10⁶ | 12,23 ± 0,81 | 59,6 ± 3,7 | 88,7 ± 1,9 | 1502,2 ± 467,1 | 393,3 ± 338,4 | 0,0 ± 0,0 | 14,8 ± 4,6 | 1059,2 ± 520,5 | 34,2 ± 32,6 | 563000 ± 207333 |
| Statistical analysis | NS (T) | NS | NS (T) | NS | NS | NS | NS | NS | NS | NS | NS |

Figure 17

Biochemical analyses performed after 28 days of administration of CPE at doses of 50, 200 and 800 mg/kg

- Male rats:

| Group | Creatinin (mg/ml) | Albumin serum (g/l) | Sodium (mEq/l) | Potassium (mEq/l) | Glycemia (g/l) | Total cholesterol (g/l) | Urea (g/l) | Total protides (g/l) | ASAT (UI/l) | ALAT (UI/l) | GGT (UI/l) | Alkaline phosphatases (UI/l) |
|---|---|---|---|---|---|---|---|---|---|---|---|---|
| Vehicle | 3,00 ± 0,00 | 10,60 ± 0,36 | 139,67 ± 0,44 | 5,40 ± 0,13 | 2,03 ± 0,18 | 0,41 ± 0,06 | 0,46 ± 0,05 | 51,10 ± 0,67 | 89,00 ± 6,67 | 46,33 ± 5,11 | 1,33 ± 0,44 | 146,33 ± 23,56 |
| CPE RaD 50 mg/kg | 4,00 ± 0,00 | 10,90 ± 0,84 | 141,33 ± 1,11 | 4,50* ± 0,07 | 1,83 ± 0,06 | 0,50 ± 0,03 | 0,35* ± 0,02 | 52,97* ± 1,36 | 101,00 ± 16,67 | 54,33 ± 14,44 | 1,33 ± 0,89 | 131,33 ± 14,44 |
| CPE DI 200 mg/kg | 4,33 ± 0,44 | 10,92 ± 0,56 | 143,00 ± 0,67 | 4,17* ± 0,09 | 1,81 ± 0,03 | 0,43 ± 0,04 | 0,28* ± 0,04 | 52,93* ± 0,29 | 103,00 ± 10,67 | 46,33 ± 2,44 | 2,00 ± 0,67 | 161,33 ± 7,11 |
| CPE FoD 800 mg/kg | 3,67 ± 0,67 | 10,44 ± 0,51 | 141,67 ± 0,78 | 4,93 ± 0,34 | 2,15 ± 0,31 | 0,54 ± 0,05 | 0,31** ± 0,05 | 49,77 ± 1,03 | 111,50 ± 10,33 | 56,17 ± 10,56 | 1,33 ± 0,44 | 138,33 ± 15,78 |
| Statistical Analysis | NS | NS | NS (T) | *P=0,05 vs Vehicle (Mann-Whitney) | NS | NS (T) | *P=0,05 et **P=0,02 vs Vehicle (Mann-Whitney) | *P=0,05 vs Vehicle (Mann-Whitney) | NS (T) | NS (T) | NS | NS |

Figure 18

Biochemical analyses performed after 28 days of administration of CPE at doses of 50, 200 and 800 mg/kg

- Female rats:

| Group | Creatinin (mg/ml) | Albumin serum (g/l) | Sodium (mEq/l) | Potassium (mEq/l) | Glycemia (g/l) | Total cholesterol (g/l) | Urea (g/l) | Total protides (g/l) | ASAT (UI/l) | ALAT (UI/l) | GGT (UI/l) | Alkaline phosphatases (UI/l) |
|---|---|---|---|---|---|---|---|---|---|---|---|---|
| Vehicle | 4,00 ± 0,67 | 11,96 ± 0,92 | 140,33 ± 0,89 | 4,03 ± 0,29 | 1,67 ± 0,16 | 0,46 ± 0,09 | 0,47 ± 0,05 | 55,80 ± 1,40 | 78,67 ± 6,89 | 39,67 ± 3,11 | 1,33 ± 0,44 | 66,33 ± 7,11 |
| CPE FaD 50 mg/kg | 5,67 ± 1,11 | 13,85 ± 0,80 | 143,33 ± 1,11 | 3,40 ± 0,13 | 1,81 ± 0,11 | 0,53 ± 0,03 | 0,41 ± 0,07 | 59,00 ± 3,00 | 77,67 ± 3,56 | 42,00 ± 6,00 | 1,33 ± 0,44 | 97,67 ± 6,89 |
| CPE DI 200 mg/kg | 5,33 ± 0,44 | 13,59 ± 1,06 | 143,67 ± 0,44 | 3,90 ± 0,40 | 1,83 ± 0,09 | 0,69 ± 0,08 | 0,32 ± 0,03 | 60,20 ± 1,73 | 86,67 ± 5,78 | 48,67 ± 5,11 | 1,33 ± 0,44 | 78,00 ± 13,33 |
| CPE FoD 800 mg/kg | 4,33 ± 1,00 | 11,76 ± 0,67 | 143,00 ± 1,67 | 4,02 ± 0,28 | 1,83 ± 0,18 | 0,64 ± 0,08 | 0,36 ± 0,05 | 55,62 ± 1,92 | 133,00* ± 35,33 P=0,02 vs Vehicle (Mann-Whitney) | 55,67* ± 5,67 P=0,02 vs Vehicle (Mann-Whitney) | 1,83 ± 1,11 | 91,00 ± 16,00 |
| Statistical analysis | NS | NS (T) | NS | NS | NS | NS (T) | NS (T) | NS | | | NS | NS |

Figure 19

A ▶ Weight of the liver, kidneys, spleen and thymus after 28 days of administration of CPE at doses of 50, 200 and 800 mg/kg

- Male rats:

| Group | Liver (g/kg PC) | Kidneys (g/kg PC) | Spleen (g/kg PC) | Thymus (g/kg PC) |
|---|---|---|---|---|
| Vehicle | 37,72 ± 2,57 | 7,99 ± 0,89 | 2,25 ± 0,16 | 2,14 ± 0,25 |
| CPE FaD 50 mg/kg | 37,69 ± 2,24 | 8,58 ± 0,66 | 2,72 ± 0,19 | 2,60 ± 0,17 |
| CPE DI 200 mg/kg | 35,41 ± 2,85 | 7,86 ± 0,69 | 2,55 ± 0,16 | 2,21 ± 0,10 |
| CPE FoD 800 mg/kg | 31,88 ± 2,43 | 8,21 ± 0,31 | 1,85* ± 0,14 | 1,35* ± 0,14 |
| Statistical Analysis | NS (T) | NS | * P=0,07 vs Vehicle and P=0,02 vs FaD and DI (Mann-Whitney) | * P=0,02 vs Vehicle, vs FaD and vs DI (Mann-Whitney) |

Weight of the liver, kidneys, spleen and thymus after 28 days of administration of CPE at doses of 50, 200 and 800 mg/kg

- Female rats:

| Group | Liver (g/kg PC) | Kidneys (g/kg PC) | Spleen (g/kg PC) | Thymus (g/kg PC) |
|---|---|---|---|---|
| Vehicle | 45,02 ± 1,88 | 8,84 ± 0,70 | 2,94 ± 0,24 | 3,13 ± 0,04 |
| CPE FaD 50 mg/kg | 40,66 ± 3,79 | 9,27 ± 0,41 | 3,23 ± 0,29 | 3,40 ± 0,16 |
| CPE DI 200 mg/kg | 37,78 ± 1,92 | 8,16 ± 0,41 | 3,09 ± 0,15 | 2,93 ± 0,37 |
| CPE FoD 800 mg/kg | 33,72 ± 4,27 | 8,18 ± 0,34 | 2,05* ± 0,29 | 1,83* ± 0,20 |
| Statistical Analysis | NS (T) | NS | * $P=0,02$ vs Vehicle, vs FaD and vs DI (Mann-Whitney) | * $P=0,02$ vs Vehicle, vs FaD and vs DI (Mann-Whitney) |

Figure 21

A) Hematological analyses performed 15 days after the final administration of CPE at doses of 50, 200 and 800 mg/kg

- Male rats:

| Group | Red cells (/mm³) | Hemoglobin (g%) | Hematocrite (%) | Mean gobular volume (µ³) | White cells (/mm³) | Polynuclear Neutrophils (/mm³) | Polynuclear Eosinophils (/mm³) | Basophils (/mm³) | Lymphocytes (/mm³) | Monocytes (/mm³) | Platelets (/mm³) |
|---|---|---|---|---|---|---|---|---|---|---|---|
| Vehicle | 7,05.10⁶ ± 0,64.10⁶ | 12,23 ± 0,29 | 56,7 ± 0,8 | 80,3 ± 0,4 | 1583,3 ± 355,6 | 213,3 ± 23,6 | 0,0 ± 0,0 | 15,7 ± 3,8 | 1322,3 ± 321,6 | 31,7 ± 7,1 | 836000 ± 37333 |
| CPE FaD 50 mg/kg | 6,93.10⁶ ± 0,10.10⁶ | 12,17 ± 0,29 | 56,9 ± 1,3 | 82,0 ± 1,3 | 1730,0 ± 113,3 | 322,0 ± 87,3 | 0,0 ± 0,0 | 5,7 ± 7,6 | 1367,3 ± 61,6 | 35,0 ± 12,7 | 684667 ± 78444 |
| CPE DI 200 mg/kg | 6,64.10⁶ ± 0,50.10⁶ | 12,30 ± 0,40 | 57,5 ± 2,8 | 86,5 ± 2,5 | 1955,0 ± 275,0 | 288,0 ± 2,0 | 0,0 ± 0,0 | 11,0 ± 11,0 | 1625,5 ± 247,5 | 31,0 ± 14,0 | 831000 ± 44000 |
| CPE FoD Sat 800 mg/kg | 6,59.10⁶ ± 0,15.10⁶ | 12,13 ± 0,27 | 56,5 ± 1,4 | 85,7* ± 1,7 | 1491,7 ± 664,4 | 354,0 ± 163,3 | 0,7 ± 1,1 | 21,2 ± 14,5 | 1080,8 ± 544,2 | 35,3 ± 20,3 | 735333 ± 50000 |
| Statistical Analysis | NS | NS | NS | *P=0,020 vs Vehicle and P=0,039 vs FaD (Mann-Whitney) | NS | NS | NS | NS | NS | NS | NS (T) |

Figure 22

Hematological analyses performed 15 days after the final administration of CPE at doses of 50, 200 and 800 mg/kg

- Female rats:

| Group | Red cells (/mm³) | Hemoglobin (g%) | Hematocrite (%) | Mean globular volume (µ³) | White cells (/mm³) | Polynuclear Neutrophils (/mm³) | Eosinophils (/mm³) | Basophils (/mm³) | Lymphocytes (/mm³) | Monocytes (/mm³) | Platelets (/mm³) |
|---|---|---|---|---|---|---|---|---|---|---|---|
| Vehicle | 6,58.10⁶ ± 0,21.10⁶ | 12,07 ± 0,24 | 56,7 ± 1,6 | 86,0 ± 2,0 | 1929,3 ± 1733,8 | 641,7 ± 719,6 | 1,0 ± 1,3 | 39,7 ± 34,2 | 1181,3 ± 933,8 | 65,3 ± 47,1 | 684000 ± 128000 |
| CPE FaD 50 mg/kg | 6,31.10⁶ ± 0,20.10⁶ | 11,83 ± 0,38 | 54,1 ± 2,5 | 85,7 ± 1,6 | 949,0 ± 314,0 | 144,0 ± 46,0 | 0,0 ± 0,0 | 9,3 ± 3,1 | 745,0 ± 251,3 | 50,3 ± 23,6 | 713333 ± 59111 |
| CPE DI 200 mg/kg | 6,41.10⁶ ± 0,30.10⁶ | 11,90 ± 0,47 | 54,9 ± 2,6 | 86,0 ± 1,3 | 787,0 ± 210,7 | 140,7 ± 41,6 | 0,0 ± 0,0 | 4,7 ± 3,1 | 629,0 ± 202,7 | 12,3 ± 3,8 | 688000 ± 8667 |
| CPE FoD Sat 800 mg/kg | 6,28.10⁶ ± 0,22.10⁶ | 12,25 ± 0,22 | 56,6 ± 1,1 | 90,2* ± 1,6 | 2170,0 ± 120,0 | 282,2 ± 44,8 | 0,0 ± 0,0 | 28,8 ± 14,8 | 1762,0 ± 124,3 | 96,8 ± 33,8 | 741333 ± 54000 |
| Statistical Analysis | NS | NS | NS | *P=0,028 vs FaD and DI (Mann-Whitney) | NS (T) | NS | NS | NS | NS (T) | NS (T) | NS |

Figure 23

Biochemical analyses performed 15 days after the final administration of CPE at doses of 50, 200 and 800 mg/kg

- Male rats:

A

| Group | Creatinin (mg/ml) | Albumin serum (g/l) | Sodium (mEq/l) | Potassium (mEq/l) | Glycemia (g/l) | Total cholesterol (g/l) | Urea (g/l) | Total protides (g/l) | ASAT (UI/l) | ALAT (UI/l) | GGT (UI/l) | Alkaline phosphatases (UI/l) |
|---|---|---|---|---|---|---|---|---|---|---|---|---|
| Vehicle | 3,67 ± 0,44 | 10,10 ± 0,78 | 138,00 ± 0,00 | 4,70 ± 0,27 | 1,93 ± 0,12 | 0,40 ± 0,09 | 0,48 ± 0,02 | 52,50 ± 1,13 | 93,67 ± 4,89 | 49,00 ± 4,67 | 2,33 ± 0,44 | 119,00 ± 25,33 |
| CPE FaD 50 mg/kg | 4,00 ± 0,00 | 11,61 ± 1,13 | 139,33 ± 1,11 | 4,03* ± 0,22 | 2,26 ± 0,04 | 0,47 ± 0,14 | 0,46 ± 0,01 | 53,63 ± 1,18 | 103,33 ± 30,44 | 73,00 ± 34,00 | 1,33 ± 0,44 | 118,67 ± 14,89 |
| CPE D1 200 mg/kg | 4,00 ± 0,00 | 11,40 ± 0,09 | 140,50 ± 0,50 | 4,10 ± 0,20 | 2,29 ± 0,29 | 0,67 ± 0,02 | 0,47 ± 0,06 | 54,60 ± 0,90 | 92,00 ± 13,00 | 49,50 ± 3,50 | 2,50 ± 0,50 | 111,50 ± 16,50 |
| CPE FoD Sat 800 mg/kg | 3,83 ± 0,56 | 10,80 ± 0,19 | 138,83 ± 0,83 | 4,90** ± 0,27 | 2,34 ± 0,31 | 0,43 ± 0,07 | 0,52 ± 0,05 | 51,00 ± 1,23 | 86,00 ± 2,00 | 43,00 ± 6,00 | 2,33 ± 0,78 | 102,50 ± 14,00 |
| Statistical Analysis | NS | NS | NS | * $P=0,049$ vs Vehicle and $P=0,020$ vs FoD Sat ** $P=0,049$ vs D1 (Mann-Whitney) | NS | NS | NS | NS (T) | NS | NS | NS | NS |

Figure 24

Biochemical analyses performed 15 days after the final administration of CPE at doses of 50, 200 and 800 mg/kg

- Female rats:

| Group | Creatinin (mg/ml) | Albumin serum (g/l) | Sodium (mEq/l) | Potassium (mEq/l) | Glycemia (g/l) | Total cholesterol (g/l) | Urea (g/l) | Total protides (g/l) | ASAT (UI/l) | ALAT (UI/l) | GGT (UI/l) | Alkaline phosphatases (UI/l) |
|---|---|---|---|---|---|---|---|---|---|---|---|---|
| Vehicle | 5,00 ± 0,67 | 12,72 ± 1,50 | 140,00 ± 0,67 | 4,43 ± 0,11 | 1,82 ± 0,01 | 0,50 ± 0,04 | 0,62 ± 0,04 | 58,80 ± 2,27 | 95,67 ± 22,89 | 41,33 ± 0,44 | 2,00 ± 1,33 | 76,00 ± 24,00 |
| CPE FaD 50 mg/kg | 4,67 ± 0,44 | 12,65 ± 2,42 | 140,00 ± 0,00 | 3,80* ± 0,13 | 2,18 ± 0,07 | 0,57 ± 0,13 | 0,57 ± 0,02 | 58,93 ± 4,04 | 84,67 ± 6,22 | 44,00 ± 6,00 | 1,67 ± 0,44 | 84,67 ± 18,89 |
| CPE DI 200 mg/kg | 5,00 ± 0,67 | 13,84 ± 0,56 | 141,67 ± 0,89 | 3,20** ± 0,07 | 1,89 ± 0,07 | 0,59 ± 0,13 | 0,55 ± 0,04 | 58,90 ± 1,13 | 85,00 ± 5,33 | 47,67 ± 2,22 | 1,67 ± 0,44 | 67,00 ± 11,33 |
| CPE FoD 800 mg/kg | 4,33 ± 0,56 | 12,02 ± 0,59 | 140,50 ± 0,67 | 3,87*** ± 0,20 | 1,90 ± 0,11 | 0,49 ± 0,05 | 0,52 ± 0,05 | 51,85* ± 1,97 | 77,83 ± 9,44 | 38,17 ± 4,89 | 2,17 ± 0,56 | 60,33 ± 6,11 |
| Statistical Analysis | NS | NS | NS | *P=0,049 vs Vehicle, **P=0,049 vs Vehicle and FaD, ***P=0,020 vs Vehicle and DI (Mann-Whitney) | NS (T) | NS | NS | *P=0,020 vs Vehicle, FaD and DI (Mann-Whitney) | NS | NS | NS | NS |

Figure 25

Weight of the liver, kidneys, spleen and thymus 15 days after the final administration of CPE at doses of 50, 200 and 800 mg/kg

- Male rats:

| Group | Liver (g/kg PC) | Kidneys (g/kg PC) | Spleen (g/kg PC) | Thymus (g/kg PC) |
|---|---|---|---|---|
| Vehicle | 34,56 ± 1,73 | 8,02 ± 0,29 | 2,08 ± 0,06 | 2,23 ± 0,34 |
| CPE FnD 50 mg/kg | 35,10 ± 1,06 | 8,67 ± 0,34 | 2,05 ± 0,16 | 2,24 ± 0,32 |
| CPE DI 200 mg/kg | 36,52 ± 0,16 | 8,24 ± 0,24 | 2,33 ± 0,25 | 2,16 ± 0,18 |
| CPE FoD 800 mg/kg | 34,42 ± 2,57 | 8,47 ± 0,49 | 2,28 ± 0,15 | 2,20 ± 0,27 |
| Statistic Analysis | NS | NS | NS | NS |

Figure 26

A) Weight of the liver, kidneys, spleen and thymus 15 days after the final administration of CPE at doses of 50, 200 and 800 mg/kg

- Female rats:

| Group | Liver (g/kg PC) | Kidneys (g/kg PC) | Spleen (g/kg PC) | Thymus (g/kg PC) |
|---|---|---|---|---|
| Vehicle | 38,53 ± 3,32 | 9,94 ± 0,66 | 2,63 ± 0,36 | 2,53 ± 0,40 |
| CPE FaD 50 mg/kg | 39,12 ± 3,44 | 9,74 ± 0,52 | 2,50 ± 0,01 | 2,47 ± 0,23 |
| CPE DI 200 mg/kg | 39,11 ± 0,38 | 8,64 ± 0,38 | 2,41 ± 0,30 | 2,43 ± 0,46 |
| CPE FoD 800 mg/kg | 37,06 ± 3,22 | 9,00 ± 0,52 | 2,96 ± 0,26 | 2,64 ± 0,31 |
| Statistical Analysis | NS | NS (T) | NS (T) | NS |

Figure 27

| Healthy line (RWEP-1) cultured in M1 | Healthy line (RWEP-1) cultured in M2 | Healthy line (RWEP-1) cultured in M3 |

| Tumor line (22Rv1) cultured in M1 | Tumor line (22Rv1) cultured in M2 | Tumor line (22Rv1) cultured in M3 |

Figure 36
Co-culture of healthy and tumor lines in M1
Co-culture of healthy and tumor lines in M2
Co-culture of healthy and tumor lines in M3
a
b
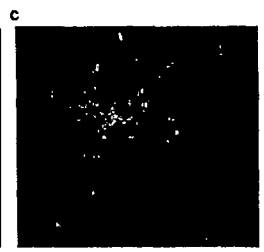
c Figure 39
39a
39b
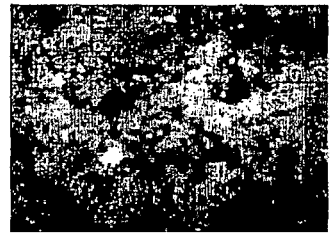
39c
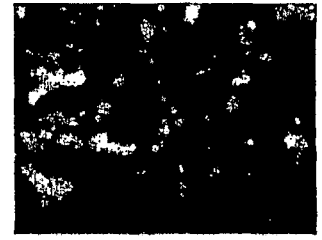
39d
39e
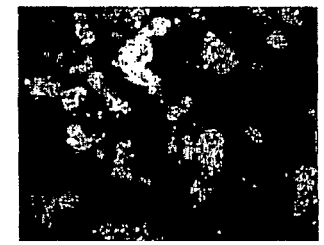

APPENDICES

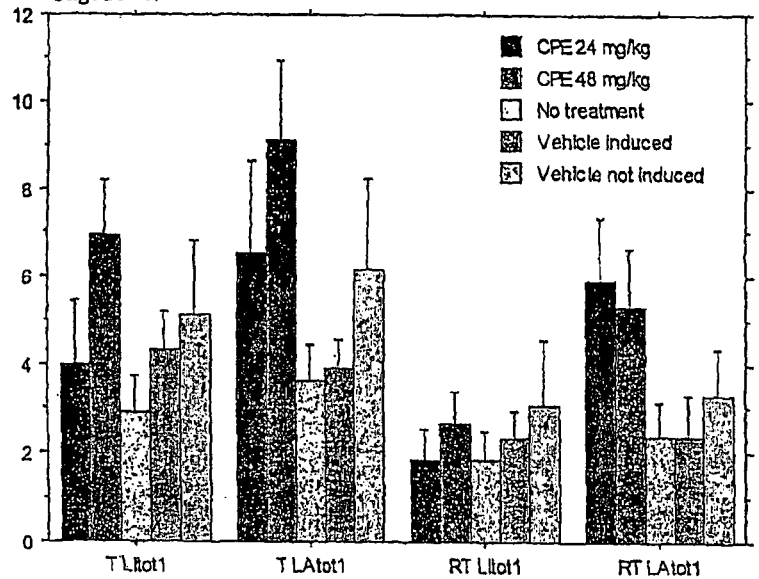
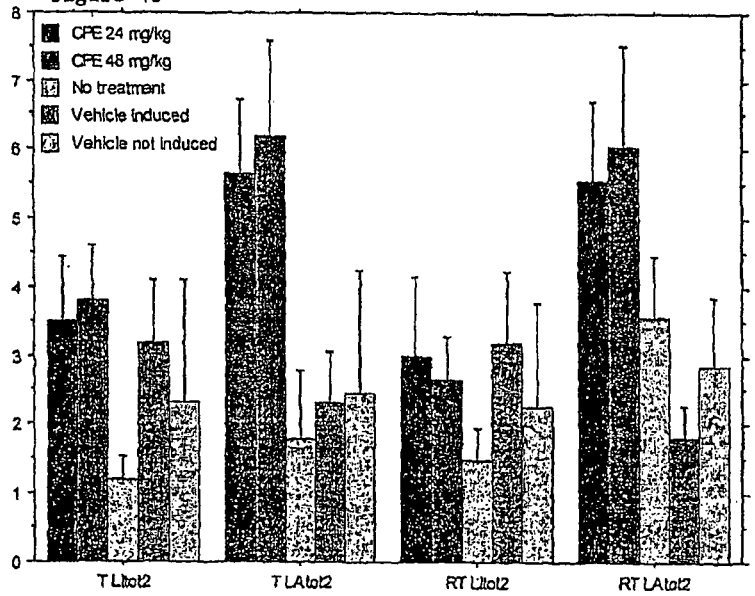

APPENDICES

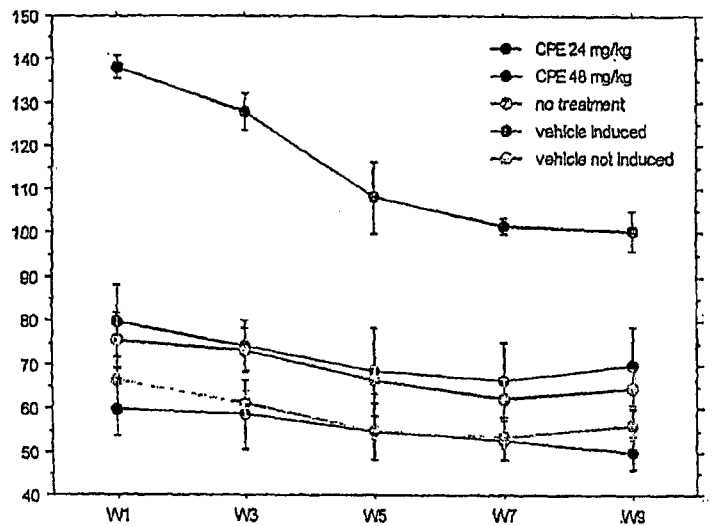
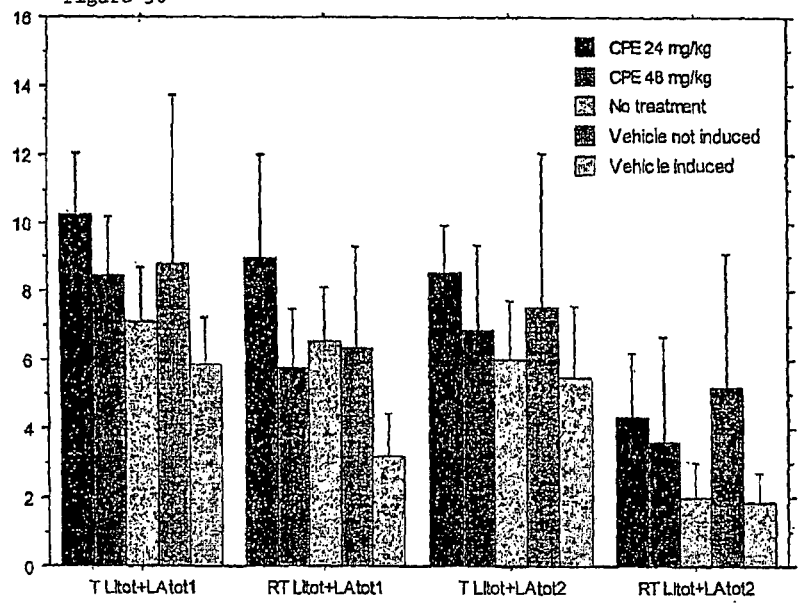

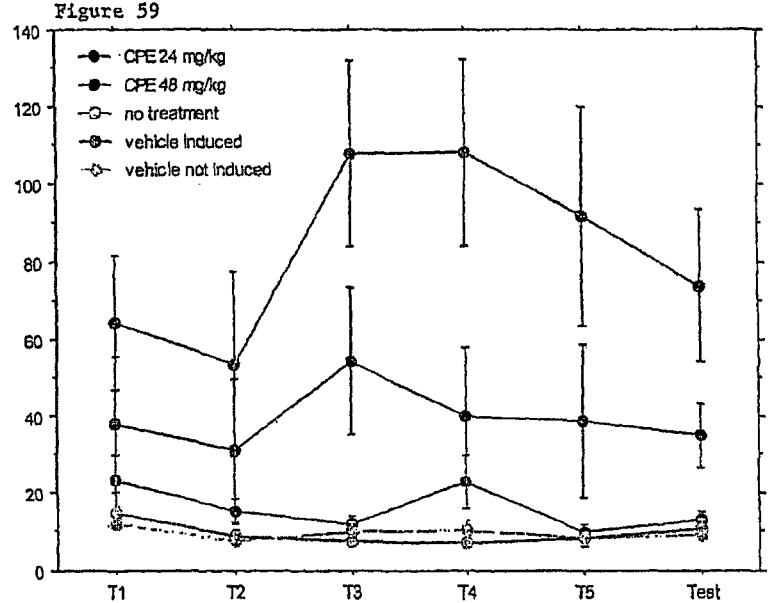
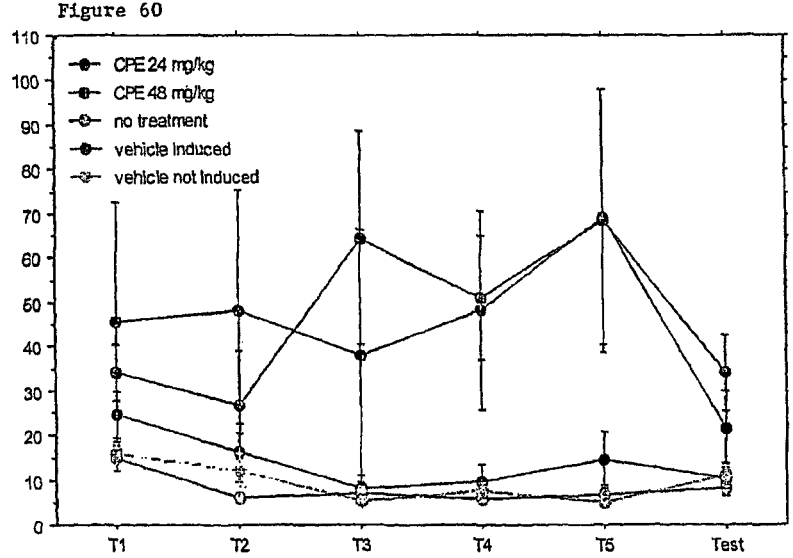

USE OF COCOA POLYPHENOLS FOR TREATING A PROSTATE HYPERPLASIA, A SPECIFIC COCOA EXTRACT AND APPLICATIONS

CROSS-REFERENCE TO RELATED APPLICATIONS

This application is a 371 U.S. National Phase of International Application No. PCT/FR2006/000204, filed Jan. 30, 2006, claiming priority to U.S. Provisional Application No. 60/647,404, filed Jan. 28, 2005, and U.S. Provisional Application No. 60/739,930, filed Nov. 28, 2005, the contents of each of which is incorporated herein by reference.

The present invention relates to the use of cocoa polyphenols for treating prostate hyperplasia, to a specific cocoa extract and to the uses of said extract in the pharmaceutical and food sectors.

The invention more specifically relates to the use of cocoa polyphenols for preventively or curatively treating prostate hyperplasia, to a cocoa polyphenol extract also comprising, especially, lipids and/or xanthines, whose use proves to be particularly effective against prostate cancer, against cognitive disorders, in particular by modulating the level of dopamine expression, and against oxidative stress and cholesterol.

Prostate hyperplasia is a condition characterized by an increase in the volume of the prostate. This increase in volume may result from a simple benign hyperplasia of the prostate or may correspond to a prostate cancer.

Benign hyperplasia of the prostate (BHP), also known as prostate adenoma or benign hypertrophy of the prostate, is characterized by hyperplasia of the stroma cells and of the prostate epithelium.

BHP affects about 50% of men over the age of 50. In certain cases, it may result in functional disorders of the lower urinary apparatus, in particular miction disorders (obstruction or irritation). The treatments currently available are phytotherapy, the administration of alpha-blockers or of 5-alpha-reductase inhibitor and surgical treatment. It is currently considered that a 40 year-old man has a likelihood of about 37% of undergoing BHP surgery if he survives to the age of 80.

The investigations conducted by the inventors have made it possible to demonstrate that the administration of a composition based on cocoa poly-phenols makes it possible to treat prostate hyperplasia in general and more particularly BHP.

According to a first aspect, the invention is thus directed toward the use of cocoa polyphenols for the preparation of a medicament for treating prostate hyperplasia.

The term "prostate hyperplasia" means benign hyperplasia of the prostate and also prostate hyper-plasia resulting from a prostate cancer.

The treatments according to the invention may be aimed at relieving the symptoms of the hyperplasia, or may be for preventive or curative purposes. Examples 1 and 2 demonstrate the activity of a cocoa polyphenol extract in a preventive and curative treatment of hyperplasia induced chemically in rats.

The invention also proposes therapeutic treatment methods comprising the administration to a patient of a composition based on cocoa polyphenols combined with pharmaceutically acceptable excipients in order to prevent/relieve the symptoms/cure a prostate hyperplasia, whether it is benign or results from an already diagnosed prostate cancer. Advantageously, the cocoa polyphenols introduced into the composition are derived from a cocoa polyphenol extract.

The term "cocoa polyphenol extract" means an extract obtained by extracting cocoa beans or products derived from cocoa beans, comprising cocoa polyphenols.

The medicament obtained may be administered alone or in combination with other medicaments such as pelvic decongestants, alpha-blockers and/or 5-alpha-reductase inhibitors. The mode of administration may be systemic or topical, preferably via the oral, parenteral (intravenous or subcutaneous), rectal or topical route and in the form, for example, of simple or sugar-coated tablets, gel capsules, creams, ointments, suppositories, injectable solutions or drinkable suspensions. Finally, the medicament may be prescribed as a complement to a surgical treatment.

The dosage may be adapted according to the nature and severity of the complaint, the desired therapeutical aim, the administration route and also the sex and age of the patient.

By way of example, the medicament may be administered at a dose of from 15 to 30 mg/kg/day orally, for a preventive treatment, and at a dose of from 40 to 60 mg/kg/day orally, when the treatment is curative. These dosages may advantageously be administered, where appropriate, in several intakes.

Advantageously, the cocoa polyphenol extract used in the medicament will have the following composition:
- 20% to 50% by mass as epicatechin equivalent of polyphenols, including 55% to 80% flavonoids,
- 3% to 15% by mass of lipids, including 1% to 15% β-sitosterol,
- 5% to 20% by mass of xanthines.

The extract according to the invention may be used in crude or purified form.

According to a second aspect of the invention, it is also directed toward said cocoa polyphenol extract described above. Specifically, this extract is particularly effective for treating pathologies other than hyperplasia.

Measurement of the polyphenol content was performed according to the Folin-Ciocalteu method.

The cocoa extract according to the invention has a high content of polyphenols, especially of polyphenols with high antioxidant activity such as flavonoids, more especially flavonoids such as catechin, epicatechin and derivatives thereof. Advantageously, the extract according to the invention comprises from 10% to 30% epicatechin. In addition, the extract according to the invention is particularly rich in oligomeric polyphenols composed of 1 to 6 monomers.

The term "xanthines" mainly means caffeine and theobromine.

Examples of extracts are given in example 3, with reference to FIGS. 12 and 13.

Such extracts may be obtained from beans of various origins, preferably beans originating from Cameroon, Tanzania or the Ivory Coast.

Advantageously, the cocoa extract is obtained from unfermented, dried and then optionally rehumidified beans. The resulting beans are then cleaned and hulled in order to obtain the green seed. Extraction in an ethanol-water mixture (70/30) is then performed for about 24 hours with stirring, with a cocoa/solvent ratio of about ½ to ¼. The liquor obtained is then filtered, rinsed, concentrated and evaporated to dryness. It is imperative that no defatting step be performed throughout the process.

The extract according to the invention thus contains β-sitosterol, xanthines and also polyphenols. The presence of β-sitosterol improves the assimilation of the polyphenols by the body. Moreover, the inventors' investigations have demonstrated that, contrary to what was suggested in the prior art, the presence of xanthines with polyphenols does not harm the polyphenol activity and, on the contrary, affords advantageous effects in certain applications, in particular cognitive applications.

According to a third aspect, the cocoa polyphenol extract is used for treating prostate cancer.

Prostate cancer, an age-dependent malignant tumor, is the second most common cause of death by cancer among males in the United States and in western Europe. Although the etiology of this cancer is unknown, several risk factors including age, race, environment and diet have been identified. Other risk factors include polymorphic repetitions of the androgen receptor gene and high concentrations of circulating androgens. The importance of testosterone in the development of prostate cancer is emphasized by the discovery that prostate cancer rarely occurs in castrated males or in males who are deficient in 5α-reductase, the enzyme responsible for converting testosterone into its active metabolite, dihydrotestosterone. Several studies have identified various dietary substances with antioxidant properties and an inhibitory effect on the development and/or progress of prostate cancer. Among these substances, polyphenols are the most abundant natural antioxidants, and are found in fruits, drinks (fruit juices, wine, tea, coffee, chocolate and beer) and to a lesser extent in vegetables, pulses and cereals. They play a role in various diseases associated with oxidative stress such as cancer, cardiovascular diseases and inflammation. Polyphenols are reductive agents and, in combination with other dietary reductive agents, such as vitamin C, vitamin E and carotenoids, they protect the body tissues against oxidative stress. The large diversity of their structures makes them different from other antioxidants and has a bearing on their biological properties: bioavailability, antioxidant activity, specific interactions with cell receptors and enzymes, etc. Polyphenols are divided into subgroups such as isoflavones, flavonoids and lignans. It has recently been discovered that several polyphenols extracted from various plants are powerful angiogenesis inhibitors.

Cocoa beans have been identified as a rich source of polyphenols. Cocoa polyphenols modulate the immune functions and platelet function, reduce the oxidation of low-density lipoproteins (LDL), inhibit the growth of human cancer cells in vitro and of experimental tumors in vivo on models of multiorgan carcinogenesis in rats.

According to a fourth aspect, the invention is thus directed toward the use of a cocoa polyphenol extract as described above, for the preparation of a medicament for preventing and/or treating prostate cancer.

The invention is also directed toward the use of a cocoa polyphenol extract as described above, for the preparation of a medicament for relieving the symptoms of prostate cancer.

According to one advantageous aspect, the invention is also directed toward the use of a cocoa polyphenol extract as described above, for selectively inhibiting the proliferation of human prostate tumor cells, without inhibiting the healthy human prostate cells.

Thus, the cocoa polyphenol extract of the invention makes it possible, for example, to inhibit the proliferation of the prostate cancer cells 22Rv1 and DU145, without inhibiting the healthy human prostate epithelial cells RWEP-1, "22Rv1" representing the human loco-regional prostate cancer cell line, "DU145" representing the human prostate cancer cell line derived from a metastasic site of cerebral origin and "RWEP-1" representing the healthy human prostate cell line.

The cocoa polyphenol extract of the invention makes it possible to inhibit the effects of prostate cancer induced chemically in rats, and, to the Inventors' knowledge, this is the first time that such results have been able to be obtained.

A subject of the present invention is also the use as defined above of the cocoa polyphenol extract, in which the extract is administered to a mammal at doses ranging from 15 to 60 mg/kg/day and preferably ranging from 20 to 40 mg/kg/day.

Several thousand polyphenols have been identified in plants, and especially in edible plants, and also in drinks. Their role in preventing cancer, osteoporosis or coronary diseases is currently under study. Their antioxidant and antiinflammatory effects have been proven by several in vitro and in vivo studies. Flavonoids, the most important class of polyphenols, are found in many fruits, vegetables and drinks.

Many epidemiological studies have shown that the consumption of fruit and vegetables is inversely related to the occurrence of cardiovascular diseases and death by degenerative diseases.

The polyphenols contained in food have protective and beneficial biological effects on human beings in the case of oxidative stress. An oxidative stress in rats exposed to a heart attack induces an overproduction of free radicals in circulation, which harm the memory and learning performances.

An imbalance between the formation of reactive oxidative species and antioxidant defense is known as oxidative stress. Reactive oxidative species are free radicals including a superoxidizing anion, hydrogen peroxide and a hydroxyl radical, which are normally produced in low amounts. Under normal conditions, the body's scavengers such as superoxide dismutase and catalase metabolize these free radicals. With modern life, and under certain physiopathological conditions, free radicals increase the harmful cellular components. Polyunsaturated fatty acids, phospholipids, free cholesterol, DNA and small molecules are cell targets that reduce the number of free radicals.

According to a fifth aspect, the invention is thus directed toward the use of a cocoa polyphenol extract as described above, for the preparation of a medicament for preventing and/or treating cognitive disorders. Thus, the invention is more particularly directed toward the use as described above for improving the learning, memorization and spatial orientation capacities of a mammal.

The invention is also directed toward the use of a cocoa polyphenol extract as described above, for the preparation of a medicament for preventing the overproduction of free radicals following a heat stroke.

For cognitive applications, the mode of administration may be systemic or topical, preferably via the oral, parenteral (intravenous or subcutaneous), rectal or topical route, and in the form, for example, of simple or sugar-coated tablets, gel capsules, creams, ointments, suppositories, inhalations, injectable solutions or drinkable suspensions.

Since cognitive disorders are induced by an overproduction of free radicals, prevention of the overproduction of free radicals thus makes it possible to prevent the occurrence of said cognitive disorders.

Examples of cognitive disorders that may especially be mentioned include arterial hypotension, cerebral ischemia, neuronal damage, etc.

According to one advantageous embodiment of the invention, the medicament for preventing the over-production of free radicals is administered at a dose of from 1 mg/kg/day to 100 mg/kg/day, before the heat stroke or after the heat stroke.

According to a sixth aspect, the invention is thus directed toward the use of the cocoa polyphenol extract according to the invention for stimulating the production of dopamine.

Dopamine is a neurotransmitter belonging to the catecholamine family. In the peripheral nervous system, it has a circulatory analeptic role (stimulating the functions that ensure blood circulation). In the central nervous system, it has a stimulant overall effect. It is in particular involved in dependence phenomena, via the reward system, and in controlling motor functions. Parkinson's disease is, for example, a disease whose cause is the degeneration of a group of dopamine-producing neurons.

Increasing the level of dopamine makes it possible to maintain a deficient arterial pressure, to conserve diuresis via vasoconstriction of the renal arteries and to treat the symptoms of Parkinson's disease.

Example 11 demonstrates that the oral administration of 24 mg/kg of an extract according to the invention makes it possible to triple the level of dopamine in rats.

The invention also proposes therapeutic treatment methods comprising the administration to a patient of a composition based on a cocoa polyphenol extract according to the invention in order to stimulate the production of dopamine. The administration of this composition may in particular have the objective of preventing/relieving the symptoms of Parkinson's disease, of maintaining an arterial pressure in the case of patients with a deficiency in said arterial pressure or of conserving diuresis in the case of patients with diuresis disorders.

The medicament obtained may be administered alone or in combination with one or more other medicaments. In particular, in the context of a treatment of Parkinson's disease, the medicament may advantageously be administered in combination with L-Dopa, dopaminergic agonists or catechol-O-methyl transferase inhibitors.

The mode of administration may be systemic or topical, preferably via the oral, rectal, parenteral (intravenous or subcutaneous) or topical route and in the form of simple or sugar-coated tablets, gel capsules, creams, ointments, suppositories, inhalations, injectable solutions or drinkable suspensions.

The dosage may be adapted according to the nature and severity of the complaint, the desired therapeutic aim, the route of administration and also the sex and age of the patient.

By way of example, the medicament may be administered at a dose of from 10 to 30 mg/kg/day orally. These dosages may advantageously be administered in several intakes.

According to a final aspect, the invention is also directed towards the use of the cocoa polyphenol extract described above, for preventing oxidative stress (see example 12).

The present invention will be more fully described with the aid of the examples that follow, which are given as illustrations, with reference to the figures:

FIGS. 1 to 5, relating to the preventive treatment of hyperplasia, respectively show the progress of the experiment (FIG. 1), the weight gain (FIG. 2), the intake of food (FIG. 3) and of drink (FIG. 4) and the weight of the prostates (FIG. 5), FIGS. 6-11, relating to the curative treatment of hyperplasia, respectively show the progress of the experiment (FIG. 6), the weight gain (FIG. 7), the intake of food (FIG. 8) and of drink (FIG. 9) and the weight of the prostates (FIGS. 10-11), FIGS. 12 and 13 are chromatograms of cocoa polyphenol extracts originating, respectively, from Cameroon and from the Ivory Coast, FIGS. 14 to 27, relating to the evaluation of the toxicity of a cocoa polyphenol extract according to the invention, respectively show the weight gain of the rats (FIGS. 14 and 15) and the results of the analyses performed on the animals (FIGS. 16 to 27), FIGS. 28 and 29, relating to the determination of the $LD_{50}$ of a cocoa polyphenol extract according to the invention, respectively show the weight curves for the male and female rats, FIGS. 30 to 33, relating to prostate cancer on cell models, show the morphology of the three cell lines RWEP-1, 22Rv1 and DU145 (FIG. 30), the proliferation of the RWEP-1, 22Rv1 and DU145 cells as a function of the dose and of time (FIGS. 31 to 33), FIGS. 34 to 39, relating to prostate cancer on models of cocultures, show the cultures of a healthy line (RWEP-1) (FIGS. 34*a* to 34*c*), of a tumor line (22Rv1) (FIGS. 35*a* to 35*c*), of a coculture of healthy and tumor lines (FIGS. 36*a* to 36*c*), the results of the proliferation test via the method of release of neutral red (FIGS. 37*a* to 38*f*) and the results of immunolabeling on a coculture after treatment (FIGS. 39*a* to 39*e*), FIGS. 40 to 42, relating to the chemopreventive effect of the extract on rats, show the body weight gains of rats subjected to different treatments (FIG. 40), the consumption of food (FIG. 41) and the consumption of water (FIG. 42), FIGS. 43 to 52, relating to the effects of the extract on the development of chemo-induced tumors, show the change in body weight of the rats (FIG. 43), the consumption of food (FIG. 44), the consumption of water (FIG. 45), the activity of the rats during the TAALS tests (FIGS. 46-50) and the Morris aquatic labyrinth test (FIGS. 51-52), FIGS. 53 to 62, relating to the effects of the extract on the development of chemo-induced tumors, illustrate the change in body weight of the rats (FIG. 53), the consumption of food (FIG. 54), the consumption of water (FIG. 55), the activity of the rats during the TAALS tests (FIGS. 56-58), the Morris aquatic labyrinth test (FIGS. 59-60) and the dopamine assay (FIGS. 61 and 62), and FIGS. 63 to 66, relating to the effects of a cocoa polyphenol extract, as a preventive treatment on the development of chemo-induced prostate tumors, on the cognitive performances and on dopamine, show the results obtained on the TAALS tests (FIGS. 63 and 64), the Morris tests (FIG. 65) and the dopamine assay (FIG. 66).

EXAMPLE 1

Evaluation of the Effects of a Cocoa Polyphenol Extract as a Preventive Treatment on the Development of Prostate Hyperplasia 1. Materials and methods Animals:

48 male Wistar-Unilever rats weighing 260-270 g, under controlled conditions of temperature (22+/−2° C.), humidity (50+/−10%), under an inverted 12-hour lighting cycle (light from 08:00 h to 20:00 h), food and drink ad libitum.

Treatments:

Use of a cocoa polyphenol extract (CPE) administered daily orally at doses of 24 or 48 mg/kg for 5 weeks.

| Group | Treatment | Dose |
|---|---|---|
| Control + vehicle | Vehicle | — |
| TP + vehicle | Vehicle | — |
| TP + CPE 24 | CPE | 24 mg/kg, orally |
| TP + CPE 48 | CPE | 48 mg/kg, orally |

Progress of the Experiment (See FIG. 1):

Benign hyperplasia of the prostate is induced by daily subcutaneous injection for 3 weeks (D14 to D35) of 2 mg/rat of testosterone propionate (TP) dissolved in corn germ oil.

The monitoring of the parameters is performed by daily checking of the survival of the animals, weighing of the animals 3 times a week and daily monitoring of the intake of food and drink.

The animals are sacrificed at the end of 5 weeks after the start of the CPE treatments. The prostate is removed and weighed (3 successive weighings).

2. Results

Weight of the Animals (FIG. 2)

Treatment of the rats with CPE at 24 or 48 mg/kg made it possible to maintain a regular weight gain throughout the experiment. However, the 48 mg/kg dose more substantially limited this weight gain.

Intake of Food (FIG. 3)

Treatment of the rats with CPE at 24 or 48 mg/kg made it possible to maintain an intake of food comparable to that for the "control/vehicle" group throughout the experiment, thus limiting the decrease in food intake induced by the induction of the prostate hyperplasia observed for the "TP/Vehicle" group.

Intake of Drink (FIG. 4)

Treatment of the rats with CPE at 24 or 48 mg/kg made it possible to limit the increased intake of drink associated with the subcutaneous injections of testosterone, observed for the "TP/Vehicle" group, thus limiting the effects of the induction of the prostate hyperplasia.

Weight of the Prostates (FIG. 5)

Treatment of the rats with CPE is dose-dependent: the 24 mg/kg dose and especially the 48 mg/kg dose made it possible to limit the increase in weight of the prostate observed for the rats of the "TP/Vehicle" group that is associated with the subcutaneous injections of testosterone, thus very strongly limiting the effects of the induction of the prostate hyperplasia.

3. Conclusion

Pretreatment of the rats with CPE at 24 or 48 mg/kg made it possible to limit the effects of induction of the prostate hyperplasia in a dose-dependent manner. The best efficacy observed under the conditions of the experiment corresponds to the 48 mg/kg dose.

This 48 mg/kg dose appears, however, to be relatively high since it also limited the weight gain of the animals from the pretreatment phase onwards. Given the effects observed on the reduction of the weight of the prostates, this dose is close to a therapeutic dose.

EXAMPLE 2

Evaluation of the Effects of a Cocoa Polyphenol Extract as a Curative Treatment on the Development of Prostate Hyperplasia 1. Materials and methods Animals:

48 male Wistar-Unilever rats weighing 280-300 g, under controlled conditions of temperature (22+/−2° C.) and humidity (50+/−10%), under an inverted 12-hour lighting cycle (light from 09:00 h to 21:00 h), food and drink ad libitum.

Treatments:

Use of a cocoa polyphenol extract (CPE) administered daily orally at doses of 24 or 48 mg/kg for 2 weeks (D22 to D36).

| Group | Treatment | Dose |
|---|---|---|
| Control + vehicle | Vehicle | — |
| TP + vehicle | Vehicle | — |
| TP + CPE 24 | CPE | 24 mg/kg, orally |
| TP + CPE 48 | CPE | 48 mg/kg, orally |

Progress of the Experiment (See FIG. 6):

Benign hyperplasia of the prostate is induced by daily subcutaneous injection for 3 weeks (D15 to D36) of 2 mg/rat of testosterone propionate (TP) dissolved in corn germ oil.

Monitoring of the parameters is performed by daily checking of the survival of the animals, weighing of the animals 3 times a week and daily monitoring of the intake of food and drink.

Assay of the DHT (dihydrotestosterone) is performed according to the following protocol:
  withdrawal of 7 to 8 ml of blood from the abdominal aorta of all of the animals just before sacrifice on D36,
  recovery of 2.5 to 4.5 ml of serum and freezing at −20° C.,
  DHT assays performed by the I.R.E.M. in Paris.

The animals are sacrificed 2 weeks after the start of the treatments with CPE, immediately after taking the blood sample. The prostate is removed and weighed (3 successive weighings).

2. Results

Weight of the Animals (FIG. 7)

The mean weight of the rats of the "Control/Vehicle" group increased regularly throughout the experiment. That of the rats of the "TP/Vehicle" group increased regularly up to the 20th day of treatment and then stabilized and decreased slightly over the final 15 days of the experiment. The mean weight of the rats of the "TP/CPE 24 mg/kg" group also increased regularly up to the 20th day of treatment, then stabilized and decreased slightly over the final 15 days of the experiment, but less than that for the "TP/Vehicle" group. The mean weight of the rats of the "TP/CPE 48 mg/kg" group increased regularly up to the 20th day of treatment and then stabilized and increased again over the final 10 days of the experiment. The mean weight of the rats of the "TP/CPE 48 mg/kg" group increased more than that of the rats of the "TP/CPE 24 mg/kg" group.

Treatment of the rats with CPE at 48 mg/kg made it possible to maintain a more regular weight gain throughout the experiment.

Intake of Food (FIG. 8)

The mean intake of food for the 4 groups of "Control/Vehicle", "TP/CPE 24 mg/kg", "TP/CPE 48 mg/kg" and "TP/Vehicle" rats was identical over the first 2 weeks of the experiment, before induction of the benign hyperplasia of the prostate. The decrease observed is normal since the values correspond to the mean of the ratios between the intake of food and the weight of the animals. The animals eat more or less the same amount of the diet, but they become heavier, resulting in a decrease in this ratio. The mean intake of food for the "TP/CPE 24 mg/kg", "TP/CPE 48 mg/kg" and "TP/Vehicle" groups decreased significantly relative to the "Control/Vehicle" group after the start of induction of the prostate hyperplasia and also decreased significantly for all the groups after the start of the oral treatments, mainly for the "TP/Vehicle" group and less strongly for the 2 "TP/CPE 24 mg/kg" and especially "TP/CPE 48 mg/kg" groups. During the final week of treatment, the mean intake of food for the "TP/CPE 48 mg/kg" group increased more significantly than for the other 3 groups. (The statistical treatments have yet to be done).

Treatment of the rats with CPE at 48 mg/kg made it possible to maintain a mean intake of food closer to that of the "Control/Vehicle" group throughout the experiment, thus limiting the effects induced by the induction of the prostate hyperplasia observed in the "TP/Vehicle" group.

Intake of Drink (FIG. 9)

The mean intake of drink for the 4 groups of "Control/Vehicle", "TP/CPE 24 mg/kg", "TP/CPE 48 mg/kg" and "TP/Vehicle" rats was identical for the first 2 weeks of the experiment, with induction of benign hyperplasia of the prostate. After the start of induction of the prostate hyperplasia, the mean intake of drink for the "TP/CPE 24 mg/kg", "TP/CPE 48 mg/kg" and "TP/Vehicle" groups increased significantly relative to the "Control/Vehicle" group. The mean intake of drink for the 2 "TP/CPE 24 mg/kg" and especially "TP/Vehicle" groups continued to increase during the 3 weeks of SC injection of testosterone and during the 2 weeks of oral treatment with CPE or the vehicle, whereas it decreased during the final week of oral treatment for the "TP/CPE 48 mg/kg" group to approach the value for the "Control/Vehicle" group. (The statistical treatments have yet to be done).

Treatment of the rats with CPE at 48 mg/kg made it possible to limit the increase in the mean intake of drink observed for the rats of the "TP/Vehicle" and "TP/CPE 24 mg/kg" groups associated with the subcutaneous (SC) injections of testosterone, thus limiting the effects of the induction of prostate hyperplasia.

Weight of the Prostates (FIGS. 10 and 11)

The mean weight of the prostates for the rats of the "TP/Vehicle" group (2.26 g/kg body weight) is significantly higher than that for the rats of the "TP/CPE 24 mg/kg" (2.06 g/kg body weight), "TP/CPE 48 mg/kg" (1.55 g/kg body weight) and "Control/Vehicle" (1.31 g/kg body weight) groups. The mean weight of the prostates for the rats of the two "TP/CPE 24 mg/kg" and "TP/CPE 48 mg/kg" groups is also significantly higher than that for the rats of the "Control/Vehicle" group, but it is lower than that for the rats of the "TP/Vehicle" group, especially for the "TP/CPE 48 mg/kg" group.

It is also observed that the mean weight of the prostates of the rats of the "TP/CPE 48 mg/kg" group is significantly lower than that for the rats of the "TP/CPE 24 mg/kg" group ($P<0.0001$).

Treatment of the rats with CPE at a dose of 48 mg/kg made it possible to greatly limit the increase in mean weight gain of the prostate observed for the rats of the "TP/Vehicle" group which is associated with the SC injections of testosterone, thus very greatly limiting the effects of the induction of the prostate hyperplasia.

3. Conclusion

Treatment of rats with an already existing prostate hyperplasia with CPE at a dose of 48 mg/kg made it possible to limit the effects of this pathology.

EXAMPLE 3

Example of Cocoa Polyphenol Extracts

| Cocoa polyphenol extract analysis | | | |
|---|---|---|---|
| Parameters | Units | Results | Methods |
| Starch | % | <0.5 | Enzymatic kit |
| Caffeine | mg/100 g | 759 | HPLC/UV |
| Cellulose | % | 0.2 | WENDE |
| Ash | % | 4.9 | Decree of 16/10/75 |
| Soluble and insoluble fiber | | | AOAC 985-29 |
| Soluble fiber | % | 0.7 | |
| Insoluble fiber | % | 3.3 | |
| Humidity | % | 3.7 | Decree of 16/10/75 |
| Magnesium | mg/100 g | 242 | Decree 8.9.77 (MO0147) |
| Total fats | % | 13.9 | Decree of 16/10/75 |
| Phosphorus | mg/100 g | 197 | Decree of 08/09/77 |
| Total polyphenols | % | 36.9 | Folin-Ciocalteu method |
| Potassium | mg/100 g | 1984 | Decree 8.9.77 (MO0147) |
| Proteins (N × 6.25) | % | 31.1 | DUMAS |
| Sodium | mg/100 g | 21 | Decree 8.9.77 (MO0147) |
| Pectic substances (as galacturonic acid) | % | >1.5 | NF V 05-128 |
| Sugars | | | HPLC/refractometry |
| Fructose | % | 1.4 | |
| Glucose | % | 1.2 | |
| Sucrose | % | 10.4 | |
| Maltose | % | 0.6 | |
| Lactose | % | <0.5 | |
| Theobromine (on chocolate) | % | 12.25 | HPLC/UV |
| Vitamin A (Retinol) | μg/100 g | <20 | NF V18-401 (1987) |
| Vitamin B1 (thiamine) | mg/100 g | <0.10 | Decree of 12.01.99 |
| Vitamin B12 (Cyanocobolamine) | μg/100 g | 0.6 | AOAC 952-20 (1990) |
| Vitamin B2 (Riboflavine) | mg/100 g | 0.4 | Decree of 12.01.99 |
| Vitamin B5 (Pantothenic acid) | mg/100 g | 3.2 | AOAC 945-74 (1990) |
| Vitamin B6 (Pyridoxine) | mg/100 g | <0.1 | ME 0099 (HPLC/fluorimetry) |
| Vitamin C | mg/100 g | <1 | HPLC/UV |
| Vitamin D3 | μg/100 g | <0.4 | HPLC/UV |
| Vitamin E (d,l-α-tocopherol) | mg/100 g | 1.9 | NF V18-402(87) |
| Vitamin H (biotin) | μg/100 g | <1 | HPLC |
| Vitamin K1 | μg/100 g | 6.58 | HPLC |
| Vitamin K3 (Menadione) | mg/100 g | <0.40 | EEC 5th directive |
| Vitamin PP (Niacin) | mg/100 g | 3.6 | HPLC |
| Vitamin B9 total (folic acid) | μg/100 g | 79 | Pr EN14131 |
| Hemicellulose | % | <0.2 | Internal |
| Lignin | % | 1.0 | Internal |
| METALS | | | |
| Calcium | mg/100 g | 4 | Decree of 8.9.77 (MO0147) |
| MYCOTOXINS | | | |
| Ochratoxin A | μg/kg | <1.0 | Mc 155 HPLC/FLUO |

| Composition of a Cameroon polyphenol extract | | |
|---|---|---|
| | | Polyphenol extract |
| Amount of polyphenols (% by mass as epicatechin equivalent) | | 35.50 |
| Free-radical-scavenging activity ($IC_{50}$ in μM) | | 66.40 |
| Amount of purines (% by mass) | Theobromine | 9.98 |
| | Caffeine | 0.65 |
| | Total | 10.63% |
| Amount of sugars (% by mass) | Glucose | 0.20 |
| | Fructose | 0.00 |

-continued

Composition of a Cameroon polyphenol extract

|  |  | Polyphenol extract |
| --- | --- | --- |
|  | Sucrose | 13.08 |
|  | Maltose | 0.00 |
|  | Total | 13.27% |
|  | Amount of fats (% by mass) | 5.56% |
| Composition of the fat | % of fatty acids | 7.895 |
|  | % of sterols | 1.869 |
|  | % of β-sitosterol | 1.463 |
|  | Relative to the extract | 0.081% |
|  | % of diglycerides | 7.549 |
|  | % of triglycerides | 82.302 |
|  | Humidity (% by mass) | 3.62% |

Supplementation of Food Using an Extract According to the Invention

| Mean polyphenol composition of cocoa extract | |
| --- | --- |
| Flavonoids | 68% |
| Other polyphenols | 30% |
| Recommended daily doses of: | |
| PCO | 125 mg/day/person ie 1.79 mg/day/kg |
| Flavonoids | 150 mg/day/person ie 2.15 mg/day/kg |
| PCO: | proanthocyanadin oligomer (to be checked) |
| Since the rats weigh on average 350 g, each rat must be given: | |
| PCO | 0.63 mg/day |
| Flavonoids | 0.75 mg/day |

Taking into account the polyphenol composition of the cocoa extract:
2.10 mg of pure polyphenol to achieve the recommended dose of PCO,
1.10 mg of pure polyphenol to achieve the recommended dose of epicatechin.

An amount of 3 mg/day/rat of pure polyphenols may be chosen in order to comply with the recommended daily dose for each type of polyphenol.

2 Specific Extracts:
Ivory Coast Polyphenol Extract Rich in β-Sitosterol: 37.45% polyphenols.
Polyphenol extract (Cameroon): 35.5% polyphenols.
In the first case, 8 mg/day/rat of the Ivory Coast extract should be given. In the second case, 8.5 mg/day/rat of the Cameroon extract should be given. A chromatogram of each of these extracts is given in FIGS. 12 and 13.

EXAMPLE 4

Evaluation of the Toxicity of a Cocoa Polyphenol Extract (CPE)

1. Materials and methods

Animals:
30 adult male rats and 30 adult female Wistar rats, 120-130 g, controlled conditions of temperature (22±2° C.), humidity (50±10%), inverted 12-hour lighting cycle (light from 08:00 h to 20:00 h), food and drink ad libitum.

Treatments:
Cocoa polyphenol extract (CPE) administered orally for 28 days at doses of 50 (FaD), 200 (DI) or 800 (FoD and Fod Sat) mg/kg.

| Treatment | Male rats | Female rats |
| --- | --- | --- |
| Vehicle | 6 rats | 6 rats |
| CPE 50 mg/kg | 6 rats | 6 rats |
| CPE 200 mg/kg | 6 rats | 6 rats |
| CPE 800 mg/kg | 12 rats | 12 rats |

Monitoring of the Animals:
Daily clinical examination of all of the animals before treatment,
Daily checking of the survival of the animals after treatment,
Weighing of the animals 3 times a week for 4 to 6 weeks.
Sacrifice, Removals and Autopsy of the Animals:
Sacrifice of half of the animals after 28 days of daily oral administration of CPE at doses of 50, 200 or 8000 mg/kg and of the other half 15 days after the final administration of CPE at these same doses,
Blood samples taken for hematological and biochemical analyses,
Complete autopsy of all of the animals and removal of 4 to 20 organs per rat for histopathological analyses.

2. Results

Mortality of the Animals
No mortality observed in the male rats and in the female rats after repeated oral administrations of CPE at doses of 50, 200 and 800 mg/kg.
Weight of the Animals (FIGS. 14 and 15)
No weight loss observed in the male rats and in the female rats after repeated oral administrations of CPE at doses of 50, 200 and 800 mg/kg.
Behavior of the Animals
No strange behavior observed in the male rats and in the female rats after repeated oral administrations of CPE at doses of 50, 200 and 800 mg/kg.

| Analysis of the polyphenols (oligomers) | | | | | | | | | | | | |
| --- | --- | --- | --- | --- | --- | --- | --- | --- | --- | --- | --- | --- |
| Sample | 1 mers | 2 mers | 3 mers | 4 mers | 5 mers | 6 mers | 7 mers | 8 mers | 9 mers | 10 mers | >10 mers | Total mg/g |
| Cocoa extract | 50.76 | 43.60 | 45.15 | 27.44 | 23.16 | 21.41 | 8.28 | 5.60 | 6.90 | 2.57 | 58.21 | 293.08 |

Autopsy of the Animals (FIGS. 16 to 27)
No sign of macroscopic toxicity observed in the male rats and in the female rats after repeated oral administrations of CPE at doses of 50, 200 and 800 mg/kg.
3. Conclusion
⇒ After 28 Days of Oral Administration of CPE:
no toxicity for the 50 and 200 mg/kg doses for both sexes, but, on the contrary, immunostimulation (increase in the weight of the spleen and of the thymus),
toxic effect for the 800 mg/kg dose in both sexes: increase in the level of ASAT and decrease in ALAT and in the size of the liver
⇒ 15 Days after the Final Oral Administration of CPE:
no toxicity for the 50 and 200 mg/kg doses in both sexes,
no more toxicity for the 500 mg/kg dose in both sexes=reversibility of the toxic effects observed for this dose after 28 days of oral administration of CPE.

EXAMPLE 5

Determination of the $LD_{50}$ of a Cocoa Polyphenol Extract (CPE) in Rats

1. Materials and Methods
Animals:
18 adult male rats and 18 adult female Wistar rats, 150-175 g, controlled conditions of temperature (22±2° C.), humidity (50±10%), inverted 12-hour lighting cycle (light from 08:00 h to 20:00 h), food and drink ad libitum.
Treatments:
Cocoa polyphenol extract (CPE) administered orally at a dose of 2 g/kg=limit dose according to the OCDE standards.

| Treatment | Male rats | Female rats |
|---|---|---|
| — | 6 rats | 6 rats |
| Vehicle | 6 rats | 6 rats |
| CPE 2 g/kg | 6 rats | 6 rats |

Experimental Procedure:
Animals fasted the day before the administration of CPE,
Animals weighed just before administration of CPE,
Oral administration of CPE at a dose of 2 g/kg,
Animals fasted for 3 hours after oral administration of CPE.
Monitoring of the Animals:
Daily clinical examination of all of the animals before treatment,
Daily checking of the survival of the animals after treatment,
Weighing of the animals 3 times a week for 2 weeks.
Sacrifice and Autopsy of the Animals:
Sacrifice of the animals 14 days after single oral administration of CPE at a dose of 2 g/kg,
Full autopsy of all of the animals.
2. Results
Mortality of the Animals
No mortality observed in the male rats and in the female rats after single oral administrations of CPE at a dose of 2 g/kg.
Weight of the Animals
No weight loss observed in the male rats and in the female rats after single oral administration of CPE at a dose of 2 g/kg.
Autopsy of the Animals
No sign of macroscopic toxicity observed in the male rats and in the female rats after single oral administration of CPE at a dose of 2 g/kg.
3. Conclusion
→ The $LD_{50}$ of CPE therefore cannot be determined according to the OCDE standards.
CPE as a single oral administration is therefore not toxic.
4. Materials and Methods
Animals:
6 male Wistar rats (290-300 g) and 6 female Wistar rats (200-210 g) of the control group,
Controlled conditions of temperature (22±2° C.), humidity (50±10° C.), inverted 12-hour lighting cycle (light from 08:00 h to 20:00 h), food and drink ad libitum.
Treatments:
Cocoa polyphenol extract (CPE) administered orally at a dose of 4 g/kg=twice the limit dose recommended by the OCDE.

| Treatment | Male rats | Female rats |
|---|---|---|
| CPE 4 g/kg | 6 rats | 6 rats |

Experimental Procedure:
Animals fasted the day before the administration of CPE,
Animals weighed just before administration of CPE,
Oral administration of CPE at a dose of 4 g/kg,
Animals fasted for 3 hours after oral administration of CPE.
Monitoring of the Animals:
Daily clinical examination of all of the animals before treatment,
Daily checking of the survival of the animals after treatment,
Weighing of the animals 3 times a week for 2 weeks.
Sacrifice and Autopsy of the Animals:
Sacrifice of the animals 14 days after single oral administration of CPE at a dose of 4 g/kg,
Full autopsy of all of the animals.
5. Results
Mortality of the Animals:
No mortality observed in the male rats, but 67% (4/6) mortality in the female rats after single oral administration of CPE at a dose of 4 g/kg.
Weight of the Animals (FIGS. 28 and 29)
Slight weight loss observed in the male rats and in the surviving female rats (~10 g on average in both cases) after single oral administration of CPE at a dose of 4 g/kg.
Behavior of the Animals:
No strange behavior observed in the male rats and in the surviving female rats after single oral administrations of CPE at a dose of 4 g/kg.
Autopsy of the Animals:
No sign of macroscopic toxicity observed in the male rats and in the surviving female rats after single oral administration of CPE at a dose of 4 g/kg.
6. Conclusion
The $LD_{50}$ of CPE was not reached in the male rats and is therefore greater than 4 g/kg. CPE as a single oral administration is therefore not toxic in male rats up to a dose of at least 4 g/kg.
The $LD_{50}$ of CPE was reached and even exceeded in the female rats and is therefore between 2 and 4 g/kg.

EXAMPLE 6

Prostate Cancer on Cell Models in vitro effects of cocoa polyphenols and of β-sitosterol on the growth of cancerous and normal human prostate cells.

The antiproliferative properties of cocoa polyphenol extracts were studied on cancerous human colon cells, but not on cancerous or normal human prostate cells.

The effects of various cocoa polyphenol extracts originating from different countries, as defined above, were thus examined, alone or in combination with β-sitosterol, on the growth of cancerous human prostate cells (DU145 and 22Rv1 cells) and normal human prostate cells (RWEP-1 cells).

The results obtained in this in vitro study show that certain polyphenols originating from specific countries reduce the cell proliferation in a dose-dependent and time-dependent manner, and that other polyphenols inhibit the growth of the cells in a dose-dependent manner.

The origin of the polyphenols is a major factor for the efficacy of these compounds. In addition, the cocoa extracts tested are more effective on cells that are sensitive to androgens (22Rv1 cells) than on cells that are not sensitive to androgens (DU145 cells). It thus appears that interactions exist between the polyphenols and the intracellular steroid receptors.

The results obtained show that the polyphenols and β-sitosterol have an antiproliferative effect on the growth of cancerous prostate cells.

The effect of the polyphenols and of β-sitosterol was tested on the growth of RWEP-1 and 22Rv1 cells as a function of the dose, and on the growth of DU145 cells as a function of the dose and of time.

Each product (1 to 5) was applied for 1 to 72 hours, at various concentrations. The number of cells was compared with a control, namely cells cultured in the absence of the test compound.

Table 1 below illustrates the final concentration of cocoa extracts and of β-sitosterol for each product tested on the prostate cells DU145, 22Rv1 and RWEP-1.

lection (ATCC, Rockville, Md.). The cells were maintained in the form of a monolayer culture according to the usual techniques, in 75 cm$^3$ flasks, at 37° C., in an atmosphere containing 5% $CO_2$ and at 95% humidity, in a medium free of serum and of keratinocytes, supplemented with 2.5 µg of recombinant human EGF and 25 mg of calf pituitary extract. The medium was supplied by Gibco BRL (Cergy Pontoise, France).

Preparation of the Media Supplemented with the Test Products

Five products were tested for this study and were stored protected from light, at +4° C. The β-sitosterol (product 1), obtained from Sigma Chemicals, was first dissolved in absolute ethanol, up to a final concentration of 24.1 mM. Product 2, supplied by Barry Callebaut, France, is a defatted cocoa extract containing 35.5% polyphenols and 0.081% β-sitosterol. Product 3 was reconstituted from products 1 and 2 and contained 35.5% polyphenols and 0.72% β-sitosterol. Products 4 and 5 were manufactured by Barry Callebaut, France. The composition of product 4 is unknown, and contains no β-sitosterol. Product 5 contains 35.27% polyphenols and 0.72% β-sitosterol. Products 2, 3, 4 and 5 were first dissolved in whole medium. As regards products 2, 4 and 5, the total polyphenols of the cocoa extracts originate from different countries.

Just before use, the final concentrations of products (table 1) used are prepared for the various experiments by means of stock solutions, by diluting the stock solution in whole medium. 64.2 µM of β-sitosterol is the maximum dose used in this solubility range and in the physiological range (4 to 70 µM). The absolute ethanol is at a constant concentration of 0.26% in the solvent-based control, in the negative control and in the 8 test concentrations. The ratios of the β-sitosterol and of the polyphenols for products 2, 3 and 5 are as follows:

TABLE 1

| Product 1 | Product 2 | | Product 3 | | Product 4 | Product 5 | |
|---|---|---|---|---|---|---|---|
| [β-sitosterol]$^a$ | Extract$^a$ | [β-sitosterol] | Extract | [β-sitosterol] | Extract | Extract | [β-sitosterol] |
| $2 \cdot 10^{-2}$ | 0.2 | $1.6 \cdot 10^{-1}$ | 0.2 | $1 \cdot 10^{-3}$ | 0.2 | 0.2 | $1 \cdot 10^{-3}$ |
| $1 \cdot 10^{-3}$ | 0.1 | $8 \cdot 10^{-5}$ | 0.1 | $0.5 \cdot 10^{-3}$ | 0.1 | 0.1 | $0.5 \cdot 10^{-3}$ |
| $5 \cdot 10^{-1}$ | 0.05 | $4 \cdot 10^{-8}$ | 0.05 | $2.5 \cdot 10^{-1}$ | 0.05 | 0.05 | $2.5 \cdot 10^{-1}$ |
| $2.5 \cdot 10^{-3}$ | 0.025 | $2 \cdot 10^{-8}$ | 0.025 | $1.2 \cdot 10^{-1}$ | 0.025 | 0.025 | $1.2 \cdot 10^{-4}$ |
| $1.2 \cdot 10^{-4}$ | 0.0125 | $1 \cdot 10^{-5}$ | 0.0125 | $0.6 \cdot 10^{-1}$ | 0.0125 | 0.0125 | $0.6 \cdot 10^{-1}$ |
| $6.2 \cdot 10^{-5}$ | 0.00625 | $5 \cdot 10^{-6}$ | 0.00625 | $3 \cdot 10^{-5}$ | 0.00625 | 0.00625 | $3 \cdot 10^{-5}$ |
| $3.1 \cdot 10^{-5}$ | 0.003125 | $2.5 \cdot 10^{-6}$ | 0.003125 | $1.5 \cdot 10^{-5}$ | 0.003125 | 0.003125 | $1.5 \cdot 10^{-5}$ |
| $1.5 \cdot 10^{-5}$ | 0.001562 | $1.25 \cdot 10^{-6}$ | 0.001562 | $7.5 \cdot 10^{-6}$ | 0.001562 | 0.001562 | $7.5 \cdot 10^{-8}$ |

$^a$values expressed in %

A) Materials and Methods

Cell Lines and Culture Conditions

The human prostate carcinoma cells DU145 and 22Rv1 were supplied by the American Type Culture Collection (ATCC, Rockville, Md.). The DU145 cells originate from a cerebral metastasic site and are not sensitive to androgens. The 22Rv1 cells originate from a prostate carcinoma and are sensitive to androgens. The cells were maintained in the form of a monolayer culture according to the usual techniques, in 75 cm$^3$ flasks (Corning), at 37° C., in an atmosphere containing 5% $CO_2$ and at 95% humidity, in an RPMI-1640 medium free of phenol red and supplemented with 10% of heat-inactivated fetal calf serum and 1% of L-glutamine.

The RPMI-1640 medium, the fetal calf serum and the L-glutamine were supplied by Gibco BRL (Cergy Pontoise, France). The cell cultures were replaced every 5 days to ensure exponential growth. The normal human prostate cells RWEP-1 were supplied by the American Type Culture Col- Product 2:2:1000
Product 3:2:100
Product 5:2:100

Tests of Cell Growth and Cell Viability

The cells were inoculated on 96-well plates at an initial density of 15 000 cells/well for DU145, at an initial density of 30 000 cells/well for 22Rv1 and at an initial density of 25 000 cells/well for RWEP-1, with 200 µL of medium per well. The cell density was optimized as a function of the time required to double the population of cells, in order to obtain a significant measurement of the Optical Density (OD) and to be able to compare the various cells lines. After 24 hours, in order to ensure uniform fixing of the cells from the start of the experiments, the products were added to the cell cultures at various concentrations and at various times. After incubation with the products, the growth and viability of the cells was measured using neutral red (NR) and sulforhodamine B (SRB) combined (In Cytotox, Vandoeuvre, France). The absorption of the vital stain NR was used by the lysosomes/endosomes and by the vacuoles of the live cells as a quantitative indication of the number and viability of the cells after treatment with a chemical test. The anionic stain SRB made it possible to quantify the viable cells via measurement of the protein content of the cells.

The cytotoxicity was evaluated 1, 3, 6, 24, 48 and 72 hours after incubating the 22Rv1, RWEP-1 and DU145 cells with the products. The cells were washed with 200 µl of washing solution in order to remove the culture medium supplemented with the products. 200 µL of neutral red base medium was added and incubated with the cells at 37° C. for 3 hours. The neutral red base medium was then removed and the cells were washed twice with phosphate-buffered physiological saline (PBS). The cells were fixed for 1 minute with 200 µL of fixing solution. 200 µL of a desorption solution were added to extract the neutral red from the cells. After 15 minutes at room temperature, the OD, which reflects the number of viable cells, was determined at 540 nm with a 690 nm reference filter, using a microplate reader (Genios, Tecan SA, France). Next, the cells were washed 4 times with PBS. 50 µL of 0.4% SRB solution were added to the culture and, 1 hour later, the monolayers were washed with 200 µL of rinsing solution to remove the unbound stain. 200 µL of solubilizing solution were then incubated with the cells to extract the SRB from the cells. After incubation overnight at room temperature, the plates were read at 540 nm with a 690 nm reference filter. Each experiment was performed three times in order to obtain 18 values per test condition.

Morphology

To document the changes in morphology and in growth of the cells observed during the treatment, the cells to which the maximum concentrations of each product were added were examined (magnification x40) by phase-contrast microscopy (Leica DM IL microscope) and photographed using a digital photography system (Trinitron® Color Video Monitor). The RWEP-1, 22Rv1 and DU145 cells were examined with the media containing the products after 48 hours of incubation.

B) Results

Morphological Alterations

The effect of each product on the morphology of the three cell lines is illustrated in FIG. 30. The cells were treated with the maximum concentration of product for a period ranging up to 48 hours.

Rounding of the 22Rv1 cells and the absence of attached cells suggested the induction of apoptosis by the addition of products 2, 4 and 5. In principle, product 3 appears to be less effective on the 22Rv1 cells. The reason for this is that a smaller number of rounded cells was observed, and also attached cells showing a loss of morphology. No significant difference in terms of density and morphology between the 22Rv1 cells treated with β-sitosterol and the untreated cells was observed. However, rounded cells were observed on the monolayer, which suggests a very weak inhibition of the cell proliferation.

The DU145 cells proved to be less sensitive to the treatments with products 2, 3, 4 and 5 than the 22Rv1 cells. Specifically, no rounded cells were observed, but many attached cells show a loss of morphology. However, the number of attached cells is lower with products 4 and 5 than with products 2 and 3. The DU145 cells appear to be more sensitive to products 4 and 5. No significant difference was observed in terms of density and morphology between the DU145 cells treated with β-sitosterol and the untreated cells.

For the normal prostate cells RWEP1, no significant morphological difference was observed between the treated cells and the untreated cells for each product. However, all the products proved to be sufficient to slightly reduce the number of cells on day 2. At the maximum concentrations, the products affect the growth of the normal prostate cells by slowing down the cell proliferation.

Inhibition of Growth of the Prostate Cells as a Function of the Dose and of Time The effect on the proliferation of RWEP-1, 22Rv1 and DU145 cells was studied, as a function of the dose and of time, of the products at a percentage of between $1.56 \times 10^{-5}\%$ and $2 \times 10^{-2}\%$ for product 1 and between 0.2 and $1.562 \times 10^{-3}\%$ for the other products, after 1, 3, 6, 24, 48 and 72 hours of treatment (table 1, FIGS. 31, 32 and 33).

Cytotoxic Effect of the Products on Growth of the RWEP-1 Cells

The $IC_{50}$ was never reached in the presence of β-sitosterol between 1 and 72 hours of treatment. β-Sitosterol thus has no cytotoxic effect on the RWEP-1 cells. Furthermore, after 48 hours of treatment and for the assay with SRB, a dose-dependent inhibitory effect of β-sitosterol on the normal prostate cell line was observed. At this stage, the treatment with β-sitosterol caused a significant reduction in protein synthesis in the RWEP-1 cells (FIG. 31). For products 2, 3, 4 and 5, the $IC_{50}$ after 24 hours of treatment was not reached. However, a two-phase curve was observed after 48 and 72 hours of treatment. In general, all these products inhibited the cell proliferation at concentrations of between 0.003125% and 0.025% of extract (FIG. 31). No significant difference in inhibition was observed between the products and the $IC_{100}$ values were never reached (table 3).

Anticancer Effects of the Products on the Growth of the 22Rv1 Cells

At 1, 3 and 6 hours of treatment, β-sitosterol did not inhibit the lysosomial activity or protein synthesis in the 22Rv1 cells. In addition, the $IC_{50}$ value was reached at 24 and 72 hours. The 22Rv1 cells are the only cancer cell line for which $IC_{50}$ values were reached with β-sitosterol. At 48 hours of treatment, a dose-dependent inhibitory effect was induced with β-sitosterol on the protein synthesis activity (FIG. 31).

In addition, the 22Rv1 cell line was the only line that presented $IC_{50}$ values during the short-term treatment with products 2, 3, 4 and 5 (table 2). Thus, this cancer cell line appears to be the most sensitive to the cocoa extracts. The $IC_{50}$ values at 24, 48 and 72 hours of treatment with all the products are presented in table 3. The effect as a function of dose and of time is represented in FIG. 33 in order to allow a comparison of the anticancer activity of product 2 with that of product 3, and that of product 4 with that of product 5. All these products showed an effect that depends on the dose and on time.

TABLE 2

| Hours | Test | Product 2 $IC_{50}{}^a$ | Product 3 $IC_{50}$ | Product 4 $IC_{50}$ | Product 5 $IC_{50}$ |
|---|---|---|---|---|---|
| 1 h | NR | 0.049 | 0.060 | 0.029 | 0.031 |
|  | SRB | 0.052 | 0.061 | 0.076 | 0.069 |
| 3 h | NR | 0.035 | 0.036 | 0.023 | 0.030 |
|  | SRB | 0.036 | 0.051 | 0.041 | 0.043 |
| 6 h | NR | 0.034 | 0.034 | 0.025 | 0.026 |
|  | SRB | 0.030 | 0.024 | 0.032 | 0.039 |

$^a IC_{50}$ values expressed as % of extract

TABLE 3

| Hours | Cell line | Assay | β-sitosterol max. inhibition | 2nd product IC$_{50}$ | 2nd product IC$_{100}$ | 3rd product IC$_{50}$ | 3rd product IC$_{100}$ | 4th product IC$_{50}$ | 4th product IC$_{100}$ | 5th product IC$_{50}$ | 5th product IC$_{100}$ |
|---|---|---|---|---|---|---|---|---|---|---|---|
| 24 h | RWEP1 | NR | 15%[b] | none | none | none | none | none | none | none | none |
|  |  | SRB | 9% | none | none | none | none | none | none | none | none |
|  | 22RV1 | NR | 49% | 0.0080 | 0.025 | 0.0169 | 0.05 | 0.0098 | >0.1 | 0.0173 | >0.1 |
|  |  | SRB | 49% | 0.0085 | 0.025 | 0.0170 | 0.05 | 0.0098 | >0.2 | 0.0152 | >0.1 |
|  | DU145 | NR | 11% | 0.0535 | >0.2 | 0.0835 | >0.2 | 0.1105 | >0.2 | 0.0940 | >0.2 |
|  |  | SRB | 42% | 0.0478 | >0.2 | 0.0874 | >0.2 | 0.0952 | >0.2 | 0.0810 | >0.2 |
| 48 h | RWEP1 | NR | 29% | 0.021 0.073 | none | 0.121 0.078 | none | 0.022 0.087 | none | 0.024 0.103 | none |
|  |  | SRB | 48% | 0.017 0.086 | none | 0.017 0.089 | none | 0.021 0.081 | none | 0.021 0.138 | none |
|  | 22RV1 | NR | 36% | 0.0080 | 0.025 | 0.0076 | 0.0125 | 0.0074 | 0.0125 | 0.0086 | 0.0125 |
|  |  | SRB | 47% | 0.0078 | 0.025 | 0.0070 | 0.0125 | 0.0088 | 0.0125 | 0.0083 | 0.0125 |
|  | DU145 | NR | 21% | 0.0507 | >0.2 | 0.0551 | >0.1 | 0.084 | >0.2 | 0.0350 | >0.2 |
|  |  | SRB | 44% | 0.0509 | >0.2 | 0.0504 | >0.2 | 0.062 | >0.2 | 0.0353 | >0.2 |
| 72 h | RWEP1 | NR | 11% | 0.039 0.153 | none | 0.034 0.081 | none | 0.030 0.096 | none | 0.036 0.104 | none |
|  |  | SRB | 26% | 0.03 0.1 | none | 0.024 0.065 | none | 0.021 0.075 | none | 0.021 0.071 | none |
|  | 22RV1 | NR | CI$_{50}$ = 17.84[a] | 0.0080 | 0.025 | 0.0061 | 0.025 | 0.0077 | 0.025 | 0.0110 | 0.025 |
|  |  | SRB | CI$_{50}$ = 34.01 | 0.0078 | 0.025 | 0.0055 | 0.025 | 0.0062 | 0.025 | 0.0090 | 0.025 |
|  | DU145 | NR | 42% | 0.0498 | >0.2 | 0.0612 | >0.2 | 0.0594 | >0.2 | 0.0310 | >0.2 |
|  |  | SRB | 40% | 0.0450 | >0.2 | 0.0496 | >0.2 | 0.0454 | >0.2 | 0.0297 | >0.2 |

[a]The RWEP-1, 22Rv1 and DU145 cells were incubated for 1, 3, 6, 24, 48 and 72 hours in the presence of various concentrations of β-sitosterol and of cocoa extracts (table I). Mean of three experiments performed three times.
[b]Maximum inhibition expressed in %;
[c]IC$_{50}$ values expressed in μM;
[d]IC$_{50}$ values expressed as % of extract;
none: not obtained Anticancer Effects of the Products on the Growth of the DU145 Cells In contrast with the 22Rv1 cells, β-sitosterol did not induce an IC$_{50}$ in the DU145 cells during short-term and long-term treatments. Furthermore, this phytosterol had a dose-dependent inhibitory effect on the protein synthesis activity at 48 hours of treatment (FIG. 31). In addition, no IC$_{50}$ was observed with products 2, 3, 4 and 5 during the short-term treatment. The DU145 cells appear to be more resistant to the cocoa extracts than the 22Rv1 cells. the IC$_{50}$ values of all the products at 24, 48 and 72 hours of treatment are presented in table 3. The dose- and time-dependent effects are shown in FIG. 32 to allow a comparison of the anticancer activity of product 2 with that of product 3, and of product 4 with that of product 5. All these products had a dose- and time-dependent effect, except for product 2, which showed constant activity at the three treatment times.

C) Discussion and Conclusion

Certain dietary factors may influence the development of cancer by altering the cellular signal transmission pathways. Attention has increasingly focused in recent years on polyphenols from fruit and vegetables on account of their high antioxidant power. Furthermore, β-sitosterol may play a protective role in the development of cancer. This notion is supported by in vivo and in vitro studies.

The aim of the present in vitro study was to analyze the effects of cocoa polyphenols present in the diet on the growth of RWEP-1, 22Rv1 and DU145 cells, as a function of time and of the dose.

The morphological and proliferative changes of the three human prostate cell lines are illustrated in FIG. 30. The results obtained reveal a direct inhibitory effect of products 2, 3, 4 and 5 on the proliferation of the 22Rv1 and DU145 cell lines. The androgen-sensitive 22Rv1 cells are more sensitive to the action of the cocoa extracts than the androgen-insensitive DU145 cells. Specifically, the 22Rv1 cells do not adhere and form aggregates in suspension, whereas the DU145 cells are clearly attached, although the number of cells observed is low. These results suggest that the steroid receptors are involved in the action of the polyphenols. The presence of interactions between the polyphenols and the steroid receptors (AR) may explain a powerful inhibition of the 22Rv1 cells. In this regard, it has been reported that certain polyphenols are thought to be agonists of steroidal receptors. Cocoa polyphenols may inhibit the DU145 cells by altering the cellular signal transmission pathways.

The present example also demonstrates that the three cell lines react differently to each product. Specifically, for the RWEP-1 cells, no cytotoxic effect is observed before 48 hours of treatment with all the products. The results obtained tend to demonstrate that the normal RWEP-1 cell line is the line that best withstands each dose/time effect of the products. However, at 48 and at 72 hours, the results obtained form a two-phase curve for the RWEP-1 cells incubated with the cocoa extracts. At the minimum concentrations of the products, there is no inhibition of cell proliferation. The higher the concentration of the extracts, the greater the inhibition, up to 70%. Next, the degree of inhibition decreases, even if the concentration of the extracts increases.

For the prostate carcinoma cell line 22Rv1, the results obtained from dose-dependent studies indicate that these cells are more sensitive to products 3 and 4 and products 2 and 5 proved to be the products that were the most effective for inhibiting the growth of the DU145 cells. The difference in sensitivity to cocoa extracts of the two tumor cell lines may be explained by the different origins of the tumors. The 22Rv1 cells are hormone-sensitive and originate from a prostate carcinoma. Conversely, the DU145 cells are hormone-resistant and are metastasic cells. It was also seen that the membranes of the metastasic cells have a tendency toward greater fluidity than the non-metastasic tumors. Given that their properties are different, it may be assumed that the molecular inhibition mechanisms induced with the polyphenols are not the same in the two tumor cell lines.

To explain the different inhibition profiles of the extracts, the hypothesis may be put forward that the origin of the polyphenols is very important for the efficacy of the cocoa extracts. Specifically, each extract tested contains polyphenols originating from different countries. In addition, the efficacy of the antiproliferative and antitumor properties of the polyphenols is probably associated with their degree of polymerization. It has been reported that the antioxidant power of flavonols and of procyanadins present in cocoa and chocolate may depend on the length of their oligomer chain.

Conclusion:

For each cocoa extract and at the maximum concentration, growth of the 22Rv1 and DU145 cells is completely inhibited, whereas that of the RWEP-1 cells is not inhibited. Furthermore, the 22Rv1 cells are more sensitive to the cocoa extracts than the DU145 cells. These results demonstrate that the polyphenols extracted from cocoa show specific anticancer activity against metastasic cells and prostate carcinomas. In addition, these results are the first to describe a powerful antiproliferative effect of cocoa polyphenols on cancerous human prostate cells. All the cocoa extracts, at the maximum concentrations, induce a total inhibition of the tumor cells without any effect on the RWEP-1 cells. The cocoa extracts are more effective on the non-metastasic cells than on the metastasic tumors. It is probable that the inhibition of cell growth induced with the steroid receptors is not a general mechanism, but rather a factor of the action of polyphenols.

EXAMPLE 7

Prostate Cancer on Coculture Models

In this example, the biological effects of the cocoa polyphenol extract (CPE) and of β-sitosterol are studied on a coculture of healthy and cancerous human prostate cells.

The effects of CPE and of the reference phytosterol are visualized by means of an immunolabeling technique proposed by BIOalternatives by virtue of expression of the glycoprotein galectin 8 in a coculture of cancerous and healthy human prostate cell lines, i.e. the 22Rv1 and RWEP-1 cells, respectively.

1) Material and Methods a) Cells and Culture Media Tested

Type:
Healthy human prostate epithelial cells (RWEP-1, ATCC No. CRL-11609)
Human prostate carcinoma (22Rv1 ATCC No. CRL-2505)
Culture:
37° C., 5% $CO_2$, 95% humidity
Test Media:
Medium M1=Medium recommended for healthy cells (RWEP-1):
Keratinocyte-serum free medium (KSFM) (Invitrogen, 17005-042)
Epidermal Growth Factor, 5 ng/ml (Invitrogen, 10450-013)
Bovine pituitary extract, 0.05 mg/ml (Invitrogen, 13028-014)
Penicillin 50 IU/ml-streptomycin 50 μg/ml 10 (v/v, Invitrogen 15070-063)
Medium M2=Medium recommended for tumor cells (22Rv1):
RPMI 1640 medium (Invitrogen, 31870-025)
Decomplemented fetal calf serum, 10% (v/v Invitrogen 10270-098)
L-Glutamine, 1% (v/v Invitrogen 25030-024)
Penicillin 50 IU/ml-streptomycin 50 μg/ml 1 (v/v, Invitrogen 15070-063)
Medium M3=Mixed medium:
Whole keratinocyte-serum free medium, 50% (v/v)
Whole RPMI 1640 medium, 50% (v/v)

b) Test Product and Reference Product

| Reference | Stock solution | Dilutions | Final test concentrations |
|---|---|---|---|
| β-Sitosterol Sigma, S-1270 (GT041103/1) | White powder supplied by the sponsor and stored at −20° C. protected from light | Culture media $M_1$, $M_2$ and $M_3$ | $2 \times 10^{-3}$, $1 \times 10^{-3}$; $5 \times 10^{-4}$, $2.5 \times 10^{-4}$; $1.2 \times 10^{-4}$; $6.2 \times 10^{-5}$; $3.1 \times 10^{-5}$ and $1.5 \times 10^{-5}$% |

| Test product | Stock solution | Dilutions | Final test concentrations |
|---|---|---|---|
| Cocoa polyphenol extract (GT041103/2) | Brown powder supplied by the sponsor and stored at room temperature, protected from light | Culture media $M_1$, $M_2$ and $M_3$ | $2 \times 10^{-1}$, $1 \times 10^{-1}$; $5 \times 10^{-2}$, $2.5 \times 10^{-2}$; $1.25 \times 10^{-2}$; $6.25 \times 10^{-3}$; $3.125 \times 10^{-3}$ and $1.5 \times 10^{-3}$% | c) Primary Antibody Used

Galectins belong to the lectin family. They are glycoproteins lacking enzymatic activity, of variable molecular weight, which can specifically bind oligo-saccharide ligands.

The first group consists of proteins formed from two lectin domains in tandem located at the C- and N-terminal ends, linked via a peptide sequence of variable size known as a peptide linker. Galectins 4, 6, 8 and 9 belong to this category.

Galectin 8, which is generally absent in a healthy prostate, is found in prostate carcinomas at a significantly higher level than in adenomas. As a result, an anti-galectin 8 human monoclonal antibody (R&D Systems, Ref: MAB1305) was selected to specifically fluorescence-label the human prostate tumor cell line.

d) Selection of the Coculture Medium

→ Via Immunolabeling

The coculture medium was selected in two steps:
labeling of the two cell lines inoculated independently to determine the concentration of anti-galectin 8 primary antibody that allows specific labeling of the tumor cells (22Rv1) without a background noise on the healthy cells (RWEP-1),
labeling of the two cell lines in coculture to determine whether the labeling of the tumor cells (22Rv1) is identical to that obtained in culture alone, even in the presence of the healthy cells (RWEP-1).

The healthy and tumoral prostate cells were inoculated, independently or in coculture, in 96-well microplates, at a rate of 30 000 cells per well in each culture medium (M1, M2 or M3).

After culturing for 48 hours in an incubator at 37° C. and 5% $CO_2$ of saturated humidity, the cell lawns were fixed in alcohol/acetic acid and then labeled with the anti-galectin 8 human monoclonal antibody for 1 hour. The primary antibody was then revealed with an anti-mouse immunoglobulin goat conjugate antibody, Alexia Fluor 488 (Interchim, Ref:

A-11029). The concentrations of primary and secondary antibodies were rigorously identical for the cultures prepared independently and for the coculture. After intensive washing with PBS, the labeled cell lawns were observed using a Nikon DXM1200F camera driven by LUCIA 6.0 software. All the images were acquired under the same conditions and with identical settings of the camera.

→ Via a Cell Proliferation Test: Neutral Red Release Method

The neutral red release method made it possible to determine:

the culture medium allowing the production of $IC_{50}$ values close to those obtained previously (Laboratoire IN CYTOTOX, Vandoeuvre-Lès-Nancy) for the two prostate cell lines cultured independently, two concentrations of β-sitosterol and of cocoa polyphenol extract applied to the healthy and tumoral prostate cells for the final step of immunolabeling in coculture.

The healthy and tumoral prostate cells were inoculated, independently, in 96-well microplates, at a rate of 30 000 cells per well in each culture medium (M1, M2 or M3) and incubated for 24 hours in an incubator at 37° C. and 5% $CO_2$ of saturated humidity.

After 24 hours of growth, the healthy and tumoral cell lines were incubated in the presence of β-sitosterol (reference product) at 8 concentrations (see paragraph b) above) or of CPE at 8 concentrations (see paragraph b) above). Each test concentration was prepared in 6 wells. The healthy and tumoral cells were incubated with the products for 24 hours. At the end of the incubation time with the products, the cell lawns were subjected to the neutral red release test. Neutral red is a vital stain, having the capacity to penetrate passively into lysosomes, at physiological pH. During deterioration of the membrane, neutral red leaves the cytoplasm. The amount of stain incorporated into the cells is thus proportional to the number of cells still having an intact membrane. The amount of stain incorporated into the cells is measured by spectrophotometric reading at 540 nm and is directly pro-portional to the number of live cells. The results were expressed as a percentage of inhibition relative to the untreated control.

e) Treatment with the Test Products and Immunolabeling of The Coculture

The healthy and tumoral cells were inoculated in coculture, at a rate of 30 000 cells per well for each cell line, in the selected medium for obtaining uniform and specific labeling of the tumoral cells.

After 24 hours in an incubator at 37° C. and 5% $CO_2$ of saturated humidity, the coculture was incubated in the presence of β-sitosterol at two concentrations and of CPE also at two concentrations.

At the end of the incubation time with the products, the cell lawns were fixed in alcohol/acetic acid and then labeled with the anti-galectin 8 human monoclonal antibody for 1 hour. The primary antibody was then revealed with an anti-mouse immunoglobulin goat conjugate antibody, Alexia Fluor 488 (Interchim, Ref: A-11029). After intensive washing with PBS, the labeled cell lawns were observed using a Nikon DXM1200F camera driven by LUCIA 6.0 software. All the images were taken under the same conditions and with identical camera settings.

For the experiment, in order to improve the intensity of this immunolabeling and for better visual rendering quality, the concentration of the anti-galectin 8 primary antibody was increased from 1/50th to 1/20th. Furthermore, this primary antibody was incubated overnight at +4° C. for better fixing of the antibody and thus for better labeling intensity.

2) Results a) Selection of the Coculture Medium

→ Via Immunolabeling

The results of the immunolabeling on the healthy and tumoral human prostate cell lines cultured independently are presented in FIGS. 34a, 34b, 34c and 35a, 35b and 35c.

The results of the immunolabeling on the healthy and tumoral human prostate cell lines cultured in coculture are presented, respectively, in FIGS. 36a, 36b and 36c.

FIGS. 36a, 36b and 36c represent, respectively, the coculturing of the healthy and tumoral lines in medium M1 (FIG. 36a), M2 (FIG. 36b) and M3 (FIG. 36c).

For the prostate cells cultured independently (FIGS. 34a-c and 35a-c), the healthy cell line (RWEP-1) cultured in the three media M1, M2 or M3 was not labeled with the anti-galectin 8 primary antibody and with the secondary antibody Alexia Fluor 488. Moreover, the tumoral cell line (22Rv1) was specifically recognized by the anti-galectin 8 antibody, the labeling of which was more homogeneous and more intense under the culture conditions of medium M3.

The results obtained for the immunolabeling of the cells in coculture (FIGS. 36a-c) confirm those obtained for the cells cultured independently. Specifically, the labeling of the tumoral cells (22Rv1) is more homogeneous under the culture conditions of medium M3. In the media M1 and M2, heterogeneous labeling was observed in the coculture, ranging from weak to strong.

Thus, the medium M3 allowed a precise and specific observation of the tumoral cells (22Rv1) without labeling of the healthy cells (RWEP-1).

→ Via a Cell Proliferation Test: Neutral Red Release Method

The results of the proliferation test via the neutral red release method are presented in FIGS. 37a, 37b, 37c, 37d, 37e, 37f and 38a, 38b, 38c, 38d, 38e and 38f. This test was performed on the healthy and tumoral cell lines cultured independently to determine the percentage of inhibition of proliferation induced on each cell line by the products.

FIGS. 37a to 37f represent the effects of β-sitosterol on the healthy and cancerous human prostate cell lines cultured independently in the media M1, M2 or M3.

Figure 1:
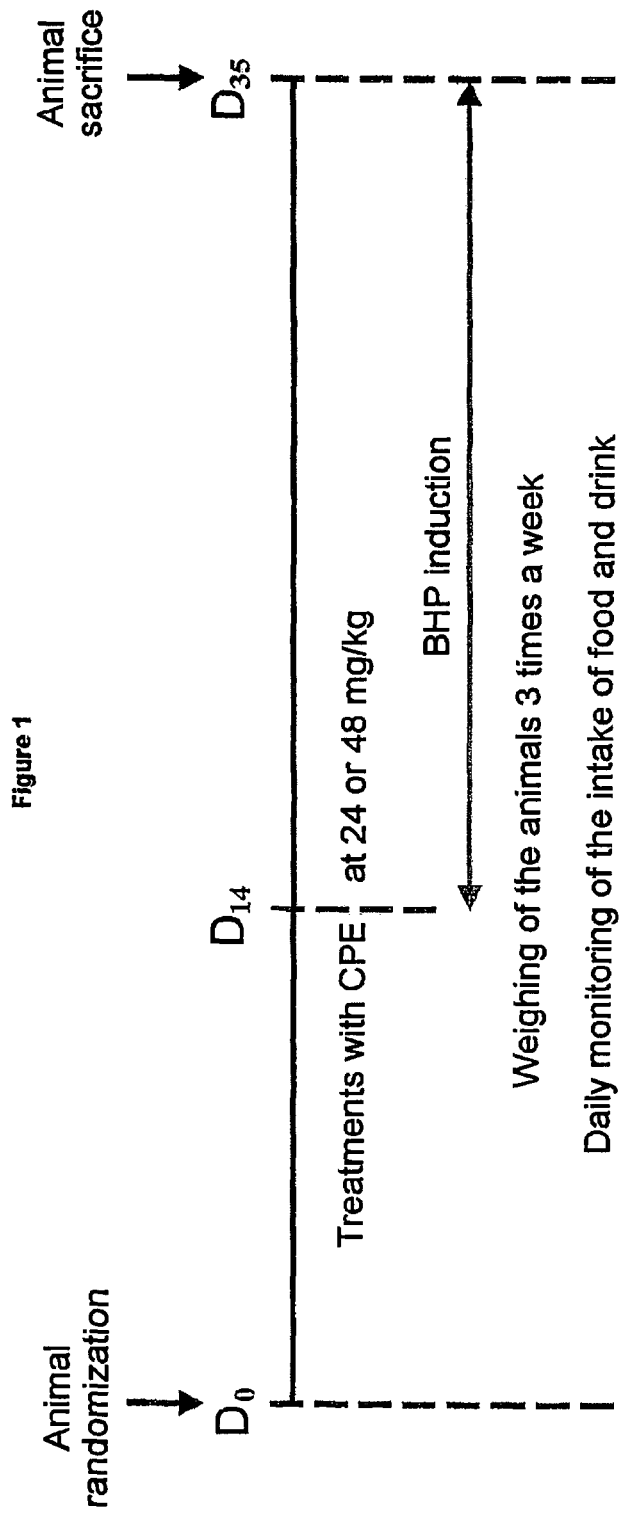
Figure 2:
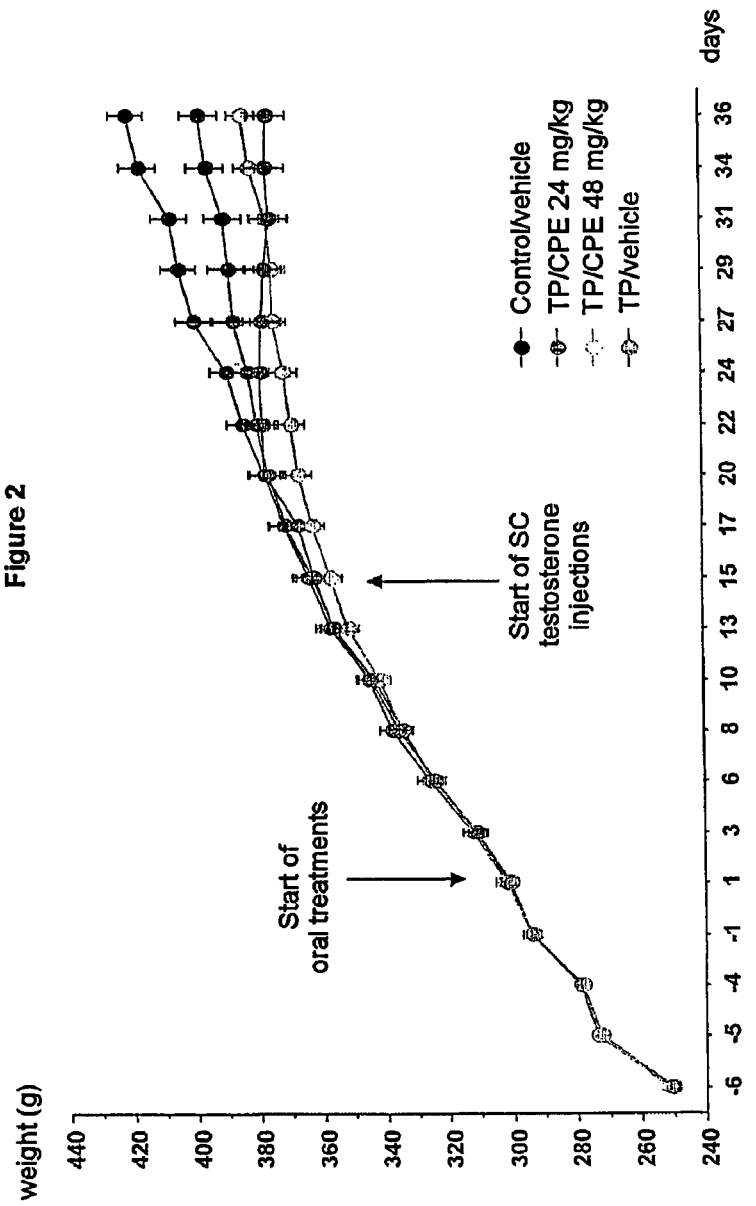
Figure 3:
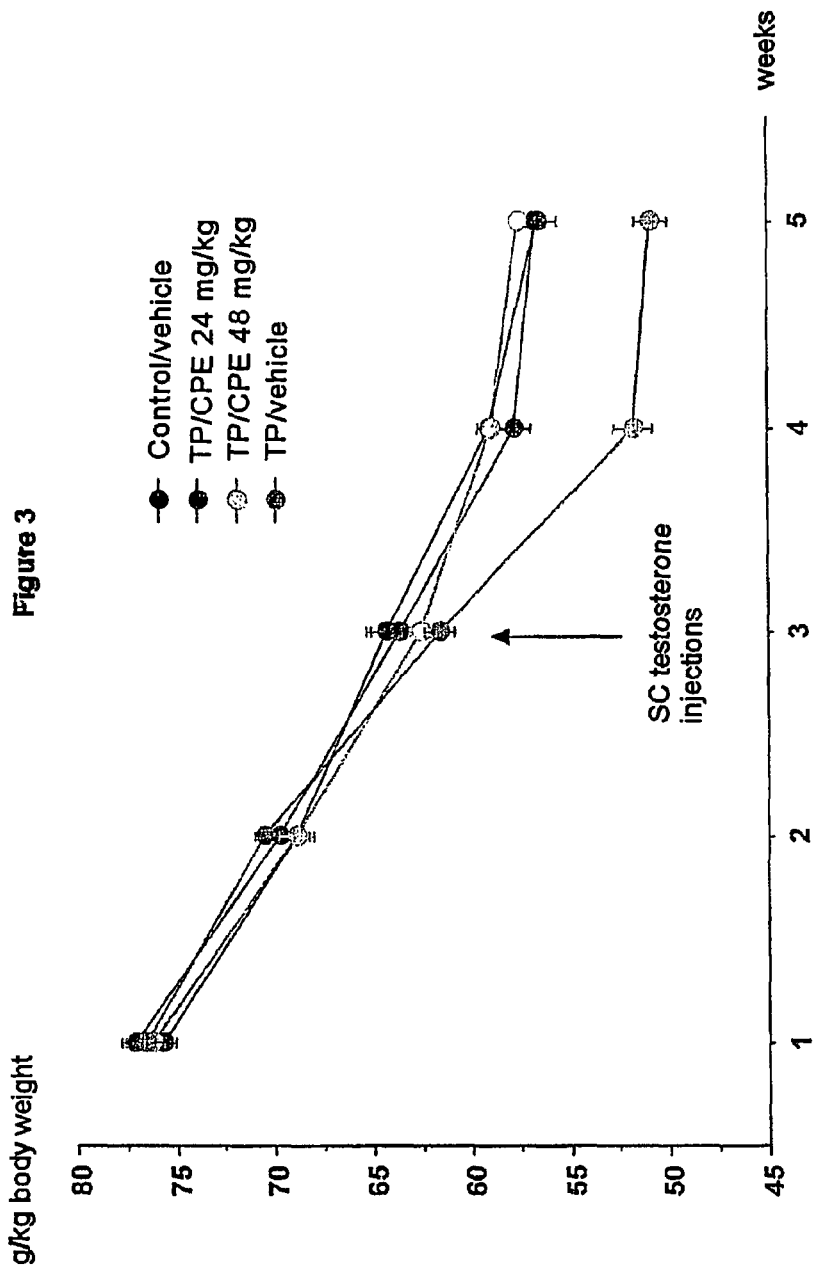
Figure 4:
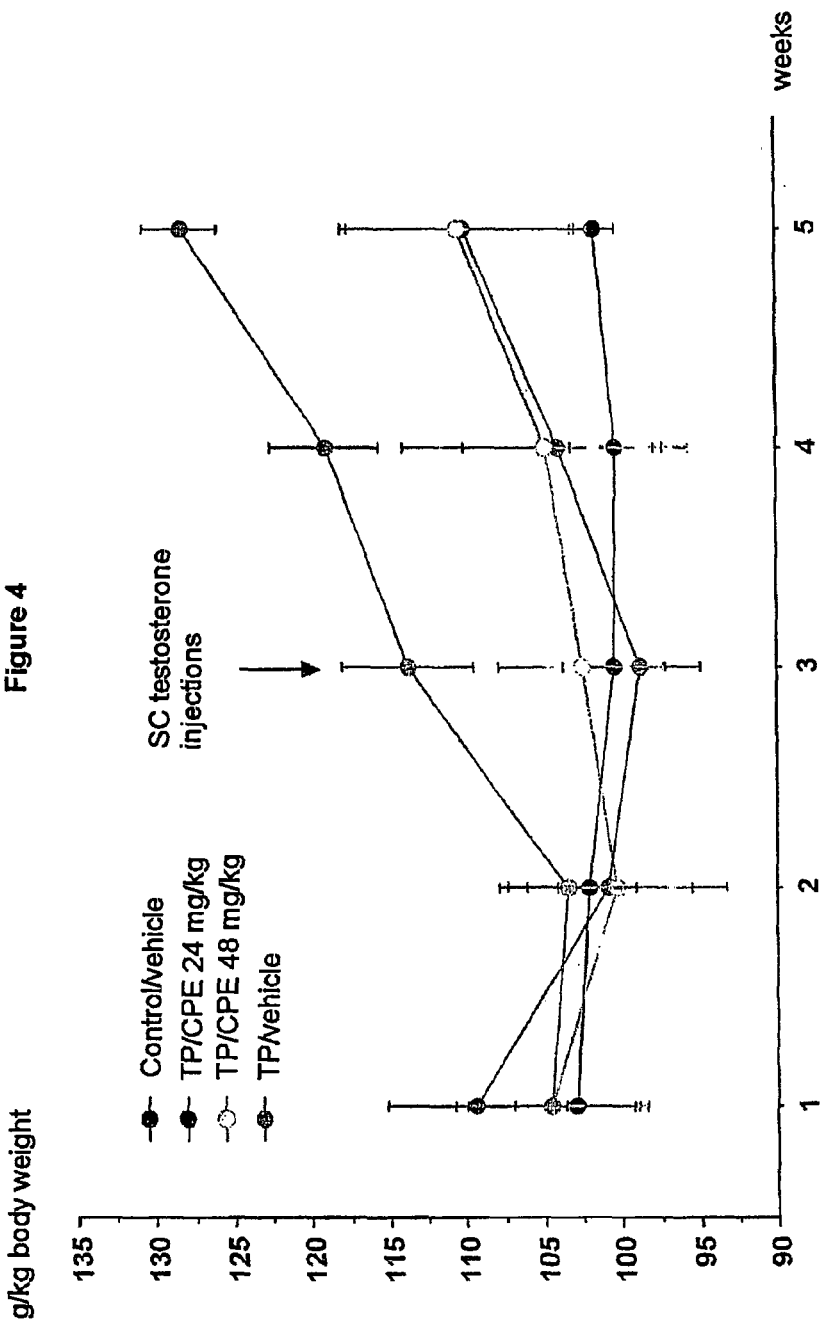
Figure 5:
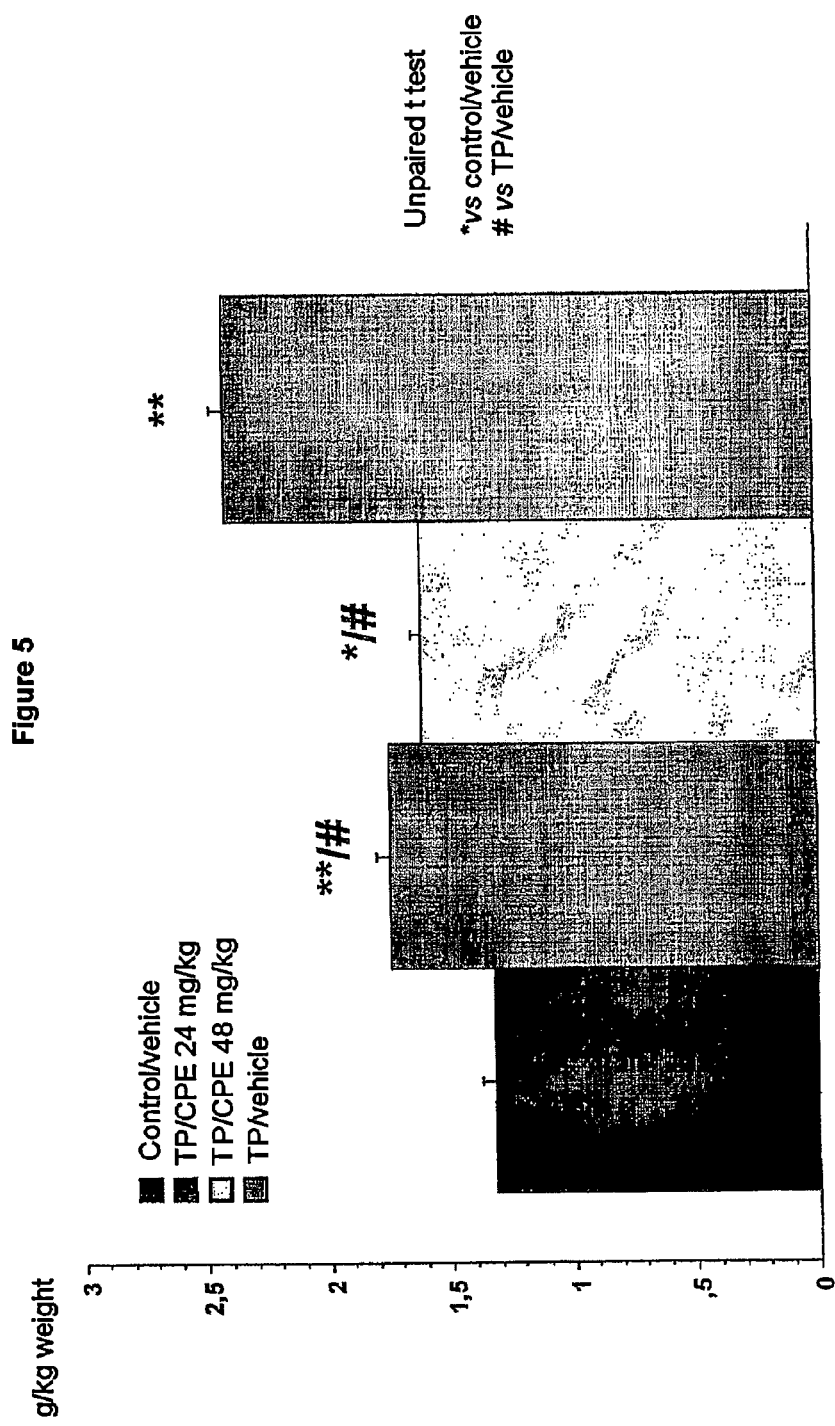
Figure 6:
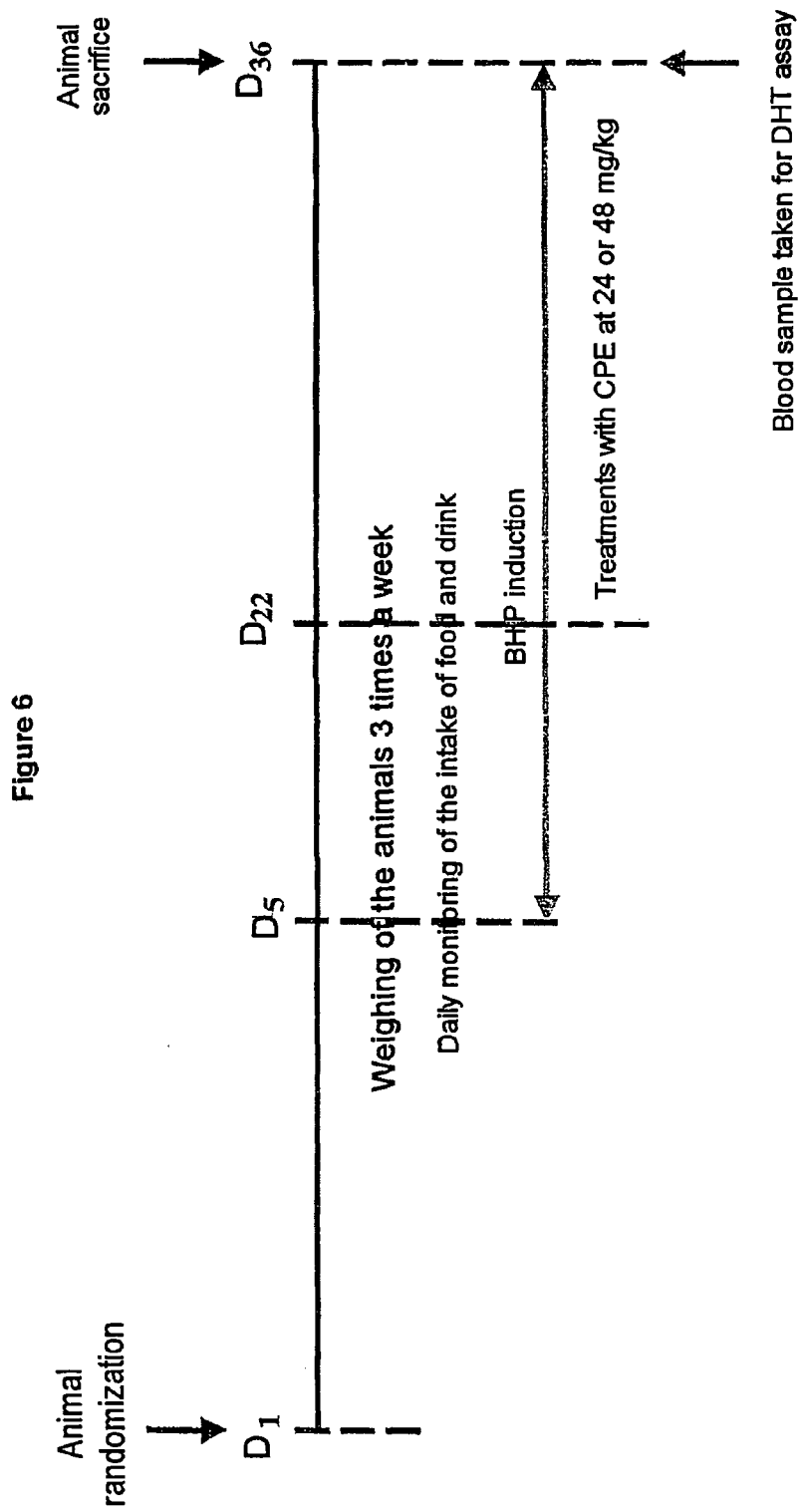
Figure 7:
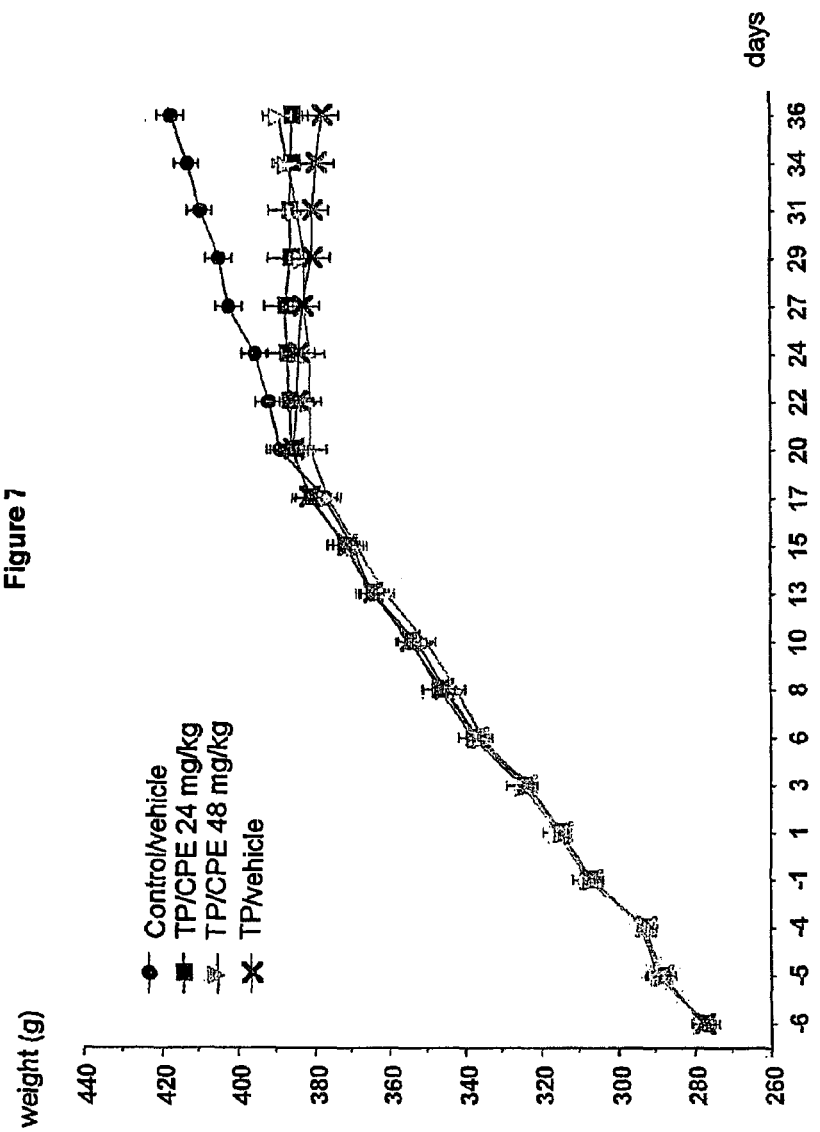
Figure 8:
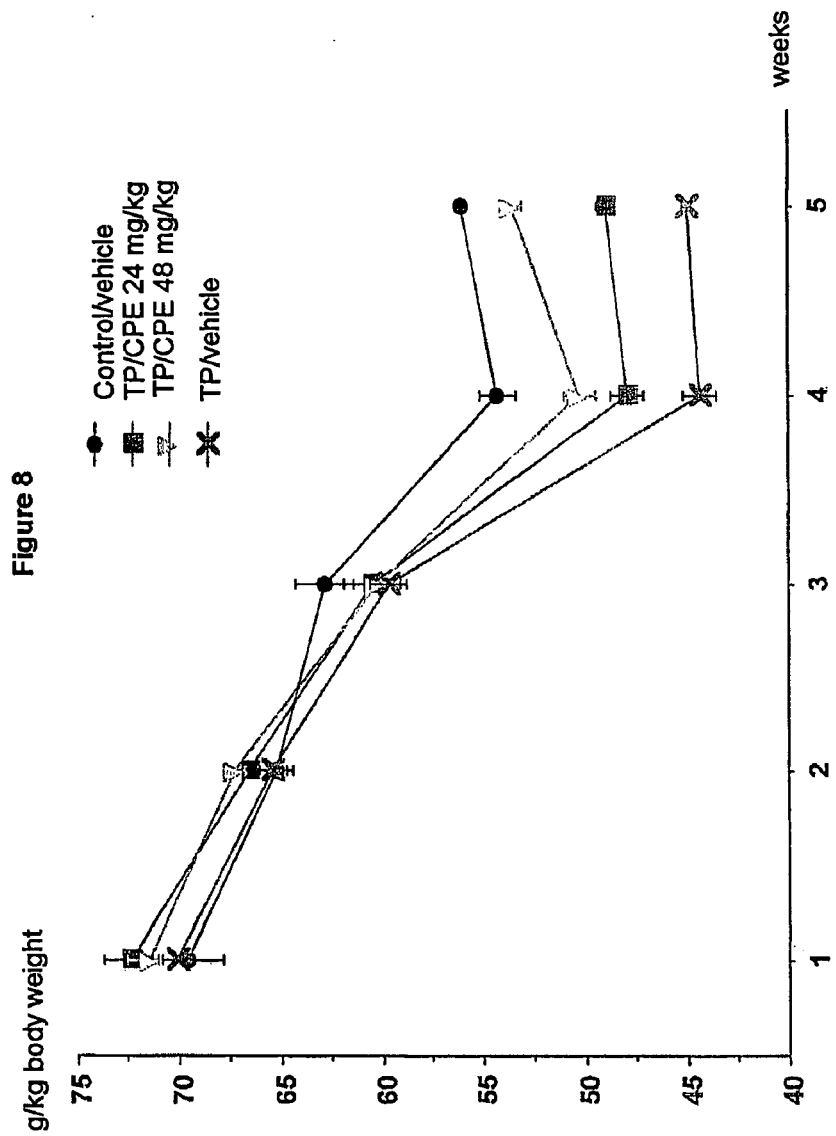
Figure 9:
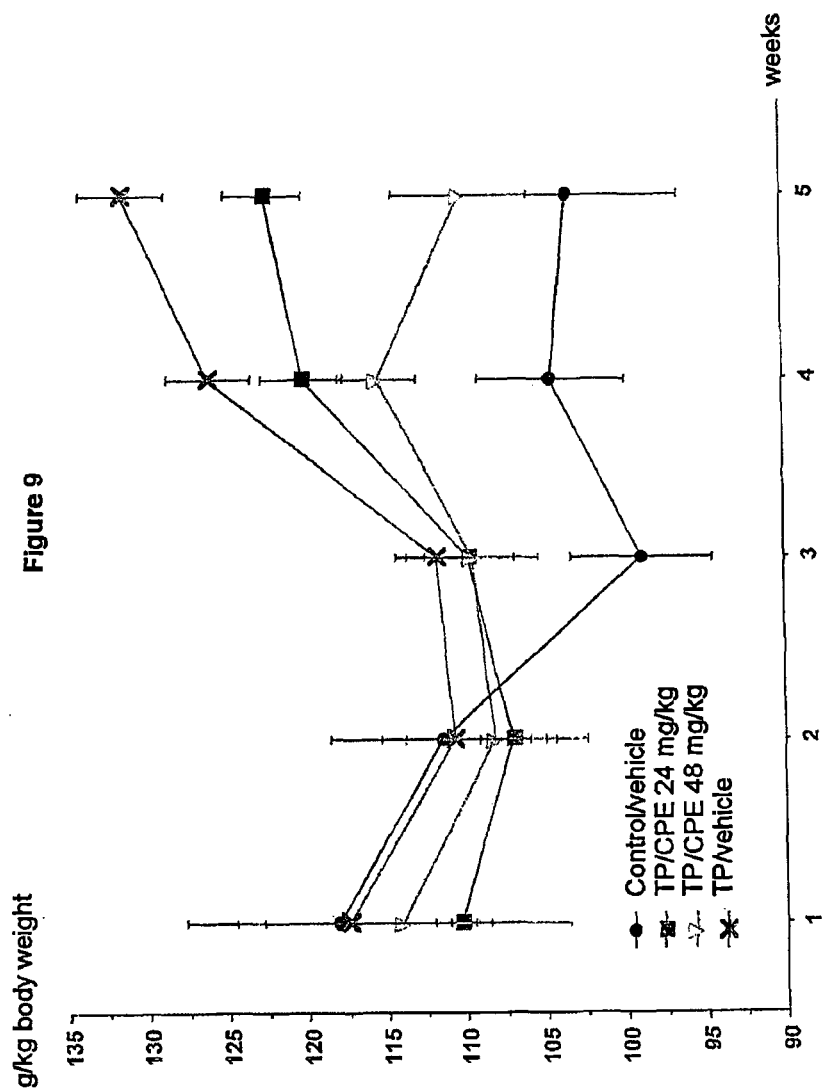
Figure 10:
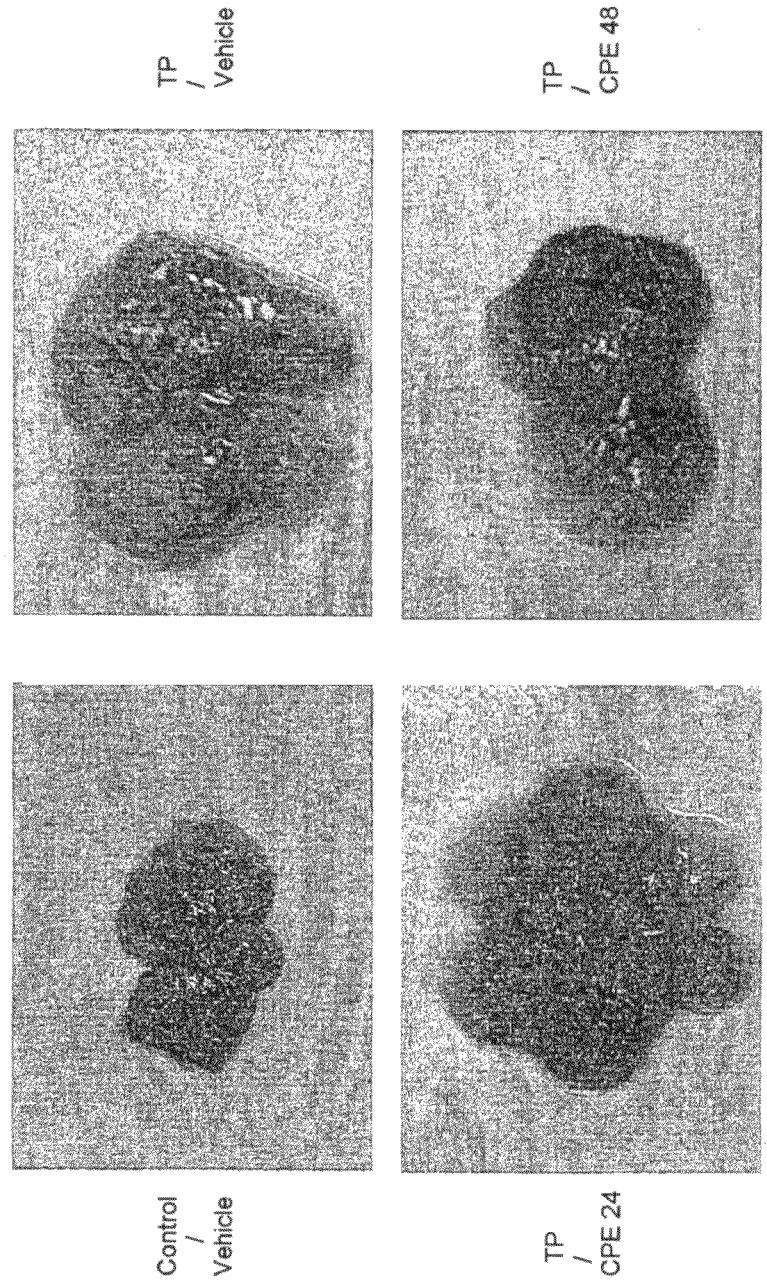
Figure 11:
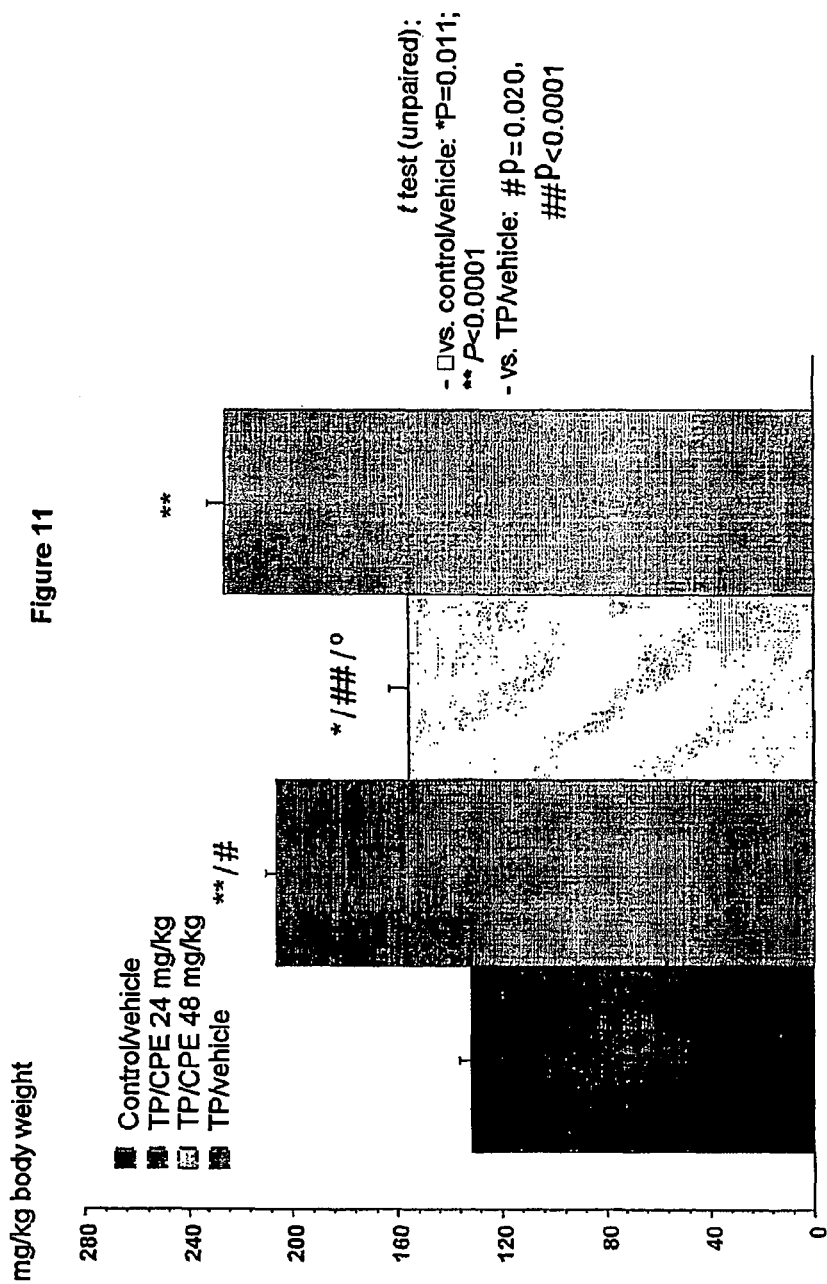
Figure 13:
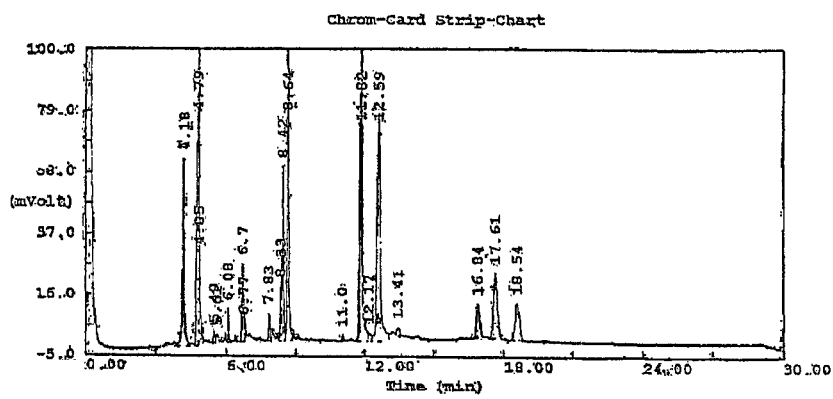
Figure 14:
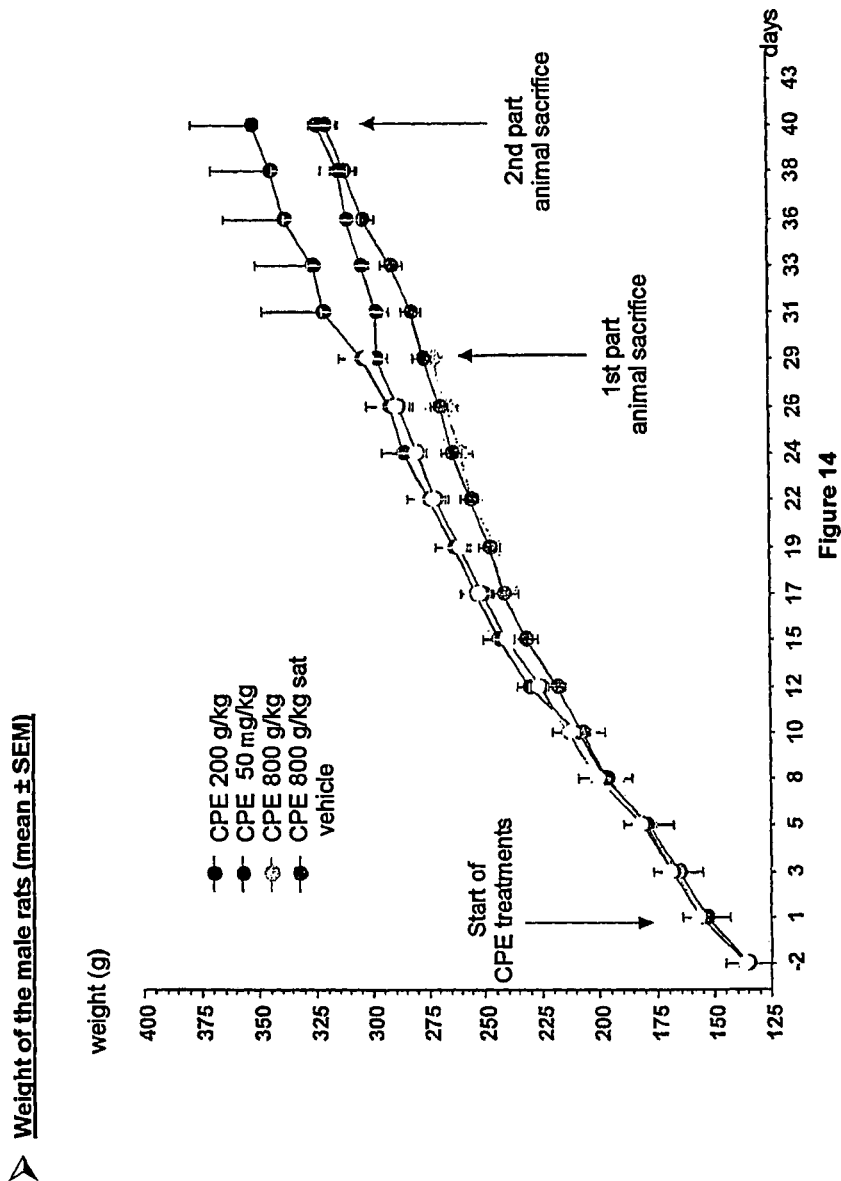
Figure 15:
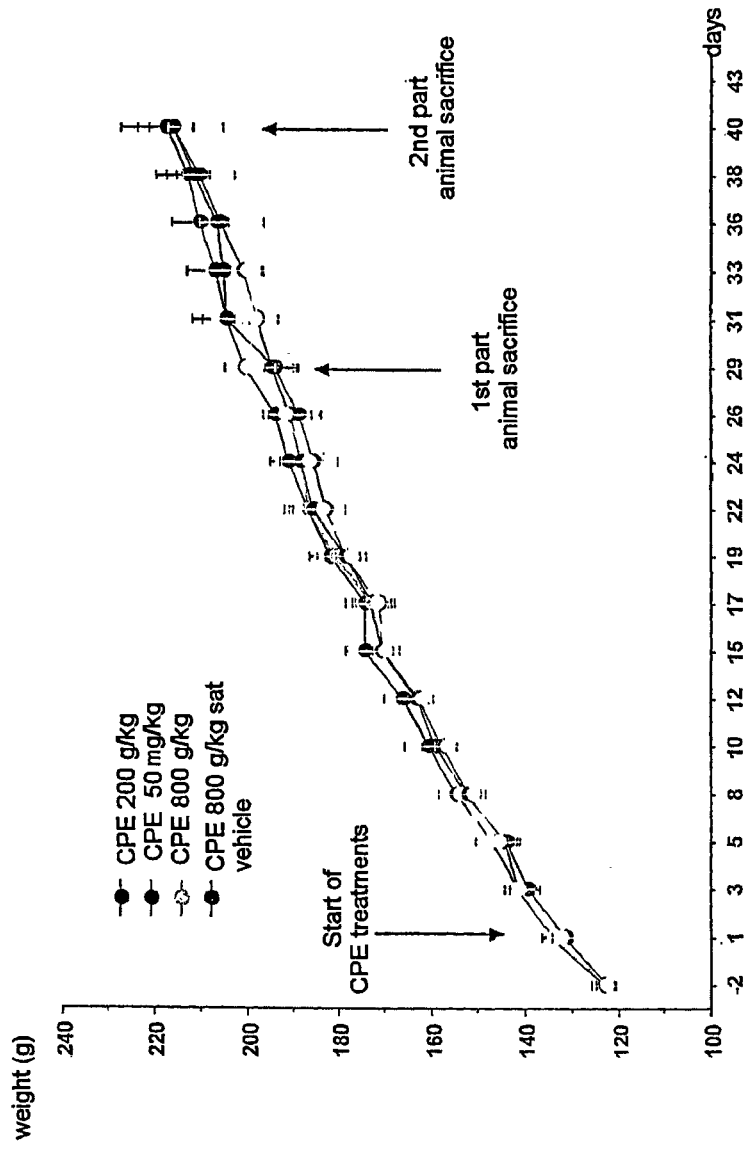
Figure 28:
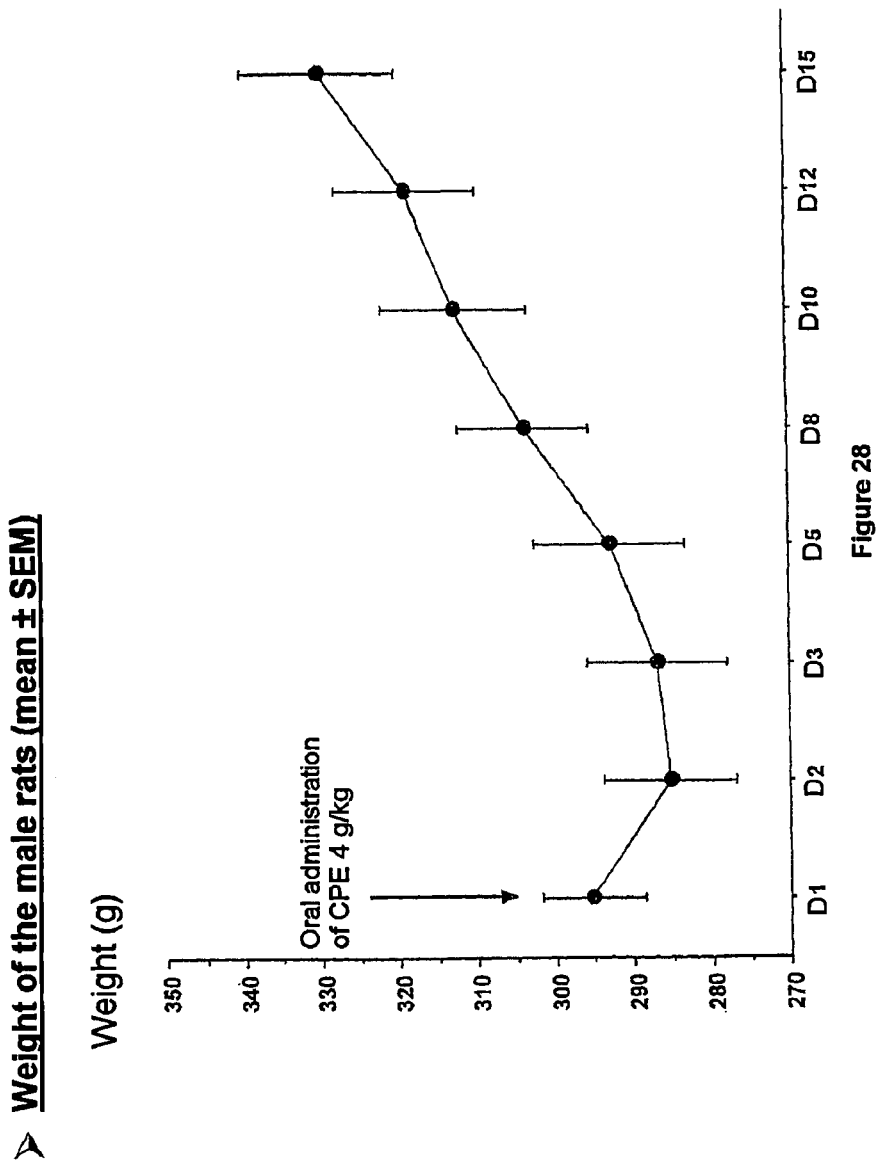
Figure 29:
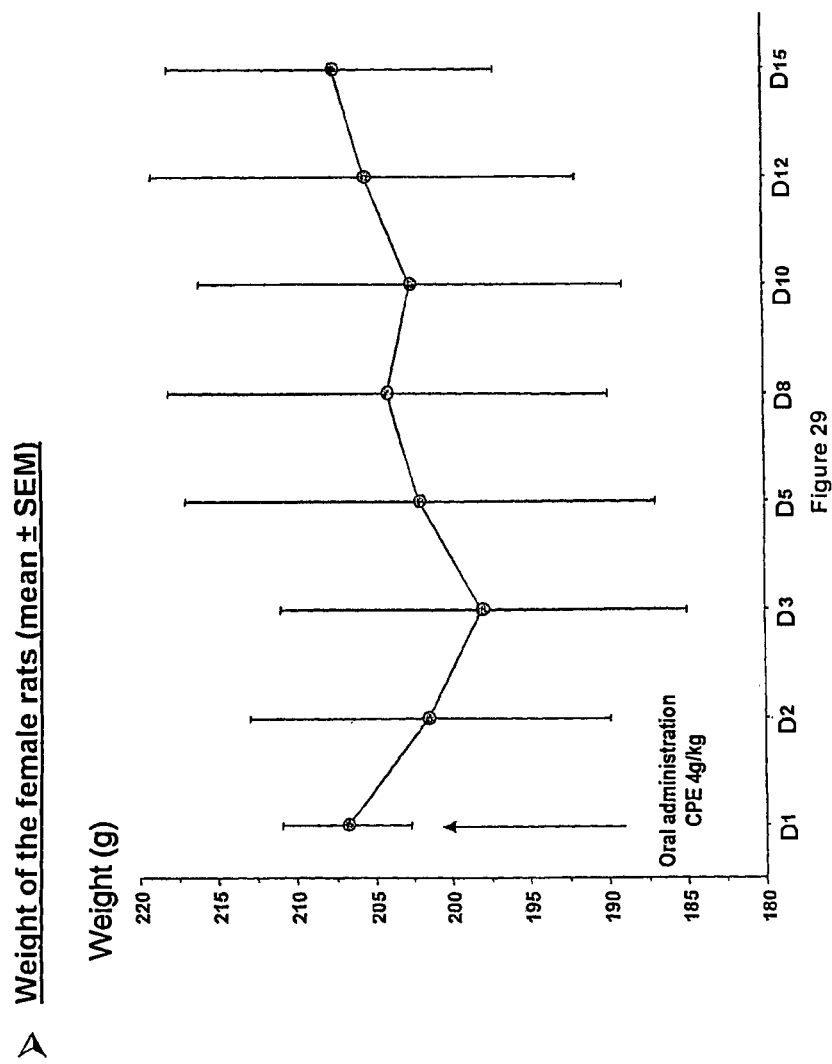
Figure 30:
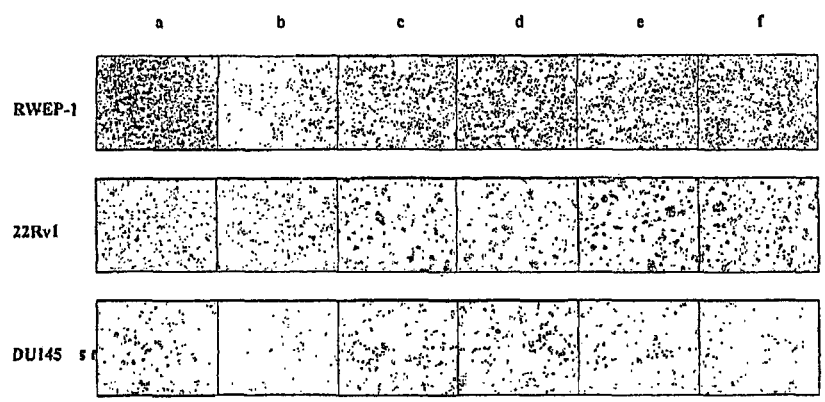
Figure 31:
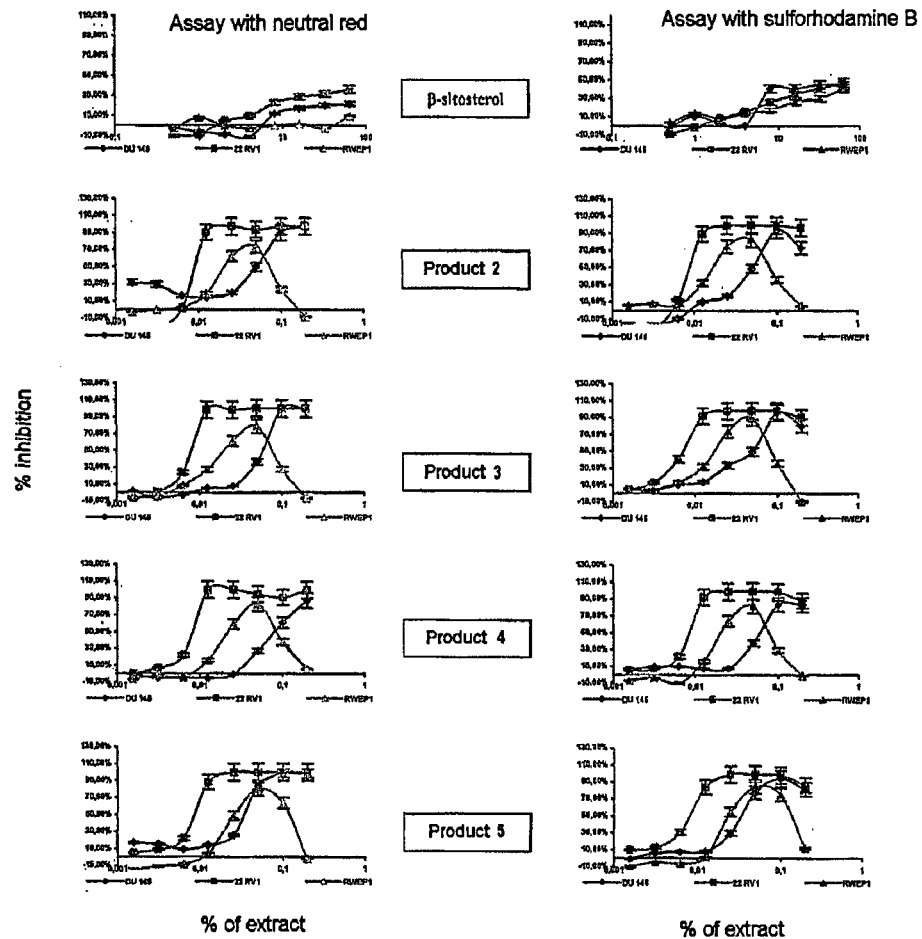
Figure 32:
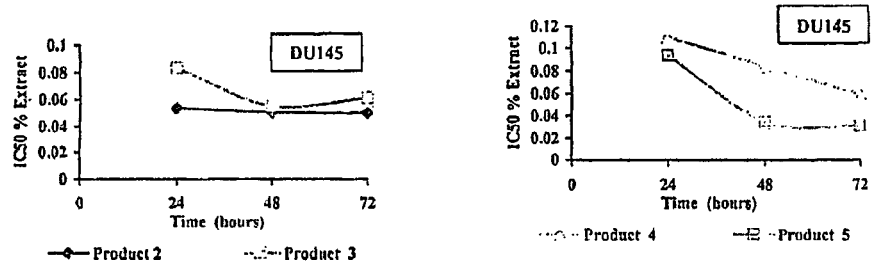
Figure 33:
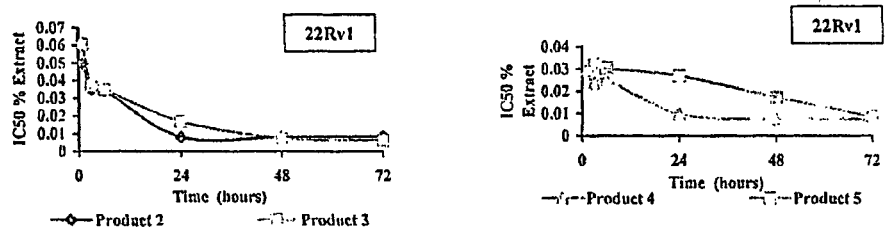
Figure 34:
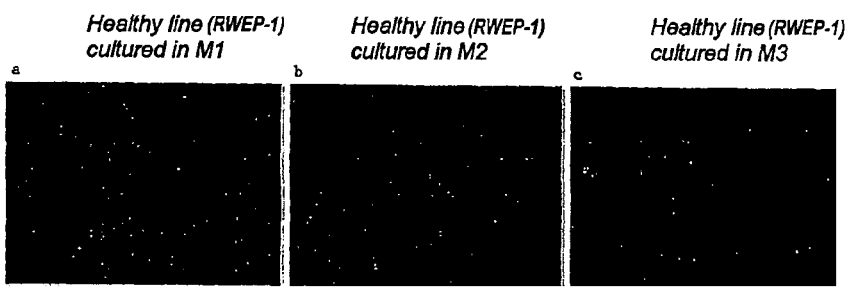
FIGS. 34a, 34b and 34c represent the healthy line (RWEP-1) cultured, respectively, in medium M1 (FIG. 34a), M2 (FIG. 34b) and M3 (FIG. 34c).
Figure 35:
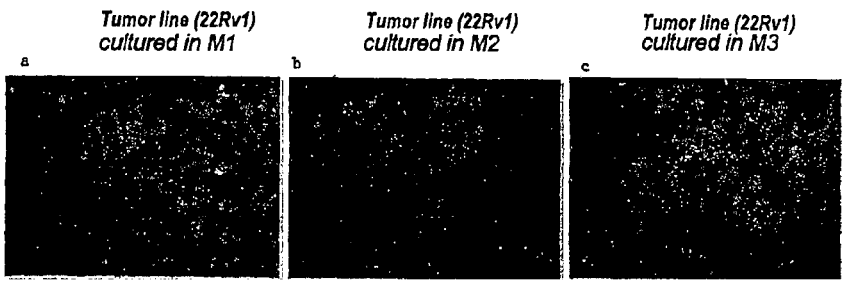
FIGS. 35a, 35b and 35c represent the tumoral line (22Rv1) cultured, respectively, in medium M1 (FIG. 35a), M2 (FIG. 35b) and M3 (FIG. 35c).
Figure 37:
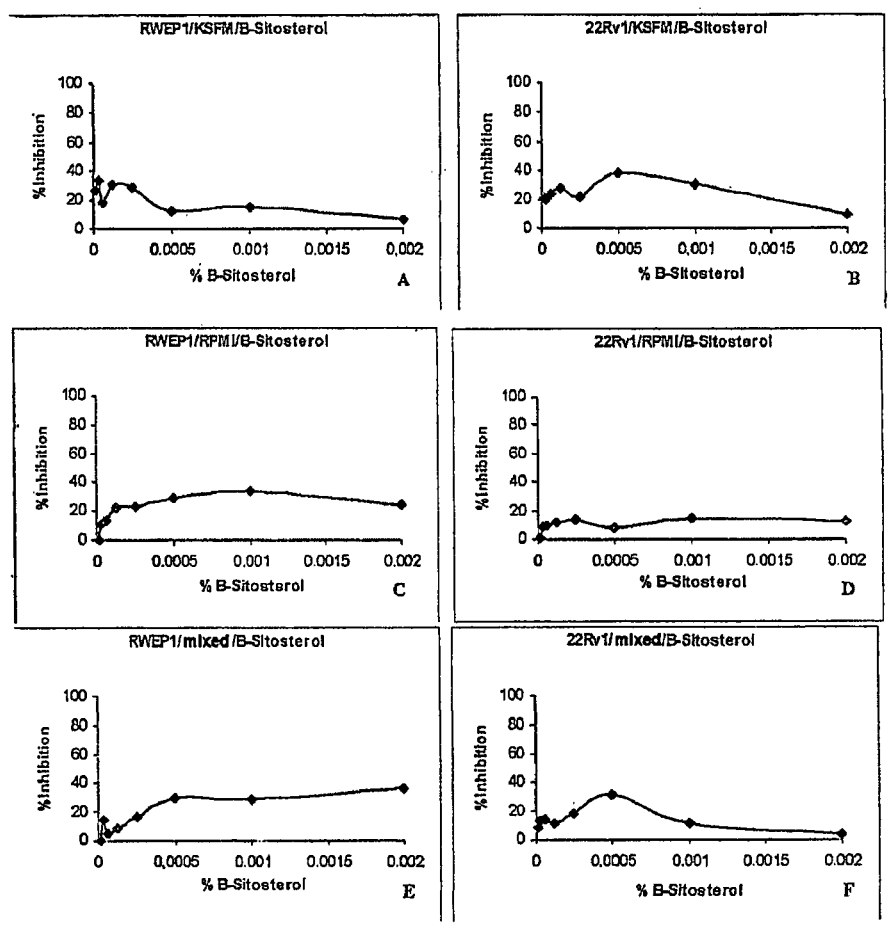

FIGS. 37a and 37b represent the effects of β-sitosterol on the healthy (FIG. 37a) and cancerous (FIG. 37b) human prostate cell lines cultured in medium M1.

FIGS. 37c and 37d represent the effects of β-sitosterol on the healthy (FIG. 37c) and cancerous (FIG. 37d) human prostate cell lines cultured in medium M2.

FIGS. 37e and 37f represent the effects of β-sitosterol on the healthy (FIG. 37e) and cancerous (FIG. 37f) human prostate cell lines cultured in medium M3.

From the results obtained in FIGS. 37a to 37f, β-sitosterol induces a weak inhibition of proliferation of the healthy (RWEP-1) and tumoral (22Rv1) cell lines cultured in the three culture media M1, M2 or M3. The red points represented in FIGS. 37a to 37f correspond to the concentrations selected for the immunolabeling on coculture treated with β-sitosterol, namely $2.5 \times 10^{-4}$% and $1.2 \times 10^{-4}$%.

FIGS. 38a to 38f represent the effects of CPE on the healthy and cancerous human prostate cell lines cultured independently in the media M1, M2 or M3.

Figure 38:
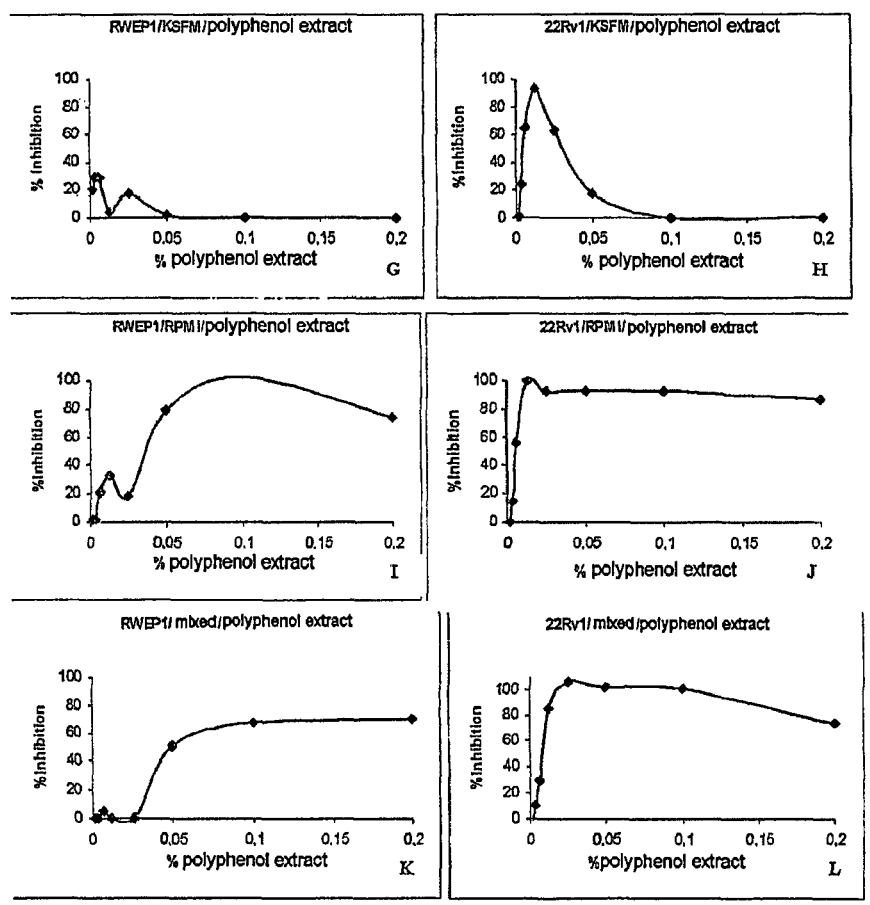

FIGS. 38a and 38b represent the effects of CPE on the healthy (FIG. 38a) and cancerous (FIG. 38b) human prostate cell lines cultured in medium M1.

FIGS. 38c and 38d represent the effects of CPE on the healthy (FIG. 38c) and cancerous (FIG. 38d) human prostate cell lines cultured in medium M2.

FIGS. 38e and 38f represent the effects of CPE on the healthy (FIG. 38e) and cancerous (FIG. 38f) human prostate cell lines cultured in medium M3.

From the results obtained in FIGS. 38a to 38f, a dose-dependent effect of CPE was observed. Furthermore, complete inhibition of proliferation of the tumoral cells with this CPE was observed for the culture conditions in media M2 and M3. This inhibitory effect was induced at the lowest concentrations of CPE, namely 0.025% and 0.0125%. At these same concentrations, CPE induced a weak inhibition of proliferation of the healthy cells (RWEP-1) in medium M2 and no inhibition in medium M3. Medium M3 was thus selected to test the effects of CPE in immunolabeling.

Thus, from the results of this proliferation test via the neutral red release method, medium M3 was selected for immunolabeling on the coculture. Specifically, this mixed medium makes it possible to obtain the same inhibitory effects as those observed in the proceeding study:

CPE induced total inhibition of the tumoral cell proliferation and had no effect on the healthy cell line;

β-sitosterol induced a moderate inhibition of the cell proliferation on both the healthy and tumoral cell lines.

b) Immunolabeling of the Coculture after Treatment

The results of the immunolabeling on coculture after treatment with the reference product (β-sitosterol) and with the test product (CPE) are presented in FIGS. 39a to 39e.

FIGS. 39a to 39e represent the coculture of the tumoral and healthy prostate cell lines treated with β-sitosterol or with CPE in medium M3.

FIG. 39a represents the untreated coculture (=proliferation control) (×20).

FIG. 39b represents the coculture treated with β-sitosterol ($2.5 \times 10^{-3}$%) (×20).

FIG. 39c represents the coculture treated with CPE (0.025%) (×20).

FIG. 39d represents the coculture treated with β-sitosterol ($1.2 \times 10^{-3}$%) (×20).

FIG. 39e represent the coculture treated with CPE (0.0125%) (×20).

During the labeling, the Hoechst stain was also used in order to reveal the healthy and tumoral prostate cell nuclei. The tumoral cells were labeled with the anti-galectin 8 antibody (in green) and with Hoechst; the healthy cells were labeled with Hoechst (in blue).

At the two β-sitosterol concentrations tested ($2.5 \times 10^{-4}$% and $1.2 \times 10^{-4}$%), the area of labeling revealed by immunolabeling and with Hoechst is equivalent to that of the untreated proliferation control. This absence of significant difference in labeling is due to a moderate inhibitory effect of β-sitosterol on the tumoral and healthy cell lines.

At the two CPE concentrations tested (0.025% and 0.0125%), a phenomenon of aggregation of the tumoral cells is observed, greatly reducing the area for labeling. This cell aggregation might explain a higher intensity of labeling related essentially to the accumulation of the primary antibody at the galectin 8 antigenic site of the tumoral cells. This aggregation phenomenon is dose-dependent since the aggregation density and the labeling area are smaller at 0.025% of CPE than at 0.0125%. Proliferation of the tumoral cell line is effectively inhibited (see the above paragraph regarding the neutral red release method) but still shows the antigen in its integrity since this cell line has been labeled.

3) Conclusion

The two CPE concentrations tested (0.025% and 0.0125%) induce a cell proliferation inhibition of about 90% without inhibiting the healthy cells and also allow a reduction in the adhesion of the tumoral cells and of the total surface area of the tumoral cell lawn. This high percentage of proliferation inhibition and this capacity to limit the adhesion of the tumoral cells are not observed for the reference product, β-sitosterol. The difference in biological effect between β-sitosterol and CPE is markedly visualized by fluorescence, by immunolabeling. Thus, by observing these images, CPE, in addition to its capacity to inhibit the proliferation of tumoral cells, makes it possible to reduce the adhesion of these cells.

EXAMPLE 8

Chemopreventive Effect of the Cocoa Polyphenol Extract (CPE) According to the Invention in Rats The model of prostate carcinogenesis using the direct-action chemical carcinogen, namely N-methyl-nitrosourea (MNU), followed by chronic androgen stimulation with testosterone in Wistar-Unilever rats, has been used in several recent chemoprevention studies. This is a pertinent model from the anatomical and physiological point of view for the preclinical evaluation of substances that are assumed to inhibit or reinforce prostate carcinogenesis in man.

In this example, the chemopreventive effects of the cocoa polyphenol extract (CPE), administered orally to Wistar-Unilever rats at doses of 24 and 48 mg/kg, against chemically-induced prostate tumors were evaluated.

Treatment of the rats with CPE administered at a dose of 24 mg/kg inhibited the development of prostate tumors with histological characteristics similar to those of clinical human prostate cancer.

2. Materials and Methods

Chemical Substances

The carcinogen MNU (N-methylnitrosourea) and an androgenic hormone, testosterone propionate (TP) (CAS No. 57-85-2) were obtained from Sigma-Aldrich (Saint-Quentin Fallavier, France).

Solvent-free CPE was supplied by Barry Callebaut France (Louviers, France). It was isolated from Ivory Coast cocoa beans by extraction, filtration and drying. The total polyphenol composition of this extract is 88.5% procyanidins and 11.5% catechin, epicatechin and epicatechin gallate.

Animals

Seventy-five male Wistar-Unilever rats (HsdCpb:WU), weighing from 250 to 275 g at the start of the experiment, were obtained from Harlan Nederland (Horst, Netherlands) and were divided into 5 groups of 15 rats each. They were housed in polypropylene cages (3 rats per cage) equipped to provide them with food and water. The animals were kept in an air-conditioned room under conditions of controlled temperature (22±2° C.) and relative humidity (50±10%), with an inverted 12-hour day/night cycle (light switched off at 8 am). They had access to a standard M20 diet (Dietex, France) and to tap water ad libitum. The animal station has the authorizations granted by the French Ministries of Agriculture and of Research and the animal experiments were performed in accordance with the European recommendations on animal experimentation (Directive of the European Community Council No. 86/609, 1986) and the British guidelines of the wellbeing of animals in the context of experimental neoplasty.

Induction of Prostate Tumors

The induction of prostate tumors was performed in two phases. For the initiation phase, the rats received a single intravenous injection, into the caudal vein, of the carcinogen MNU at a rate of 35 mg/kg of body weight prepared with a sterile saline solution immediately before injection. The controls received only a single intravenous injection of sterile saline solution. For the development phase, one week after the administration of MNU, the rats received a subcutaneous implant of a silastic tube (Sani-Tech® 50, Saint-Gobain Performance Plastics, Tauton, Mass., USA) 2 cm long filled with 40 mg of PT and hermetically closed with a medical adhesive bond (3M Vetbond™, St. Paul, Minn., USA). The silastic tube was installed by making a small incision in the subcutaneous space inside the area of the abdominal ventral wall of the rats under anesthesia with acepromazine (2 mg/kg of CalmiVet, Vetoquinol, Lure, France) with ketamine (50 mg/kg of ketamine 1000, Virbac, Carros, France). The silastic tube was replaced every two months over the first six months of the experiment. On the controls, hermetically closed empty silastic tubes were implanted.

Treatments

After a seven-day acclimatization period counting from the day of their arrival, the 75 male Wistar-Unilever rats were randomized in 5 groups of 15 rats each as a function of their body weight.

A control group was chemically induced and was not treated ("no treatment" group).

Another control group received an intravenous injection of sterile saline solution, subcutaneous implants of empty silastic tubes and was treated with a vehicle (spring water) (group "no induction+vehicle").

The other three groups of rats were subjected to an induction of prostate tumors in accordance with the protocol described above and were treated with CPE at a rate of 24 or 48 mg/kg of body weight ("chemo-induced+CPE 24" and "chemo-induced+CPE 48" groups, respectively) or with a vehicle ("chemo-induced+vehicle" group). The treatments with CPE and the vehicle started two weeks before the administration of MNU. The CPE was dissolved in the vehicle each day before being administered to the animals. The CPE and the vehicle were administered orally as a function of the body weight of the rats, every week from Monday to Friday, throughout the experiment.

Monitoring of the Animals and Autopsy

The viability, behavior and body weight of the rats were recorded three times a week throughout the experiment. The consumption of food and water were recorded each week, from Monday to Friday, for each cage in order to estimate the amount of food and water ingested by the rats housed in the cages. During the experiment, animals were sacrificed under anesthesia if they showed signs of suffering (cachexia, weakness, difficulty in moving or in feeding), of toxicity associated with the compounds (gibbosity or convulsions), or a 25% loss of body weight over three consecutive days. An autopsy was performed in each case.

Nine months after induction of the prostate tumors, six rats from each group were sacrificed under anesthesia in order to perform a histopathological evaluation. The remaining nine rats in each group were maintained in a survival study and were treated as described above.

Histopathological Evaluation

During the autopsy, all the pronounced lesions were excized. The appended sexual glands and the urinary bladder were carefully removed in one piece from each rat and fixed in 4% formalin solution (Roti®-Histofix 4%, Carl Roth GmbH & Co., Germany). After fixing, the appended sexual glands were embedded in paraffin and thin slices (5.0 μm thick) were prepared from all the blocks and stained with hematoxylin and eosin for histopathological evaluation. The slices were evaluated blind and independently twice by the same researcher in order to classify the lesions. The lesions of the prostate and of the seminal vesicles were catalogued as inflammation, hyperplasia (focal or diffuse), adenocarcinoma and lymphoma.

Statistical Analysis

Analysis of variance (ANOVA) was used to compare the mean body weight change (MBWC) and the consumption of food and water for the five groups of rats. When a significant event was observed, the analysis of variance (ANOVA) was followed by a post hoc Scheffé test in order to compare the chemo-induced groups with the control groups. The results were expressed in the form of a calculation of standard deviation± of the mean (SEM). For all the comparisons, the differences were considered as significant at $P<0.05$. All the statistical analyses were performed using the StatView®5 statistical software (SAS Institute Inc., Cary, N.C., USA).

2. Results

Mean Body Weight Change of the Rats

All the animals remained in good health throughout the experimental period.

Figure 40:
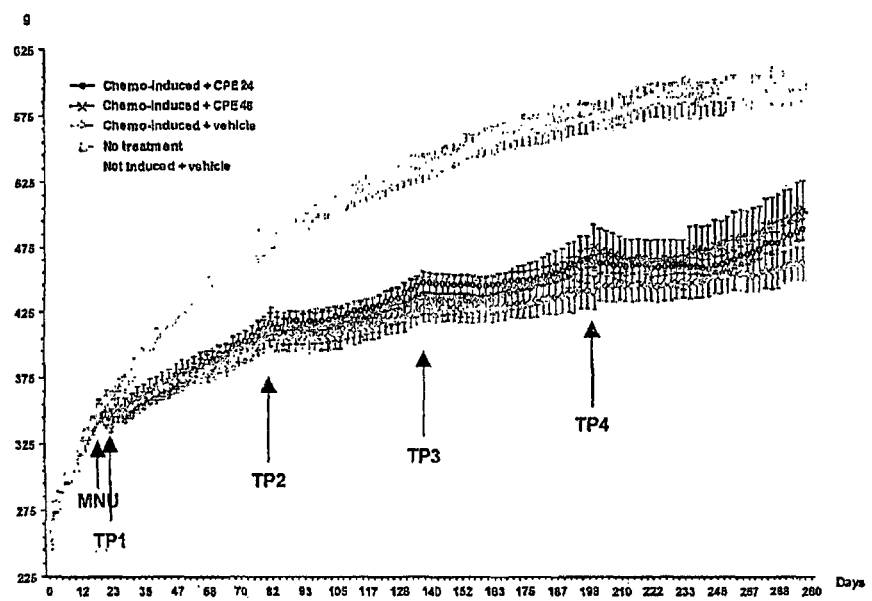

As shown in FIG. 40, the body weight gains for the five groups of rat were not statistically different for the first two weeks of the treatments, before induction of the prostate tumors (between D5 and D19). After induction of the prostate tumors (between D19 and D278), the body weight gain of the "no treatment" (+249.9±27.0 g) and "no induction+vehicle" (+250.6±28.7 g) groups were considerably higher than those for the "chemo-induced+vehicle" (+116.1±23.1 g), "chemo-induced+CPE 24" (+140.3±17.6 g) and "chemo-induced+CPE 48" (+147.1±50.3 g) groups ($P<0.0001$ in all cases). This difference in body weight gain is due to the combined treatments of MNU and of TP. No statistical difference in the body weight gains was observed between the "no treatment" and "no induction+vehicle" groups or between the "chemo-induced+vehicle", "chemo-induced+CPE 24" and "chemo-induced+CPE 48" groups over the same period. However, the body weight gains for the "chemo-induced+CPE 24" and "chemo-induced+CPE 48" groups were greater than those for the "chemo-induced+vehicle" group.

Consumption of Food and Water by the Rats

Figure 41:
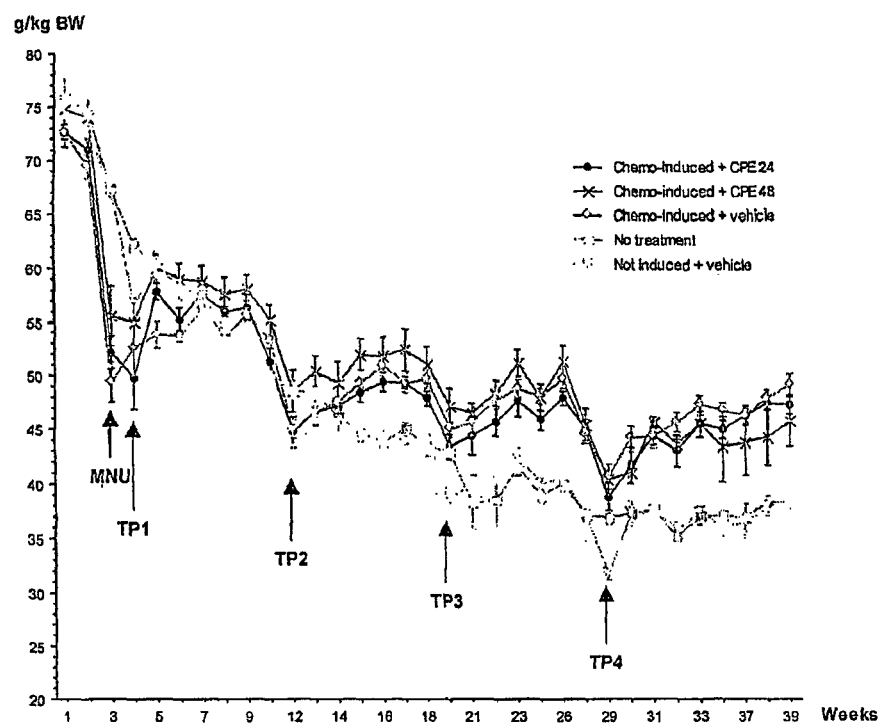

As shown in FIG. 41, the consumption of food by the "chemo-induced+vehicle" group (50.0±0.5 g/kg/day) was significantly higher than that for the "no treatment" (46.8±0.9 g/kg/day) and "no induction+vehicle" (46.1±1.2 g/kg/day) groups ($P=0.019$ and $P=0.003$, respectively). The mean food consumption for the "chemo-induced+CPE 24" group (49.5±1.3 g/kg/day) was significantly higher than that for the "no induction+vehicle" group ($P=0.011$). The mean food consumption for the "chemo-induced+CPE 48" group (51.4±1.0 g/kg/day) was significantly higher than that for the "no treatment" and "no induction+vehicle" groups ($P=0.0007$ and $P=0.0001$, respectively). No significant difference was observed in the mean food consumption between the "no treatment" and "no induction+vehicle" groups and between the "chemo-induced+vehicle", "chemo-induced+CPE 24" and "chemo-induced+CPE 48" groups.

Figure 42:
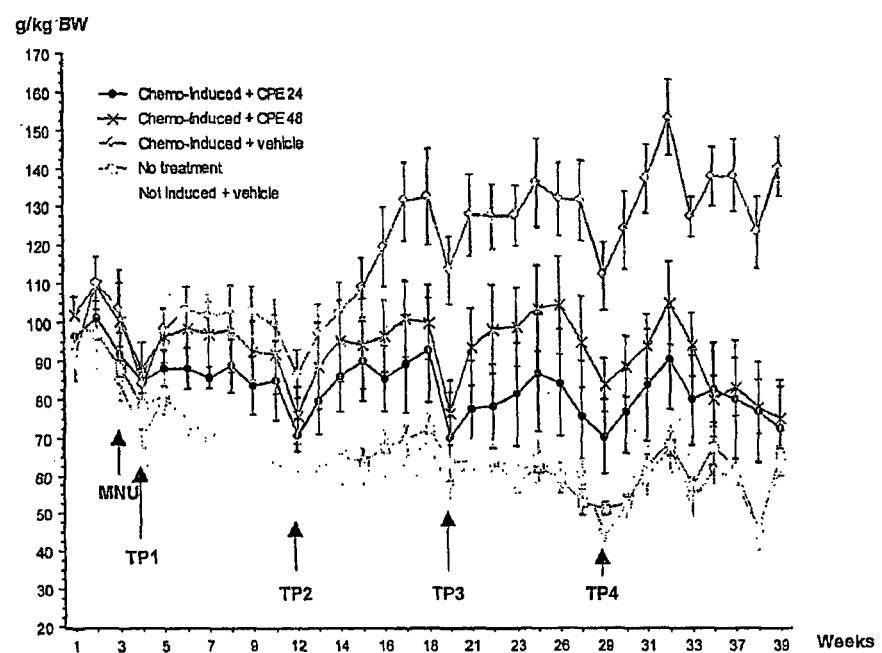

As indicated in FIG. 42, the mean water con-sumption for the "chemo-induced+vehicle" group (117.2±12.9 g/kg/day) was significantly higher than that for the "chemo-induced+CPE 24" (83.4±16.2 g/kg/day), "no treatment" (66.8±3.3 g/kg/day) and "no induction+vehicle" (64.4±6.9 g/kg/day) groups ($P=0.028$, $P=0.0007$ and $P=0.0004$, respectively). No significant difference was observed in the water consumption between the "chemo-induced+vehicle" and "chemo-induced+CPE 48" groups (93.3±13.3 g/kg/day). No statistical difference in the mean water consumption was observed between the "chemo-induced+CPE 24", "chemo-induced+CPE 48", "no treatment" and "no induction+vehicle" groups.

Incidence of the Prostate Lesions

TABLE 4

Incidence of the prostate lesions after nine months

| Treatment | Number of rats examined | Inflammation | Focal hyperplasia | Diffuse hyperplasia | Adenocarcinoma | Lymphoma |
| --- | --- | --- | --- | --- | --- | --- |
| Chemo-induced + vehicle | 6 | 4 | 1 | 3 | 2 | 2 |
| Chemo-induced + CPE 24 | 6 | 2 | 1 | 2 | 0 | 0 |
| Chemo-induced + CPE 48 | 6 | 4 | 1 | 3 | 1 | 1 |
| Not induced | 6 | 1 | 1 | 1 | 0 | 0 |
| Untreated | 6 | 0 | 1 | 1 | 0 | 0 |

Table 4 above summarizes the data regarding the incidence of prostate lesions observed nine months after the start of treatments with the vehicle or CPE at a rate of 24 or 48 mg/kg and the induction of prostate tumors with MNU and TP. The highest incidence of prostate neoplasty was observed in the "chemo-induced+vehicle" group, where two of the six rats showed adenocarcinomas and two other rats had lymphomas of prostate origin. Four prostate inflammations and three diffuse hyperplasias were also observed in this group. The lesions induced by the combined treatments of MNU and TP appear to occur in the dorsolateral and/or anterior prostate. A reduction of the incidence of prostate neoplasty was observed in the "chemo-induced+CPE 48" group, where one adenocarcinoma and one lymphoma were observed in the dorsolateral and/or anterior prostate in two rats. The same number of prostate inflammations and of diffuse hyperplasias (four and three, respectively) was observed in this group, as for the "chemo-induced+vehicle" group. No adenocarcinomas and no lymphomas were observed in the "chemo-induced+CPE 24" group, as for the two "no treatment" and "no induction+vehicle" groups. Only two prostate inflammations and two diffuse hyperplasias were observed in the "chemo-induced+CPE 24" group, whereas only one prostate inflammation was observed in the "no induction+vehicle" group and one diffuse hyperplasia was observed in both the "no treatment" and "no induction+vehicle" groups. A focal hyperplasia was observed in the five groups of rats. No tumors were observed in the seminal vesicles or in tissues other than the appended sexual glands in all the groups of rats, nine months after induction of the prostate tumors.

3. Conclusion

→ The CPE of the invention, administered orally to rats before the induction of a prostate carcinogenesis and for the nine months following, significantly reduces the incidence of prostate lesions, particularly at the low dose of 24 mg/kg. This is the first time, to the Inventors' knowledge, that it has been shown that a CPE exerts inhibitory effects on prostate carcinogenesis induced chemically in rats.

The treatments with CPE, at doses of 24 and 48 mg/kg, increased the body weight gain of the rats in comparison with the treatments using a vehicle, but with a significantly smaller body weight gain in comparison with the control groups.

The treatments with CPE also led to a reduction in the consumption of food and water by the rats after induction of prostate tumors, in comparison with the treatments using a vehicle.

However, no effect was observed associated with the dose of the treatment with CPE in the number of prostate lesions, nine months after the induction of prostate tumors. A larger number of tumors was observed in the dorsolateral and/or anterior prostate of the rats treated with CPE at a rate of 48 mg/kg per dose than in the group treated at a rate of 24 mg/kg.

The effects of diffusion of TP by means of silastic tubes and its activity in the body of the rats should imperatively be limited by the action of low doses of CPE. CPE administered at a rate of 24 mg/kg can inhibit 5α-reductase, thus limiting the conversion of testosterone to dihydrotestosterone, as reported by Willis and Wians in 2003, and can thus slow down the growth of prostate tumors, which are androgeno-dependent, during the first months. A higher dose of CPE, namely 48 mg/kg, may involve a regulation mechanism such as a negative feedback liable to slow down over time the inhibitory activity of CPE on a 5α-reductase, and with the combination of the carcinogen MNU, risks increasing the development of prostate tumors instead of inhibiting them. These observations may explain the fact that the consumptions of food and water by the rats of the group treated with CPE 48 are higher than those for the group treated with CPE 24 and closer to those for the group treated with a vehicle for the first eight months.

In this example, the efficacy of CPE appears to be inversely related to the dose although it may be assumed that its bioavailability is dose-dependent.

It was indicated, in a previous study, that the bioavailability of epicatechin showed dose dependency in the range of doses examined (1 to 10 mg/kg of body weight). 30% to 50% of epicatechin administered orally were absorbed via the digestive tract and distributed in the blood in conjugate form and showed antioxidant activity in the blood of rats.

The same observation was made, in an even earlier study, in humans after high consumption of various amounts of a procyanidin-rich chocolate. In 2003, it was shown by Record et al. that the consumption of chocolate comprising either 200 mg of flavonoids or of related procyanidins reduced the production of free radicals in the fecal water, which suggested the efficacy of chocolate-derived polyphenols on the health of the intestine.

The strong anti-proliferative effect of cocoa flavonoids and procyanidins on human colon cancer cells has also been described. The efficacy of the anti-proliferative and anti-tumoral properties of flavonoids and procyanidins is quite probably associated with their degree of polymerization. It has been reported that the antioxidant properties of these compounds present in cocoa and chocolate may be affected by the length of the oligomer chain.

In other studies, it has been shown that cocoa liquor polyphenols inhibit the growth of tumors induced with 12-O-tetradecanoylphorbol 13-acetate, thus suggesting anti-proliferative and anti-inflammatory mechanisms. Subjecting male rats to a diet containing cocoa liquor polyphenols has been associated with a significant inhibition of lung carcinogenesis and a tendency in favor of inhibition of thyroid carcinogenesis.

Given the results of the present example and of those of the other studies, it appears that the daily consumption of small amounts of flavonoids and procyanidins originating from cocoa or chocolate, together with a usual intake of flavonoids originating from other food sources, is liable to contribute toward protecting against carcinogenesis in various organs, including the prostate.

In conclusion, the treatments with CPE at a rate of 24 mg/kg per dose protects rats against chemo-induced prostate tumors when they are administered before the induction initiation phase.

EXAMPLE 9

Effects of Cocoa Polyphenol Extracts (CPE) on the Cognitive Performance of Rats after a Heat Stroke The object of this example is to evaluate the preventive antioxidant effects of two cocoa phenol extracts (CPE1 and CPE2) on the increase of free radicals in circulation after a heat stroke in male Wistar rats and their protective effects on the cognitive performances.

Several authors have observed that a prolonged heat stroke in rats induces cerebral ischemia, including lesions in the cerebellum, the cortex, the striatum and the thalamus and oxidative stress with overproduction of circulating free radicals in the form of nitric oxide.

Large amounts of reactive oxidative species cause brain damage and the rats have difficulties in learning and memorizing. The light extinction test is used to evaluate the capacity of rats to distinguish between an active lever and an inactive lever in a situation of operative conditioning. The water labyrinth test is used to determine the short-term and long-term spatial memorization in rats. Rats comprising large amounts of circulating free radicals are incapable of passing this test in a short time and of memorizing it correctly.

To evaluate the preventive effects of cocoa polyphenols on the production of free radicals after a heat stroke, rats are treated daily orally with two CPEs (CPE 1 and CPE 2) for 14 days before exposure to a heat stroke (40° C., 120 minutes). Two learning tests are used to evaluate the preventive effects of the products on cognitive deficiency: the light extinction test and the Morris water labyrinth test. The free radicals are determined in the serum after a heat stroke and the rats are tested in the cognitive tests to evaluate their performances in comparison with two control groups (treated with a vehicle, with or without a heat stroke). Vitamin E (α-tocopherol) administered daily orally at a rate of 200 mg/kg of body weight/day is used as a reference antioxidant.

It was observed that the content of free radicals in the blood of the rats treated with CPE1, CPE2 or vitamin E and then exposed to a heat stroke is markedly lower than in control rats. The rats treated with CPE1 or CPE2 showed a smaller total number of lever presses in the light extinction test. Furthermore, the rats treated with CPE1 made a distinction between the active lever and the inactive lever. In the Morris water labyrinth, the latency for reaching the platform in the case of the rats treated with CPE1 and CPE2 decreases during the tests.

Thus, the daily preventive oral administration of CPE1, CPE2 or vitamin E for 14 days protects rats against an overproduction of free radicals after a heat stroke and preserves them from cognitive deficiencies.

1) Materials and methods

Animals

Eight male rats of Wistar/Han IGS strain (Charles River Laboratories, 69-St-Germain sur l'Arbresle—France) weighing 300 to 320 g are used. On receipt, the rats are housed, four to a cage, in 48×27×20 cm polycarbonate cages (U.A.R., 91-Epinay-Sur-Orge, France) in a controlled environment (50±5% humidity; temperature 22±1° C.; lighting from 20:00 h to 08:00 h, i.e. an inverted lightness/darkness cycle: 12 h/12 h). The rats have free access to a standard diet (M20 granules, Dietex, 95—Saint Gratien, France) and to tap water up to the time of the experiment.

After a 7-day period of acclimatization counting from the day of their arrival, the rats are weighed and divided randomly into five groups as a function of the treatment and of the exposure to a heat stroke (n=16): vehicle without heat stroke (spring water), vehicle/heat stroke (spring water), vitamin E/heat stroke (200 mg/kg of body weight/day vitamin E in olive oil; Xinchang Pharmaceuticals Factory, France); CPE1/heat stroke (22.9 mg/kg of body weight/day of CPE1 in spring water, Barry Callebaut, France), CPE2/heat stroke (24.3 mg/kg of body weight/day of CPE2 in spring water, Barry Callebaut, France). Thus, the vitamin E is dissolved in olive oil, in contrast with CPE1 and CPE2 which are dissolved in water, out of concern to increase the supply of energy.

All the rats which received CPE1, CPE2 or vitamin E are exposed to a heat stroke.

The rats are weighed each day for the fourteen days of the treatment in order to determine their body weight change.

The tests were performed in double-blind mode and the behavior recorded is evaluated by the experimenters without them knowing the products administered. The rats used in the present study are treated in accordance with the rules established by the ASAB Ethical Committee (1993) and the Canadian Council on Animal Care (1993). All the standard operating procedures used by ETAP were in accordance with the European Communities Council Directive.

Products

CPE1 and CPE2 are solvent-free products and contain, respectively, 37.45% and 35.40% of total polyphenols.

CPE1, CPE2, vitamin E or the vehicle are administered orally to the rats for 14 successive days (D1 to D14). After each daily administration of the product, the rats have free access to standard food granules.

Exposure to a Heat Stroke

On the 16th day, after fasting over night, the conscious rats of the various groups, with the exception of those of the vehicle group, are exposed to a heat stroke by placing them in a temperature-controlled chamber at 40° C. with a relative humidity of 50% for 120 minutes. The rats expressed their normal heat-regulating behavior. Immediately after the heat stroke, the rats with a rectal temperature of between 41.5° C. and 42° C. are included in the study. The rats returned to their cage at 22° C.

Free Radicals in the Blood Plasma

On the 16th day, 500 µl of blood samples were collected from the tail vein of 12 rats of each group, into tubes containing heparin to check the increase in free radicals after exposure to the heat stroke. On the basis of the chemiluminescence of pholasine, a photo-protein from the marine mollusc *Pholas dactylus*, the production of leukocyte free radicals was measured using a kit (Knight Scientific, Cell Activation Test Kits for Whole Blood with Adjuvant-K) by activation of the NADPH oxydase complex in diluted blood (In CytoTox laboratory, Nancy, France).

Cognitive Performances

Light Extinction Test (Test of Avoidance of an Aversive Light Stimulus)

Three days after exposure to the heat stroke, on day 18 (D18), the rats are tested for the preventive antioxidant effects of the two CPEs on the learning performances, by using the light extinction test. The experimental device consists of a brightly lit cage (50×40×37 cm). The level of lighting in the test cage is 1200 lux. Two levers are included in the device: an active lever that produces a 30-second period of darkness when it is pressed, and an inactive lever. During the darkness, pressing the active lever does not prolong the period of darkness.

During the test session, the rats are placed individually in the cage for 20 minutes to learn how to control the light environment. The number of presses on the active lever and on the inactive lever is recorded, as is the ability of the rats to distinguish between the two levers.

Morris Water Labyrinth Lest (Aquatic Labyrinth Test)

The Morris water labyrinth (1984) makes it possible to test the capacity for spatial orientation and the processes of learning and memorization. On the 20th and 21st days (D20 and D21), the rats are tested in the water labyrinth device to evaluate the spatial learning performances and their long-term memory. The experimental procedure consists in training rats, on the 20th day, to find a hidden platform (10 mm below the surface of the water) at a fixed point in the water tank (150 cm in diameter) in a series of five tests starting from the same starting point.

During the first test, the platform is placed against the wall of the tank. During the second test, the platform is placed 5 cm from the wall of the tank to allow the rats to find the platform easily. During the following three tests, the platform is placed 10 cm from the wall of the tank. Each test is followed by a 30-second rest period on the platform.

On the 21st day, the platform is placed at a distance from the wall of the tank in the same place as during the session on the 20th day and the long-term memory of the rats is tested in a single test.

The variable recorded in the water tank is the latency time required to get out of the water and reach the platform serving as a refuge arranged in the basin.

Statistics

Analysis of variance (ANOVA) is used to compare the five groups. When a significant result is observed, the ANOVA is followed by a Dunnett t test to compare the treated groups with the control groups. As regards the repeated measurements, a paired t test (bilateral) is used in each group. The results are expressed in the form of a mean±standard error (SEM). All the statistical analyses are performed using the StatView®5 statistical software (SAS, Inc., USA). As regards all the comparisons, the differences are considered as being significant as $P<0.05$.

2) Results

Weight Variation

As shown in table 5 below, no significant difference was observed during the 14-day treatment period in the body weights of the rats of the five groups.

TABLE 5

Body weight change (g) (Mean ± SEM)

| | Day | | | | | | |
|---|---|---|---|---|---|---|---|
| | 1 | 3 | 4 | 5 | 6 | 7 | 8 |
| Vehicle | 328.9 ± 13.6 | 336.8 ± 13.6 | 339.8 ± 12.8 | 342.8 ± 13.5 | 346.9 ± 13.8 | 349.2 ± 13.6 | 352.3 ± 13.8 |
| Vehicle/HS | 322.2 ± 13.8 | 329.3 ± 13.4 | 331.9 ± 13.0 | 334.6 ± 12.5 | 339.3 ± 12.5 | 342.4 ± 13.6 | 345.3 ± 14.2 |
| CPE 1/HS | 325.8 ± 8.8 | 333.4 ± 11.1 | 336.1 ± 10.6 | 340.0 ± 11.1 | 344.0 ± 11.6 | 346.8 ± 11.0 | 350.6 ± 11.5 |
| CPE 2/HS | 325.1 ± 12.1 | 332.5 ± 12.3 | 335.6 ± 11.6 | 340.0 ± 10.9 | 344.2 ± 9.7 | 346.9 ± 11.0 | 349.0 ± 11.1 |
| Vitamin E/HS | 320.9 ± 15.4 | 328.9 ± 15.8 | 330.6 ± 15.7 | 333.9 ± 16.5 | 336.6 ± 15.9 | 339.4 ± 17.3 | 342.1 ± 17.2 |
| ANOVA $F_{(4,75)}$ Significant nature | 0.64 NS | 0.62 NS | 0.84 NS | 0.93 NS | 1.11 NS | 0.91 NS | 0.93 NS |

| | Day | | | | | |
|---|---|---|---|---|---|---|
| | 9 | 10 | 11 | 12 | 13 | 14 |
| Vehicle | 356.3 ± 13.8 | 359.7 ± 13.3 | 363.3 ± 12.6 | 366.9 ± 12.9 | 371.0 ± 13.1 | 373.9 ± 11.8 |
| Vehicle/HS | 348.9 ± 14.0 | 352.8 ± 14.0 | 355.5 ± 13.9 | 359.0 ± 14.8 | 363.2 ± 15.4 | 368.1 ± 15.2 |
| CPE 1/HS | 354.1 ± 12.6 | 358.2 ± 12.6 | 361.4 ± 11.9 | 363.6 ± 12.6 | 368.4 ± 12.7 | 371.8 ± 12.6 |
| CPE 2/HS | 352.8 ± 11.1 | 355.5 ± 10.0 | 358.6 ± 9.9 | 361.9 ± 11.0 | 366.3 ± 10.9 | 368.8 ± 11.2 |
| Vitamin E/HS | 344.3 ± 15.6 | 348.7 ± 17.8 | 351.6 ± 18.0 | 354.6 ± 18.8 | 357.6 ± 19.4 | 361.0 ± 18.4 |
| ANOVA $F_{(4,75)}$ Significant nature | 1.26 NS | 1.06 NS | 1.22 NS | 1.10 NS | 1.34 NS | 1.27 NS |

Consequently, the products did not induce any toxicological effects after 14 days of subchronic administration.

Heat Stroke and Free Radical Contents in the Plasma

On the 16th day, the analysis of variance shows large heterogeneity in the free radical contents in the five groups.

As shown in table 6 below, the "vehicle/heat stroke" rats have a large amount of circulating free radicals compared with that of the other groups.

TABLE 6

Free radical content in the plasma on the 16th day (mV)
(Mean ± SEM)

| Groups (*) | Vehicle/HS (n = 13) | Vehicle (n = 14) | CPE 1/HS (n = 14) | CPE 2/HS (n = 14) | Vitamin E/HS (n = 13) |
|---|---|---|---|---|---|
| Free radical content | 1257.46 ± 163.79 | 310.07 ± 19.55 | 300.79 ± 11.31 | 281.68 ± 44.84 | 311.15 ± 20.56 |
| | ANOVA: $F_{(4,63)} = 421.66$; $p < 0.001$ | | | | |
| Dunnett t test (vs. Vehicle/HS) | — | t = 21.51 | t = 21.83 | t = 21.47 | t = 20.67 |
| Significant nature | | $p < 0.001$ | $p < 0.001$ | $p < 0.001$ | $p < 0.001$ |

(*) Certain samples were hemolyzed and could not be analyzed.

After the heat stroke, the circulating free radicals in the vehicle/heat stroke rats increases significantly in comparison with those of the vehicle rats, which indicates the capacity of the heat stroke to induce a large oxidative stress.

The free radical contents in the CPE1/heat stroke, CPE2/heat stroke and vitamin E/heat stroke rats are markedly lower than those of the vehicle/heat stroke rats, which shows a protection of the body against the production of free radicals after a subchronic administration of CPE1, CPE2 or vitamin E. The difference in free radical contents between the vehicle/heat stroke group and the vitamin E/heat stroke group or between the CPE1/heat stroke or CPE2/heat stroke groups must be due to the antioxidant effects of vitamin E, CPE1 or CPE2 themselves.

Cognitive Performances

Light Extinction Test

Total Number of Lever Presses:

As shown in table 7 below, no significant difference was observed in the total number of lever presses for the rats of the five groups.

TABLE 7

Total number of lever presses
(Mean ± SEM)

| Groups (*) (n = 16/group) | Vehicle | Vehicle/HS | CPE 1/HS | CPE 2/HS | Vitamin E/HS |
|---|---|---|---|---|---|
| Total lever presses | 32.88 ± 6.34 | 42.75 ± 5.84 | 26.81 ± 4.52 | 24.69 ± 4.71 | 42.38 ± 5.76 |
| | ANOVA: $F_{(4,75)} = 2.39$; NS | | | | |
| Unpaired t test (vs. vehicle) | | t = 1.15 | t = 0.78 | t = 1.04 | t = 1.11 |
| Significant nature | | NS | NS | NS | NS |
| Unpaired t test (vs. vehicle/HS) | | | t = 2.16 | t = 2.41 | t = 0.05 |
| Significant nature | | | $p < 0.05$ | $p < 0.05$ | NS |

Discrimination of the Levers:

As shown in table 8, the rats of the vehicle, vitamin E/heat stroke and CPE1/heat stroke groups pressed the active lever more than the inactive lever. The rats of the CPE2/heat stroke group only attempted to make a distinction between the active lever and the inactive lever. The vehicle/heat stroke rats made no distinction between the two levers.

TABLE 8

Distinction between levers
Number of active lever presses (ALP) vs. number of inactive lever presses (ILP) (mean ± SEM)

| Groups (n = 16/group) | Vehicle | Vehicle/HS | Vitamin E/HS # | CPE 1/HS | CPE 2/HS |
|---|---|---|---|---|---|
| ALP | 20.38 ± 3.96 | 23.19 ± 3.35 | 27.28 ± 3.54 | 15.63 ± 2.82 | 14.19 ± 2.76 |
| ILP | 12.50 ± 3.13 | 19.56 ± 2.93 | 17.60 ± 2.47 | 11.19 ± 1.87 | 10.50 ± 2.41 |
| Paired t test (ALP vs. ILP) | t = 2.40 $p < 0.05$ | t = 1.55 NS | t = 3.81 $p < 0.005$ | t = 2.85 $p < 0.05$ | t = 1.71 $p = 0.10$ | one rat was removed from the statistical analysis because it did not press the inactive lever during the test (vitamin E/HS: n = 15)

During the light extinction test, the total number of lever presses for the rats of the five groups does not show any significant difference. The rats of the vehicle, vitamin E/heat stroke and CPE1/heat stroke groups pressed the active lever more than the inactive lever. The rats treated with CPE2/heat stroke only had a tendency to press the active lever more than the inactive lever, whereas those treated with vehicle/heat stroke made no distinction between the active lever and the inactive lever.

Morris Water Labyrinth Test

In test 1, the analysis of variance shows a significant difference in the latency time for reaching the platform in the five treatment groups. The Dunnett t test shows that the latency for reaching the platform in the vehicle/heat stroke rats is markedly lower than that for the other rats.

In the other tests, the analysis of variance does not show any significant heterogeneity in latency in the time for reaching the platform in the five groups.

Test 3 is the reference test since the platform was distanced from the wall of the water labyrinth such that the rats do not reach it by chance.

The paired t test shows that the rats of the vehicle group significantly improved their latency for reaching the platform between test 3 and tests 4, 5 and 6. The rats of the vehicle/heat stroke group did not improve their latency between test 3 and tests 4, 5 and 6. The rats of the vitamin E/heat stroke group did not improve their latency between test 3 and test 4 and significantly improved it between test 3 and test 5 and had a tendency toward improving it between test 3 and test 6. The rats of the CPE1/heat stroke group did not improve their latency between test 3 and test 4, and improved it significantly between test 3 and tests 5 and 6. The rats of the CPE2/heat stroke group had a tendency toward improving their latency between test 3 and test 4, toward significantly improving it between test 3 and test 5 and had a tendency toward improving it between test 3 and test 6.

The rats of the vehicle/heat stroke group show no significant improvement throughout the test.

TABLE 9

Morris water labyrinth test: latency for reaching the platform (s)
(Mean ± SEM)

| Groups (n = 16/group) | Day 20 | | | | | Day 21 |
|---|---|---|---|---|---|---|
| | Test 1 | Test 2 | Test 3 | Test 4 | Test 5 | Test 6 |
| Vehicle | 48.81 ± 7.43 | 29.56 ± 5.41 | 27.38 ± 4.45 | 18.50 ± 2.94 | 14.38 ± 3.04 | 12.12 ± 2.25 |
| Vehicle/HS | 29.69 ± 2.73 | 35.56 ± 7.55 | 21.00 ± 4.62 | 13.94 ± 1.32 | 14.19 ± 2.05 | 12.50 ± 1.71 |
| CPE 1/HS | 43.81 ± 5.52 | 38.88 ± 7.29 | 22.81 ± 4.45 | 17.50 ± 3.78 | 11.94 ± 1.70 | 10.19 ± 1.28 |
| CPE 2/HS | 54.88 ± 6.37 | 25.25 ± 4.89 | 17.63 ± 2.73 | 12.25 ± 1.49 | 8.63 ± 1.07 | 12.69 ± 2.66 |
| Vitamin E/HS | 51.75 ± 6.45 | 25.38 ± 4.94 | 26.44 ± 5.20 | 17.75 ± 2.44 | 13.56 ± 1.37 | 14.69 ± 2.22 |
| ANOVA | $F_{(4,75)} = 2.78$ | $F_{(4,75)} = 1.00$ | $F_{(4,75)} = 0.84$ | $F_{(4,75)} = 1.14$ | $F_{(4,75)} = 1.47$ | $F_{(4,75)} = 0.60$ |
| Significant nature | $p < 0.05$ | NS | NS | NS | NS | NS |

TABLE 10

Morris water labyrinth test: comparison between the tests

| Groups (n = 16/group) | Test 3 vs. test 4 | Test 3 vs. test 5 | Test 3 vs. test 6 |
| --- | --- | --- | --- |
| Vehicle | t = 2.26<br>p < 0.05 | t = 2.54<br>p < 0.05 | t = 3.27<br>p < 0.01 |
| Vehicle/HS | t = 1.52<br>NS | t = 1.38<br>NS | t = 1.75<br>NS |
| CPE 1/HS | t = 1.15<br>NS | t = 2.46<br>p < 0.05 | t = 2.72<br>p < 0.05 |
| CPE 2/HS | t = 1.95<br>p < 0.08 | t = 3.86<br>p < 0.005 | t = 2.08<br>p < 0.06 |
| Vitamin E/HS | t = 1.57<br>NS | t = 2.34<br>p < 0.05 | t = 2.11<br>p < 0.06 |

3) Discussion and Conclusion

Several studies have shown the antioxidant activity of flavonoids in humans by rapid absorption of epicatechins into the serum after consumption of chocolate or drinking of green tea. In the presence of cocoa polyphenols, the oxidation of low-density lipoproteins decreases. It has also been related that catechin and epicatechin were absorbed competitively into the gastrointestinal tract of rats. A large variation in the total phenol content in each type of chocolate and of cocoa was also described.

It is for this reason that it appeared important to study the antioxidant activity of each specific extract as a function of the production process and of the origin of the cocoa.

The preventive antioxidant effects of the two CPEs, administered orally for 14 days, were evaluated on the basis of the overproduction of free radicals and of the cognitive deficiencies after exposure to a heat stroke in male Wistar rats. The free radical contents in the plasma and the antioxidant effects of the two products were determined in vitro after the heat stroke on the 16th day. The light extinction test was performed on the 18th day and the Morris water labyrinth test was performed on the 20th day and the 21st day. These cognitive tests were used to evaluate the preventive effects of the cocoa extracts on the cognitive deficiencies induced by an overproduction of free radicals following exposure to a heat stroke.

Conclusion:

These results suggest that vitamin E (200 mg/kg body weight/day), CPE1 (22.9 mg/kg body weight/day) and CPE2 (24.3 mg/kg body weight/day), administered orally for 14 successive days, protect the rats against cognitive deficiencies induced by the heat stroke (i.e. learning discrimination in the extinction test and spatial learning in the Morris water labyrinth test).

In order to exploit these two rich polyphenol sources, it is necessary to enrich the cocoa powder or other chocolate-based products with CPEs. The antioxidant properties of the CPEs will be evaluated after their incorporation into food products.

EXAMPLE 10

Evaluation of the Preventive Effects of a Cocoa Polyphenol Extract Administered Orally at 2 Doses on the Development of Chemo-induced Prostate Tumors in Adult Male Rats of Wistar-Unilever Strain A) Study Report No. 1

The aim of study No. 1 below is to evaluate the preventive effects of a CPE administered daily orally at a dose of 24 mg/kg of body weight or 48 mg/kg of body weight on the development of chemo-induced prostate tumors and to evaluate the effects of the CPE on the cognitive performances in male rats of Wistar-Unilever strain.

1. Protocol

Animals 75 male rats of Wistar-Unilever strain weighing 250 to 275 g are used.

Rearing Conditions

Temperature: 22±1° C., hygrometry: 50±10%, inverted lightness/darkness cycle: 12 h/12 h.

Treatment Groups 5 groups of 15 rats are used:
"control" group: no chemo-induction or treatment;
"vehicle" group: no chemo-induction and treatment with the vehicle serving as placebo;
"chemo-induction control" group: treatment with the placebo;
"chemo-induction+CPE 24" group: treatment with CPE at 24 mg/kg;
"chemo-induction+CPE 48" group: treatment with CPE at 48 mg/kg;

Randomization of the Animals

As a function of the body weight on day D0.

Induction of the Prostate Tumors

The induction takes place in 2 steps:
initiation step=single intravenous injection of MNU at a dose of 35 mg/kg;
activation step=one week later, subcutaneous implantation of a silastic tube 2 cm long blocked at one end with a biological adhesive and containing 40 mg of testosterone propionate (TP).

The activation test was repeated 3 times at 2-monthly intervals.

Substances Studied

Cocoa polyphenol extract (CPE) at two doses: 24 mg/kg of body weight and 48 mg/kg of body weight.

Administration Route

Oral gavage.

Duration of the Treatment

For 38 weeks, from Monday to Friday, with a pause on Saturday and Sunday.

Start of the Treatment 2 weeks after the induction of prostate tumors.

Evaluation Criteria

Body weight, consumption of food and water, histopathological examinations of the prostate.

Cognitive Tests

Test of avoidance of an aversive light stimulus (TAALS) performed 2, 4, 6 and 8 months after the induction of prostate tumors, and Morris aquatic labyrinth test performed 5 and 8 months after the induction of prostate tumors.

Sacrifice of the Animals

Six of the animals of each group are sacrificed 9 months after the induction of prostate tumors to perform histopathological examinations.

Statistical Analyses

Analysis of variance followed by an unpaired t test (bilateral) for the body weight comparisons of the animals; Kruskal-Wallis test followed by a Mann-Whitney U test for comparisons of the consumption of food and water and of the cognitive test performances.

2. Results

Figure 43:
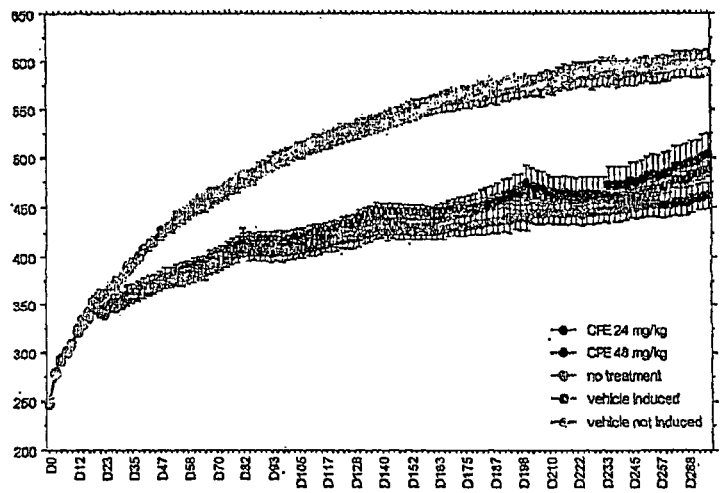

During the 9 months of the experiment, the body weight gain was significantly higher in the animals of the "control" and "vehicle" groups than in those subjected to a chemo-induction treated orally with the vehicle or CPE at 24 or 48 mg/kg (see FIG. 43).

As regards the body weight gain, no significant difference was observed between the "control" and "vehicle" groups. Similarly, no significant difference was observed between the animals of the groups subjected to a chemo-induction treated orally with the vehicle or with CPE at 24 or 48 mg/kg (FIG. 43).

Figure 44:
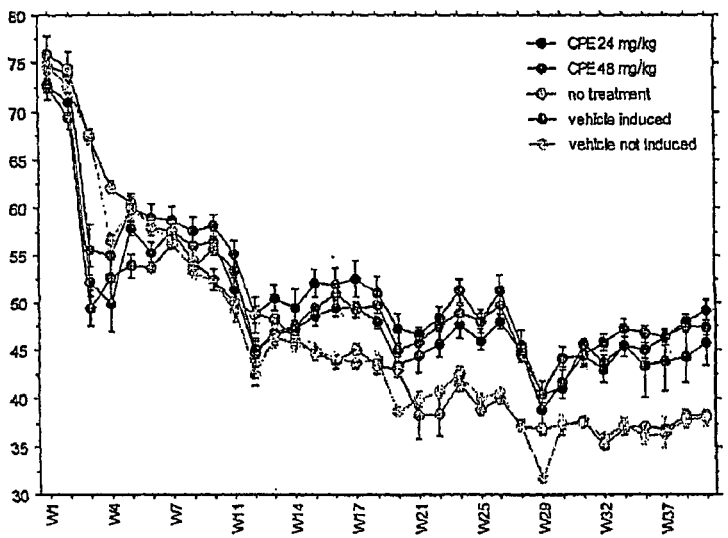

Between week 1 and week 14, no significant difference was detected between the 5 groups as regards the consumption of food (FIG. 44).

Between week 15 and week 39, the consumption of food was significantly higher in the animals of the groups subjected to a chemo-induction treated orally with the placebo or with CPE at 24 or 48 mg/kg than in those of the "control" and "vehicle" groups.

Figure 45:
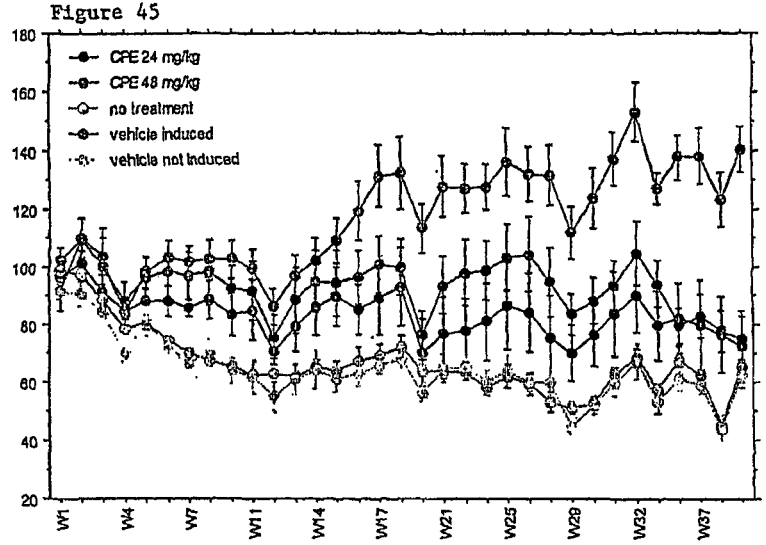

Between week 1 and week 5, no significant difference was detected between the 5 groups as regards the consumption of water (FIG. 45).

Between week 5 and week 39, the consumption of water was significantly higher in the animals of the groups subjected to a chemo-induction treated orally with the placebo or with CPE at 24 or 48 mg/kg than in those of the "control" and "vehicle" groups.

Between week 16 and week 39, the water consumption of the groups subjected to a chemo-induction and an oral treatment was significantly higher in the animals exposed to the placebo than in those which received CPE at 24 or 48 mg/kg.

Figure 46:
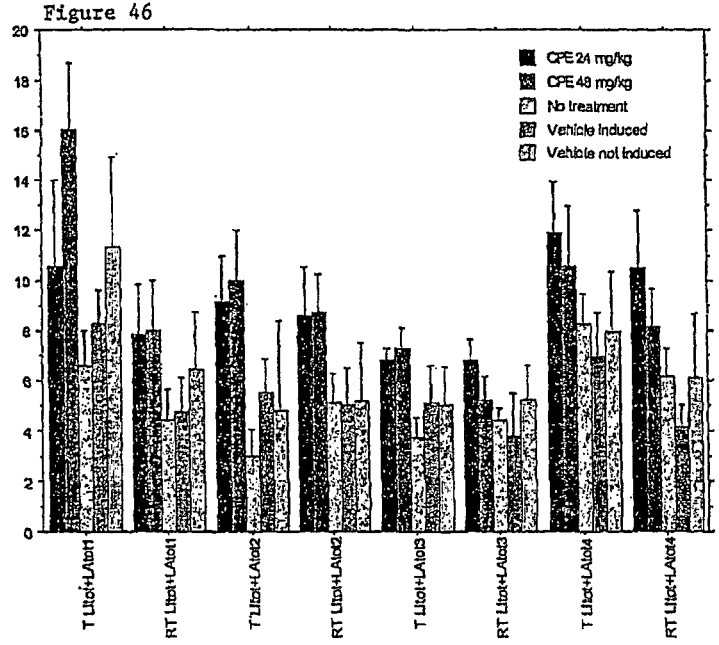

In the TAALS test and as a whole (i.e. during the 4 test sessions and test repetitions), the mean total number of lever presses was invariably higher in the animals of the groups subjected to a chemo-induction treated orally with CPE at 24 or 48 mg/kg (FIG. 46). The lowest mean total number of lever presses was recorded for the animals subjected to a chemo-induction treated orally with the placebo.

Figure 49:
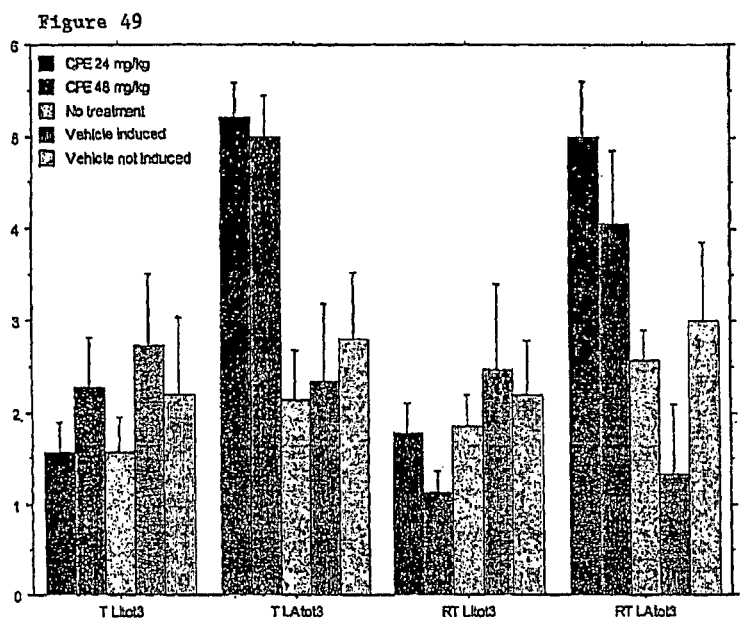

In the first, second and third TAALS tests and in the test repetitions repeated 2 months (FIG. 47), 4 months (FIG. 48) and 6 months (FIG. 49) after the induction of prostate tumors, the highest number of presses on the active lever were measured for the animals of the groups subjected to a chemo-induction treated orally with CPE at 24 or 48 mg/kg and those of the "control" and "vehicle" groups. In all cases, the number of presses on the active lever were significantly higher in the groups subjected to a chemo-induction treated orally with CPE at 24 or 48 mg/kg than in the other groups, and a discrimination between the active lever and the inactive lever was reported in these animals.

Figure 50:
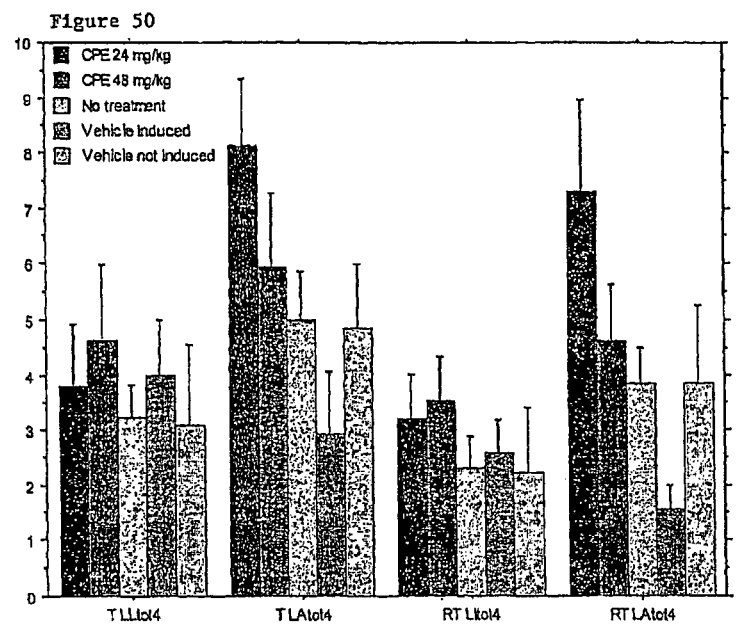

In the fourth TAALS test and in the test repetitions performed 8 months after the induction of prostate tumors, the animals (FIG. 50) of the groups subjected to a chemo-induction treated orally with CPE at 24 or 48 mg/kg and those of the "control" and "vehicle" groups pressed the active lever more often than the inactive lever. The number of presses on the active lever was significantly higher in the group subjected to a chemo-induction treated orally with CPE at 24 mg/kg than in the other groups. The highest number of presses on the inactive lever was recorded in the group of animals subjected to a chemo-induction treated with the placebo.

Figure 51:
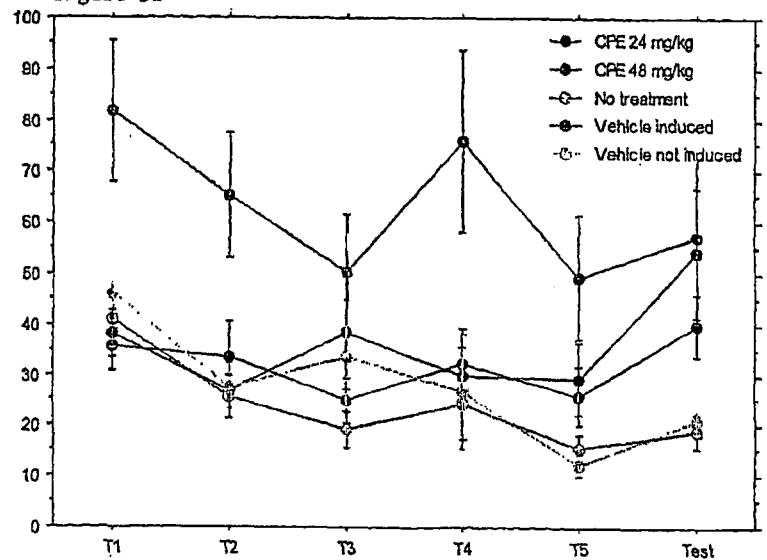

In the first Morris aquatic labyrinth test performed 5 months after the induction of prostate tumors, the curves were similar in the groups subjected to a chemo-induction treated orally with CPE at 24 or 48 mg/kg and in the "control" and "vehicle" groups during the 5 learning session tests. The mean latency time was significantly higher in the animals subjected to a chemo-induction treated with the placebo than in those of the other groups. In the test session, the mean latency times were significantly longer in the animals of the groups subjected to a chemo-induction treated with the placebo or CPE at 24 or 48 mg/kg than in those of the "control" or "vehicle" groups (FIG. 51).

Figure 52:
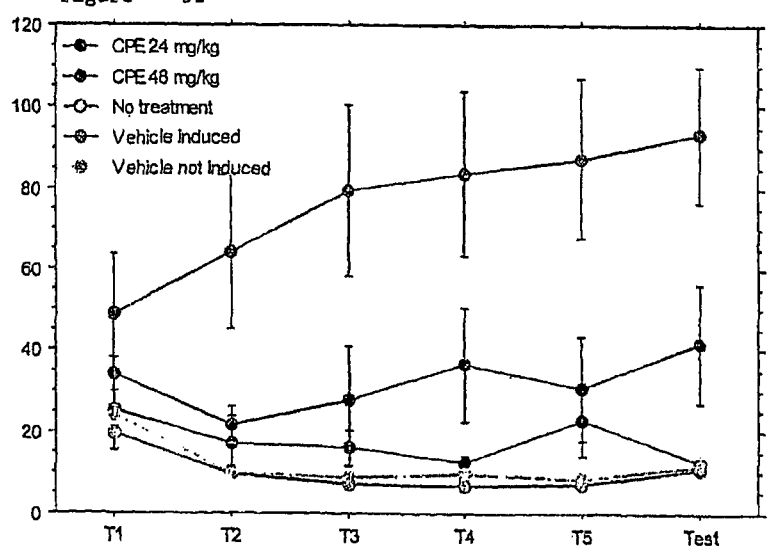

In the second Morris aquatic labyrinth test performed 8 months after the induction of prostate tumors, the curves were similar in the groups subjected to a chemo-induction treated orally with CPE at 24 mg/kg and in the "control" and "vehicle" groups during the 5 learning session tests and the test session. The mean latency times were significantly longer in the animals subjected to a chemo-induction treated with the placebo or CPE at 48 mg/kg than in those of the other groups, and the mean latency time was significantly longer in the animals of the group subjected to a chemo-induction treated with the placebo than in those of the group subjected to a chemo-induction receiving CPE at 48 mg/kg (FIG. 52).

The observations that follow relate to the histopathological examinations of the prostate performed on 6 of the animals of each group sacrificed 9 months after the induction of prostate tumors. The following were observed:

1 focal hyperplasia in the 5 groups of rats;

1 diffuse hyperplasia in the "control" and "vehicle" groups, 2 in the group subjected to a chemo-induction treated orally with CPE at 24 mg/kg and 3 in the groups subjected to a chemo-induction treated orally with the placebo or CPE at 48 mg/kg;

1 prostate adenoma in the group subjected to a chemo-induction treated orally with CPE at 48 mg/kg and 2 in the group subjected to a chemo-induction treated orally with the placebo;

1 prostate lymphoma in the group subjected to a chemo-induction treated orally with CPE at 48 mg/kg and 2 in the group subjected to a chemo-induction treated orally with the placebo.

No prostate adenomas or lymphomas were detected in the group subjected to a chemo-induction treated with CPE at 24 mg/kg or in the "control" and "vehicle" groups.

3. Conclusion

No significant difference was detected as regards the body weight gains between the groups subjected to a chemo-induction treated orally with the placebo or CPE at 24 or 48 mg/kg. The body weight gains were significantly higher in the "control" and "vehicle" groups than in those subjected to a chemo-induction treated orally with the placebo or CPE at 24 or 48 mg/kg.

The food consumption was significantly higher between week 15 and week 39 in the groups subjected to a chemo-induction treated orally with the placebo or CPE at 24 or 48 mg/kg than in the "control" and "vehicle" groups.

The water consumption was significantly higher between week 5 and week 39 in the groups subjected to a chemo-induction treated orally with the placebo or CPE at 24 or 48 mg/kg than in the "control" and "vehicle" groups. Between week 15 and week 39, the water consumption was significantly higher in the group subjected to a chemo-induction treated orally with the placebo than in the other groups subjected to a chemo-induction treated orally with CPE at 24 or 48 mg/kg.

In the test of avoidance of an aversive light stimulus (TAALS), the learning and memorization performances of the rats of the groups subjected to a chemo-induction treated orally with CPE at 24 or 48 mg/kg were significantly better than those of the animals of the other groups.

In the Morris aquatic labyrinth test, the learning and memorization performances of the rats of the groups subjected to a chemo-induction treated orally with CPE at 24 or 48 mg/kg were significantly better than those of the animals of the group subjected to a chemo-induction treated orally with the placebo. The memorization performances of the rats of the group subjected to a chemo-induction treated orally with CPE at 24 mg/kg were comparable with those of the animals of the "control" and "vehicle" groups.

The most important lesions detected 9 months after the induction of prostate tumors, i.e. a prostate adenoma or lymphoma, were reported only in the groups subjected to a chemo-induction treated orally with the placebo or with CPE at 48 mg/kg. Lesions of this type were not observed in the group subjected to a chemo-induction treated with CPE at 24 mg/kg or in the "control" and "vehicle" groups.

When administered at a dose of 24 mg/kg, CPE imparts protection against chemo-induced prostate tumors in rats.

Study Report No. 2: Continuation of Study Report No. 1 Over 6 Months

The aim of study No. 2 below is to prolong study No. 1 described above and to evaluate the preventive effects of a CPE administered daily at a dose of 24 mg/kg of body weight or of 48 mg/kg of body weight on the development of chemo-induced prostate tumors and to evaluate the effects of CPE on the cognitive performances in male rats of Wistar-Unilever strain.

1. Protocol

Animals 45 male rats of Wistar-Unilever strain weighing from 250 to 275 g at the start of the experiment are used.

Rearing Conditions

Temperature: 22±2° C., hygrometry: 50±10%, Inverted Lighting/Darkness Cycle: 12 h/12 h.

Treatment Groups 5 groups of 9 rats are used:
"control" group: no chemo-induction or treatment;
"vehicle" group: no chemo-induction and treatment with the vehicle serving as placebo;
"chemo-induction control" group: treatment with the placebo;
"chemo-induction+CPE 24" group: treatment with CPE at 24 mg/kg;
"chemo-induction+CPE 48" group: treatment with CPE at 48 mg/kg.

Induction of the Prostate Tumors

The induction is performed in 2 steps over 9 months before performing the present study:
initiation step=single intravenous injection of MNU at a dose of 35 mg/kg;
activation step=one week later, subcutaneous implantation of a silastic tube 2 cm long blocked at one end with a biological adhesive and containing 40 mg of testosterone propionate (TP).

The activation step was repeated 3 times at 2-monthly intervals.

Substances Studied

Cocoa polyphenol extract (CPE) at two doses: 24 mg/kg of body weight and 48 mg/kg of body weight.

Administration Route

Oral gavage.

Duration of the Treatment

For 26 weeks, from Monday to Friday, with a pause on Saturday and Sunday.

Start of the Treatment 2 weeks after the induction of prostate tumors.

Evaluation Criteria

Body weight, consumption of food and water, levels of dopamine, catecholamines and creatinines in the urine, histopathological examinations of the prostate.

Cognitive Tests

Test of avoidance of an aversive light stimulus (TAALS) and Morris aquatic labyrinth test performed 11 and 13 months after the induction of prostate tumors.

Statistical Analyses

Analysis of variance followed by an unpaired t test (bilateral) for the body weight comparisons of the rats; Kruskal-Wallis test followed by a Mann-Whitney U test for comparisons of the consumption of food and water and of the cognitive test performances.

2. Results

Figure 53:
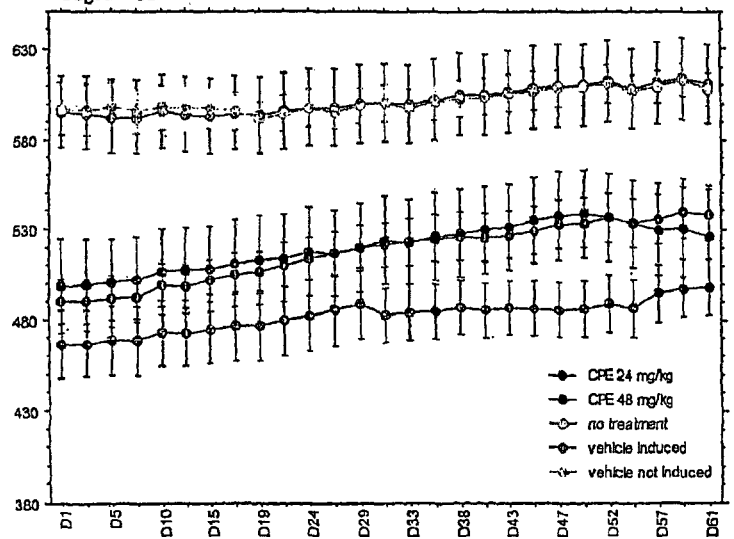

In the first 4 months of the experiment, the body weight gain of the "control" and "vehicle" groups was significantly higher than that of the three groups subjected to a chemo-induction treated orally with the vehicle or CPE at 24 or 48 mg/kg (see FIG. 53).

As regards the body weight gain, no significant difference was observed between the "control" and "vehicle" groups. Similarly, no significant difference was observed between the animals of the groups subjected to a chemo-induction treated orally with the vehicle or with CPE at 24 or 48 mg/kg (FIG. 53).

Figure 54:
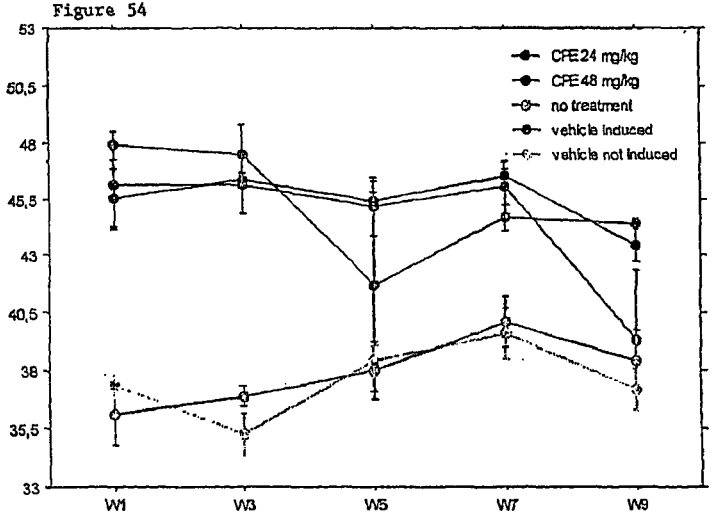
Figure 57:
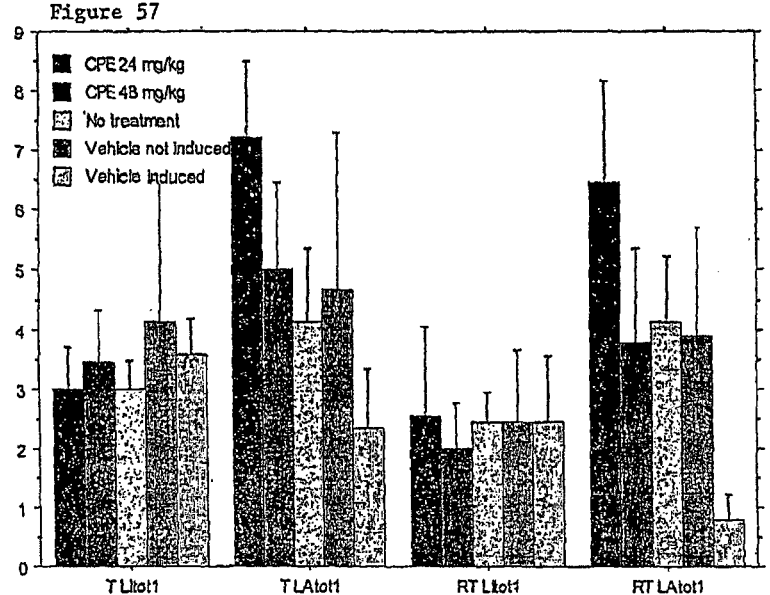
Figure 58:
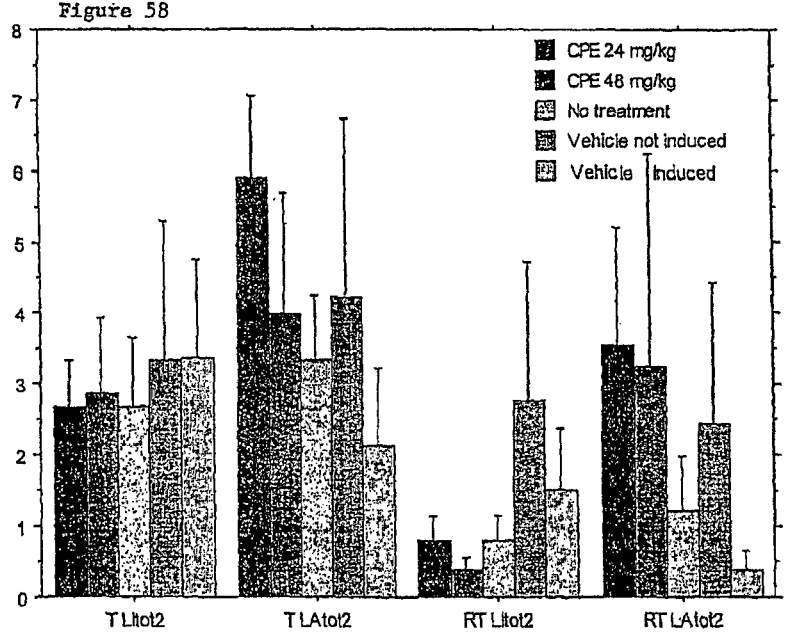

The food consumption of the chemo-induced groups, treated orally with the vehicle or with CPE at 24 or 48 mg/kg, is significantly higher than that of the "control" and "vehicle" groups (FIG. 54).

The water consumption of the animals of the groups subjected to a chemo-induction treated orally with CPE at 24 or 48 mg/kg is not different from that of the "control" and "vehicle" groups. The water consumption in the animals of the groups subjected to a chemo-induction treated orally with the vehicle is significantly higher than that of the animals of the groups subjected to a chemo-induction treated orally with CPE at 24 or 48 mg/kg and the "control" and "vehicle" groups (FIG. 55).

In the TAALS test and test repetitions, performed 11 months after the induction of prostate tumors, the animals of the groups subjected to a chemo-induction treated orally with CPE at 24 or 48 mg/kg and the "control" and "vehicle" groups show the lowest level of activity in terms of lever presses and a higher number of presses on the active lever than on the inactive lever. The total numbers of presses by the rats on the levers were higher in the groups subjected to a chemo-induction treated orally with CPE at 24 mg/kg and were lower in the groups subjected to a chemo-induction treated orally with a vehicle. The groups subjected to a chemo-induction treated orally with CPE at 24 mg/kg show a higher number of presses on the active levers than on the inactive levers and the groups of animals subjected to a chemo-induction treated orally with the vehicle show a higher number of presses on the inactive levers.

In the TAALS test and test repetitions, performed 13 months after the induction of prostate tumors, the animals of the groups subjected to a chemo-induction treated orally with CPE at 24 or 48 mg/kg and the "control" and "vehicle" groups show the highest level of activity in terms of lever presses and a higher number of presses on the active lever than on the inactive lever. In all cases, the animals of the groups subjected to a chemo-induction treated orally with CPE at 24 mg/kg or 48 mg/kg show a significantly higher number of presses on the active levers than the animals of the other groups and they differentiate between the active lever and the inactive lever. The groups subjected to a chemo-induction treated orally with the vehicle show a higher number of presses on the inactive levers.

For the Morris aquatic labyrinth test performed 11 months after the induction of prostate tumors, the curves were similar in the groups subjected to a chemo-induction treated orally with CPE at 24 mg/kg and in the "control" and "vehicle" groups during the 5 tests of the learning session and of the test session (FIG. 59). The mean latency time was higher in the animals subjected to a chemo-induction treated orally with CPE at 48 mg/kg than in the other groups. The mean latency times were significantly longer in the animals of the groups subjected to a chemo-induction treated orally with the vehicle than those of the groups subjected to a chemo-induction treated orally with CPE at 48 mg/kg (FIG. 59).

In the second Morris aquatic labyrinth test performed 13 months after the induction of prostate tumors, the curves were similar in the groups subjected to a chemo-induction treated orally with CPE at 24 mg/kg and in the "control" and the "vehicle" groups during the 5 tests of the learning session and of the test session. The mean latency times were significantly longer in the animals subjected to a chemo-induction treated orally with the vehicle or CPE at 48 mg/kg than those in the other groups. No difference was observed between the mean latency times in the animals of the group subjected to a chemo-induction treated orally with the vehicle or with CPE at 48 mg/kg (FIG. 60).

Figure 61:
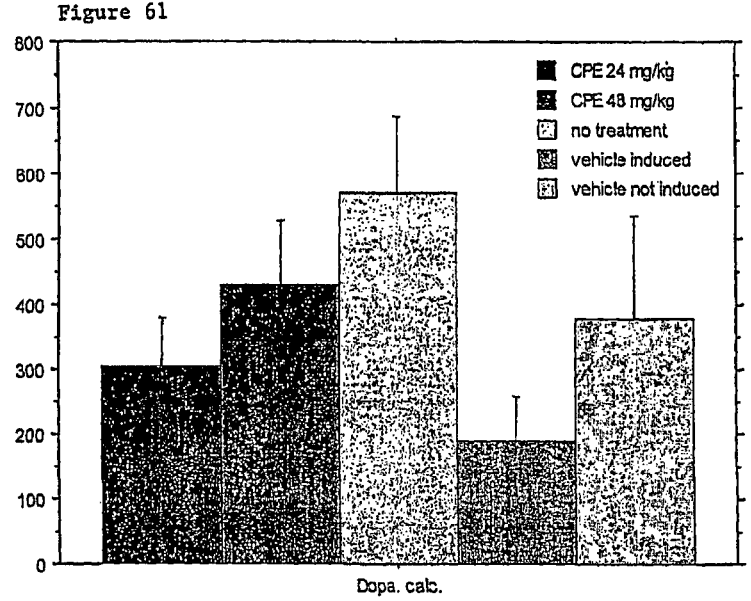
Figure 62:
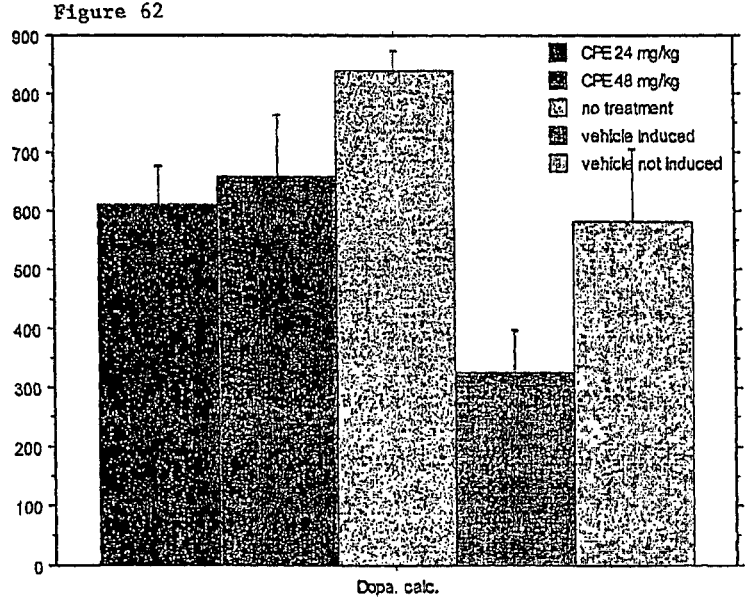

For the two measurements of the level of dopamine, catecholamines and creatinine in the urine, performed 9 and 12 months after induction of prostate tumors, the groups of chemo-induced animals treated orally with CPE at 24 or 48 mg/kg showed dopamine levels similar to those of the "control" and "vehicle" groups. The chemo-induced groups treated orally with the vehicle showed significantly lower dopamine levels (FIGS. 61 and 62).

3. Conclusion

No significant difference was detected, during the first four months of the experiment, as regards the body weight gains between the groups subjected to a chemo-induction treated orally with the vehicle or CPE at 24 or 48 mg/kg. However, the body weight gains were significantly higher in the "control" and "vehicle" groups than in those subjected to a chemo-induction treated orally with the vehicle or CPE at 24 or 48 mg/kg.

During the first 4 months of the experiment, the food consumption was significantly higher in the groups subjected to a chemo-induction treated orally with the vehicle or CPE at 24 or 48 mg/kg than in the "control" and "vehicle" groups.

During the first 4 months of the experiment, no significant difference was noted as regards the water consumption in the rats between the groups subjected to a chemo-induction treated orally with CPE at 24 or 48 mg/kg and the "control" and "vehicle" groups. The water consumption was significantly higher in the group subjected to a chemo-induction treated orally with the vehicle than in the other groups subjected to a chemo-induction treated orally with CPE at 24 or 48 mg/kg and the "control" and "vehicle" groups during the same period.

In the two tests of avoidance of an aversive light stimulus (TAALS), the learning and memorization performances of the rats of the groups subjected to a chemo-induction treated orally with CPE at 24 or 48 mg/kg were significantly better than those of the animals of the other groups.

In the two Morris aquatic labyrinth tests, the learning and memorization performances of the rats of the groups subjected to a chemo-induction treated orally with CPE at 24 mg/kg were significantly better than those of the animals of the groups subjected to a chemo-induction treated orally with the vehicle or CPE at 48 mg/kg.

The levels of dopamine, catecholamines and creatinine in the urine of the rats of the chemo-induced groups treated orally with CPE at 24 or 48 mg/kg are comparable with those observed in the "control" and "vehicle" groups.

EXAMPLE 11

Effects of a Cocoa Polyphenol Extract (CPE) as a Preventive Treatment on the Development of Chemo-Induced Prostate Tumors, on the Cognitive Performances and on Dopamine, in Rats 1. Materials and Methods
Animals:
  45 male Wistar-Unilever rats, 250-275 g,
  Controlled conditions of temperature (22±2° C.), humidity (50±10%), inverted 12-hour lighting cycle (lighting from 09:00 h to 21:00 h), food and drink ad libitum.
Treatments:
  Cocoa polyphenol extract (CPE) administered daily orally at doses of 24 or 48 mg/kg for 10 months* or 23 months**, from Monday to Friday.

| Group | Treatment | Dose |
|---|---|---|
| Not induced and not treated | — | — |
| Not induced + CPE 24* | CPE* | 24 mg/kg, oral* |
| Chemo-induced + vehicle | Vehicle | — |
| Chemo-induced + CPE 24** | CPE** | 24 mg/kg, oral** |
| Chemo-induced + CPE 43** | CPE** | 48 mg/kg, oral** |

Monitoring of the Parameters:
  Daily checking of the survival of the animals,
  Weighing of the animals 3 times a week,
  Monitoring every 2 weeks of the intake of food and drink,
  Urine sampling for dopamine assay performed 21 months after the induction of prostate tumors.
Cognitive Tests:
  TAALS: performed 21 months after the induction of prostate tumors,
  Morris pool: performed 21 months after the induction of prostate tumors.
Sacrifice of the Animals:
  Sacrifice of all the surviving animals once there are less than 5 for all the treatment groups.

2. Results

The survival of the animals is very different depending on the groups. 23 months after the induction of prostate tumors, the following are observed:
  "not induced and not treated" group: 6 out of 9 rats surviving,
  "not induced+CPE 24" group: 7 out of 9 rats surviving,
  "chemo-induced+vehicle" group: 1 out of 9 rats,
  "chemo-induced+CPE 24" group: 4 out of 9 rats surviving,
  "chemo-induced+CPE 48" group: 1 out of 9 rats surviving.
As regards the weight gain, no difference is noted between the various groups, and similarly for the intake of food and drink.

3. Conclusions
Survival of the Animals:
  The level of survival of the animals of the "chemo-induced+CPE 24" group is higher than that of the animals of the other 2 groups of chemo-induced rats but is lower than that of the 2 groups of rats not induced,
  the level of survival of the animals of the "not induced+CPE 24" group is slightly higher than that of the animals of the "not induced and not treated" group.

CPE administered at a dose of 24 mg/kg before or not before induction of prostate tumors makes it possible to increase the survival time of the rats.

Figure 63:
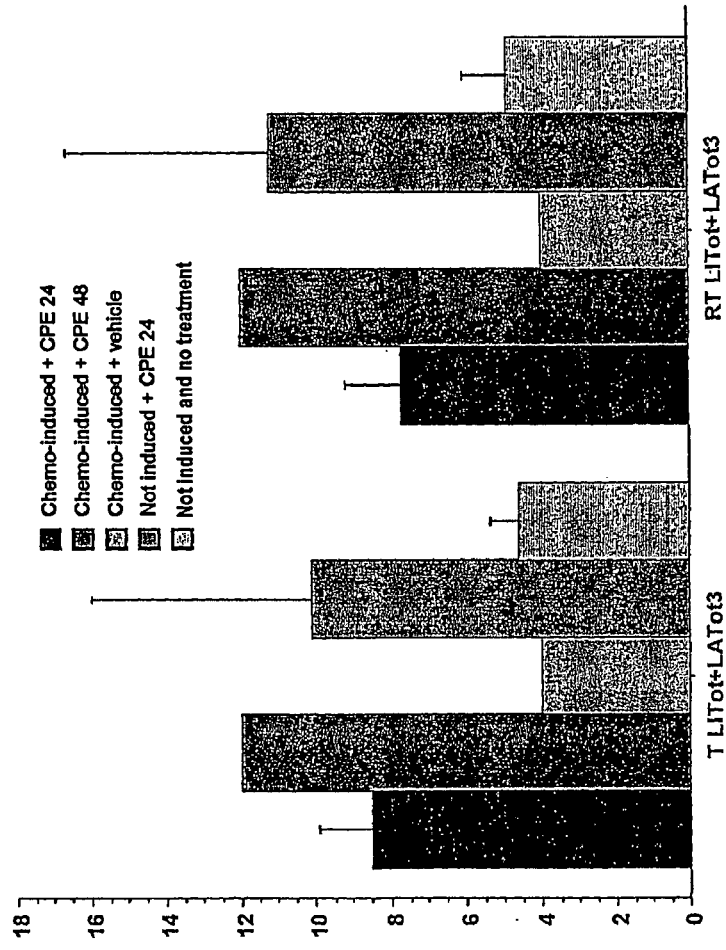
Figure 64:
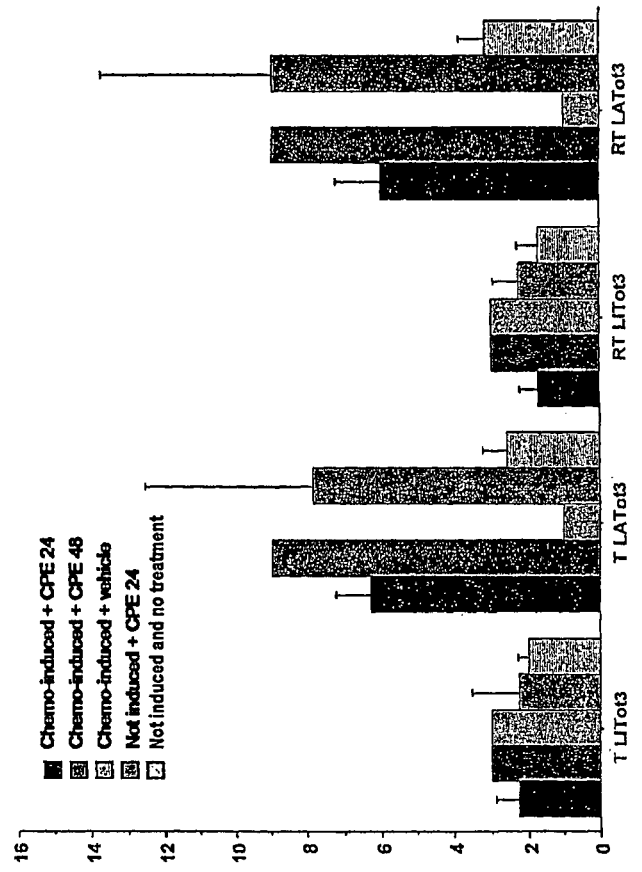

TAALS (see FIGS. 63 and 64)
- The rats of the chemo-induced or not induced groups treated with CPE at 24 or 48 mg/kg show higher activity on the levers than the rats of the 2 "chemo-induced+vehicle" and "not induced and not treated" groups and a positive discrimination between the active lever and the inactive lever for the two test and retest sessions,
- the rats of the "chemo-induced+vehicle" group show the lowest activity and a negative discrimination between the active lever and the inactive lever.

The rats of the groups chemo-induced or not induced and treated with CPE show better learning and memorization capacities than the rats of the other groups.

Figure 65:
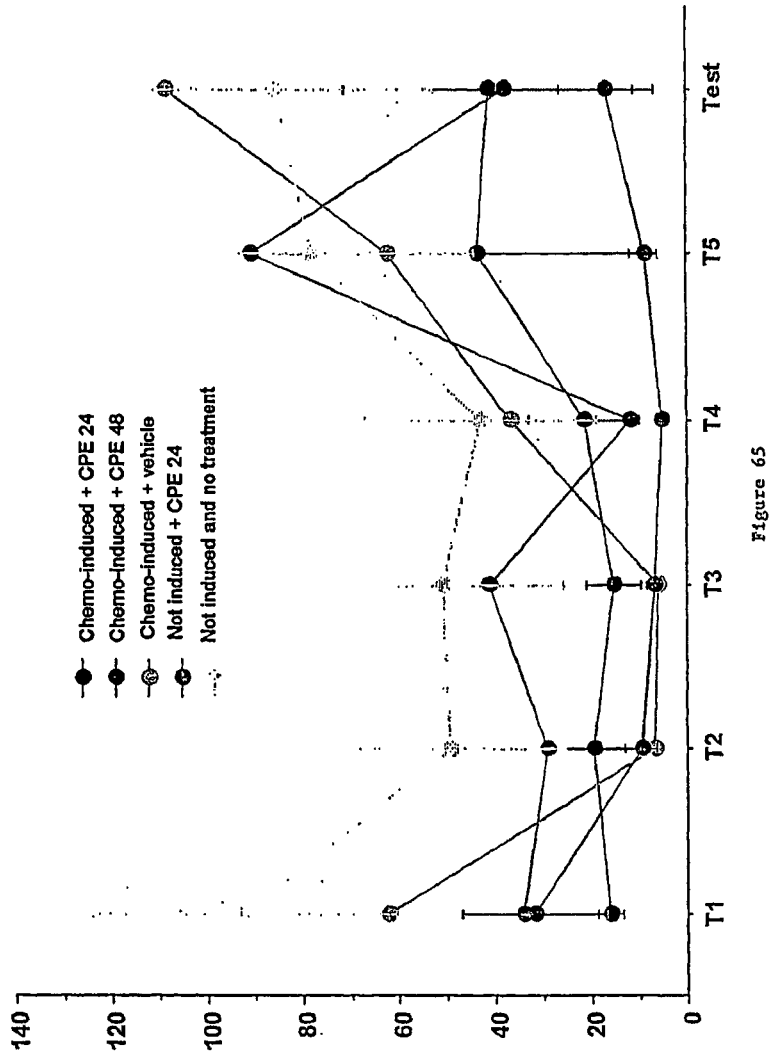

Morris (see FIG. 65)
- The rats of the groups chemo-induced or not, treated with CPE at 24 mg/kg learn and memorize better than the rats of the other groups,
- the rats of the "chemo-induced+vehicle" and "not induced and not treated" groups show great difficulty in learning and in spatial memorization.

The learning and spatial memorization of the rats of the groups chemo-induced or not induced and treated with CPE at 24 or 48 mg/kg is better than that of the rats of the "chemo-induced+vehicle" and "not induced and not treated" groups.

Figure 66:
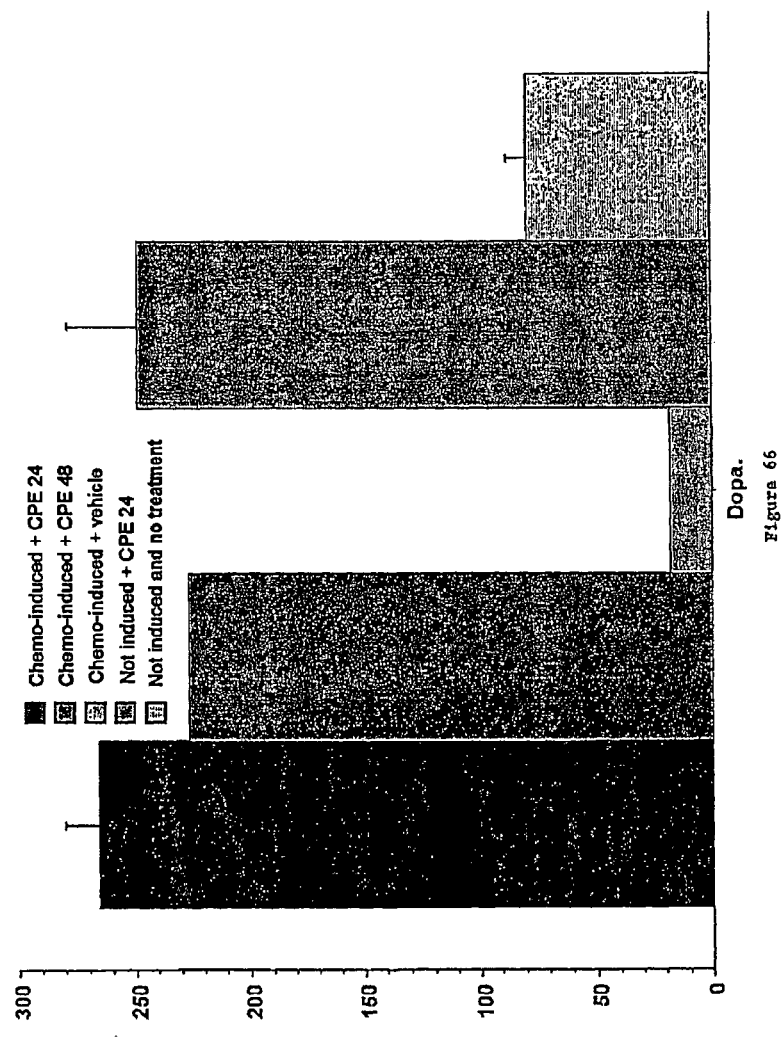

Dopamine Assay (See FIG. 66)
- The urinary dopamine level of the rats of the "chemo-induced+CPE 24" and "chemo-induced+CPE 48" groups is higher than that of the rats of the "chemo-induced+vehicle" and "not induced and not treated" groups and is comparable with that observed for the group of "not induced+CPE 24" rats,
- the urinary dopamine level of the rats of the "not induced and not treated" groups decreases gradually over time and approaches that of the rats of the "chemo-induced+vehicle" groups.

CPE administered at 24 or 48 mg/kg makes it possible to maintain a high urinary dopamine level in the rats subjected or not subjected to induction of prostate tumors, this level being higher than that of the rats not induced and not treated.

Result of the Overall Anatomopathological Analyses Performed
- Group 1 (chemo-induced+vehicle): 10 tumors out of 13 samples analyzed ⇒ 76.9% tumoral incidence
- Group 2 (chemo-induced+CPE 24): 0 tumors out of 6 samples analyzed ⇒ 0.0% tumoral incidence
- Group 3 (chemo-induced+CPE 48): 5 tumors out of 12 samples analyzed ⇒ 41.7% tumoral incidence
- Group 4 (not induced+vehicle): 0 tumors out of 4 samples analyzed ⇒ 0.0% tumoral incidence
- Group 5 (not induced and not treated): 0 tumors out of 6 samples analyzed ⇒ 0.0% tumoral incidence

EXAMPLE 12

Antioxidant Activity of the Extract According to the Invention

The object of this study is to evaluate the antioxidant effects of plain chocolate enriched with a cocoa polyphenol extract, administered daily for 4 weeks to fasted healthy subjects (18-30 years old).

Protocol:

Subjects: The subjects are healthy, fasted, sporty volunteers of Caucasian type, performing 4 to 6 hours of sport per week, from 18 to 30 years old, and weighing between 60 and 80 kg. Their dietary habits remain unchanged. They are also non-smokers and have no history of cardiovascular, respiratory or neuromuscular diseases or articular disorders. The volunteers carry a notebook indicating the food consumed during the study.

Products:
- plain chocolate as placebo (64% cocoa paste originating from the Ivory Coast, 26.5% sugar, 9% cocoa butter, emulsifier: soybean lecithin, total fat: 43%)
- plain chocolate (64% cocoa paste originating from the Ivory Coast), enriched with 102.10 mg of vitamin E
- plain chocolate (67.5% cocoa paste originating from Tanzania, 23.5% sugar, 9% cocoa butter, natural vanilla, total fat: 43%), enriched with 47.93 mg of cocoa polyphenol extract.

Dose: a bar of chocolate at lunchtime, at the end of the meal.

result: The group which ingested the plain chocolate supplemented with polyphenol extract shows a significant increase in total cholesterol, in LDL cholesterol and in β-carotene, whereas the vitamin E and the malondialdehyde significantly decreased between day 0 and day 28, after 4 weeks of treatment by oral administration.

This result indicates a significant antioxidant activity of plain chocolate enriched with polyphenol extract, in comparison with unenriched plain chocolate.

The invention claimed is:

1. A method for treating prostate hyperplasia comprising administering a patient in need thereof a medicament comprising a cocoa polyphenol extract, wherein the cocoa polyphenol extract comprises:
   20% to 50% by mass of polyphenols, wherein the polyphenols comprises 55% to 80% by mass flavonoids,
   3% to 15% by mass of lipids, wherein the lipids comprise 1% to 15% by mass β-sitosterol, and
   5% to 20% by mass of xanthines.

2. The method of claim 1, characterized in that the treatment relates to a benign hyperplasia of the prostate.

3. The method of claim 1, characterized in that the treatment relates to a prostate hyperplasia resulting from a prostate cancer.

4. The method of claim 1, characterized in that the medicament is administered orally, intravenously or via subcutaneous injection.

5. The method of claim 1, characterized in that the medicament is administered at a dose of from 15 to 30 mg/kg/day orally.

6. The method of claim 1, characterized in that the medicament is administered at a dose of from 40 to 60 mg/kg/day orally.

* * * * *

UNITED STATES PATENT AND TRADEMARK OFFICE
CERTIFICATE OF CORRECTION

PATENT NO.       : 8,435,576 B2                                                                 Page 1 of 1
APPLICATION NO.  : 11/883265
DATED            : May 7, 2013
INVENTOR(S)      : Troplin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1198 days.

Signed and Sealed this
Eighth Day of September, 2015

Michelle K. Lee
*Director of the United States Patent and Trademark Office*